US010835620B2

(12) United States Patent
Koch et al.

(10) Patent No.: US 10,835,620 B2
(45) Date of Patent: Nov. 17, 2020

(54) METHODS FOR TREATING HEART FAILURE USING BETA-ARKNT PEPTIDE

(71) Applicant: Temple University—Of The Commonwealth System of Higher Education, Philadelphia, PA (US)

(72) Inventors: Walter J. Koch, Malvern, PA (US); Sarah M. Schumacher-Bass, Landsdale, PA (US)

(73) Assignee: TEMPLE UNIVERSITY-OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 16/306,718

(22) PCT Filed: Jun. 5, 2017

(86) PCT No.: PCT/US2017/035897
§ 371 (c)(1),
(2) Date: Dec. 3, 2018

(87) PCT Pub. No.: WO2017/210671
PCT Pub. Date: Dec. 7, 2017

(65) Prior Publication Data
US 2019/0134223 A1 May 9, 2019

Related U.S. Application Data

(60) Provisional application No. 62/345,273, filed on Jun. 3, 2016.

(51) Int. Cl.
| | |
|---|---|
| *A61P 9/04* | (2006.01) |
| *A61K 48/00* | (2006.01) |
| *A61K 38/43* | (2006.01) |
| *C12N 15/63* | (2006.01) |
| *C12N 15/85* | (2006.01) |
| *C12N 9/12* | (2006.01) |
| *C07K 14/47* | (2006.01) |
| *C12N 15/11* | (2006.01) |
| *A61K 38/00* | (2006.01) |

(52) U.S. Cl.
CPC ........... *A61K 48/005* (2013.01); *A61K 38/43* (2013.01); *A61K 48/00* (2013.01); *A61P 9/04* (2018.01); *C12N 9/12* (2013.01); *C12N 15/63* (2013.01); *C12N 15/85* (2013.01); *C12Y 207/11015* (2013.01); *A61K 38/00* (2013.01); *C07K 14/47* (2013.01); *C12N 15/11* (2013.01); *C12N 2750/14143* (2013.01)

(58) Field of Classification Search
None
See application file for complete search history.

(56) References Cited

U.S. PATENT DOCUMENTS

2009/0082410 A1 3/2009 Oakley

OTHER PUBLICATIONS

"RecName: Full=Beta-adrenergic receptor kinase 1; Short=Beta-ARK-1; AltName: Full=G-protein-coupled receptor kinase 2", UniProtKB, (20141126), Database accession No. P21146, XP055446986 (11 pages).
Keys et al., "Cardiac hypertrophy and altered Beta-adrenergic signaling in transgenic mice that express the amino terminus of Beta-ARK1", Am J Physiol Heart Circ Physiol., (20030000), vol. 285, No. 5, pp. H2201-H2211, XP055446988.
Murga et al., "High Affinity Binding of Beta-Adrenergic Receptor Kinase to Microsomal Membranes", J Biol Chem., (19960000), vol. 271, No. 2, pp. 985-994, XP055446980.
Rockman et al., "Expression of a b-adrenergic receptor kinase 1 inhibitor prevents the development of myocardial failure in gene-targeted mice", Proc Natl Acad Sci USA, (19980000), vol. 95, No. 12, pp. 7000-7005, XP002961018.
Schumacher et al., 2015, "Abstract 365: Domain-specific Roles for GRK2 in Cardiac Hypertrophy and Heart Failure" Circulation Research 117:A365.
Schumacher et al., 2015, "Paroxetine-mediated GRK2 inhibition reverses cardiac dysfunction and remodeling after myocardial infarction" Science Translational Medicine 7:277ra31.
Tachibana et al., "Level of Beta-Adrenergic Receptor Kinase 1 Inhibition Determines Degree of Cardiac Dysfunction After Chronic Pressure Overload-Induced Heart Failure", Circulation, (20050000), vol. 111, No. 5, pp. 591-597, XP055446999.

*Primary Examiner* — Zachary C Howard
(74) *Attorney, Agent, or Firm* — Riverside Law LLP

(57) ABSTRACT

This invention is generally related to novel compositions for treating or preventing heart failure. Specifically, the disclosure provides a composition comprising an amino-terminal domain of Beta.adrenergic receptor kinase-1 (Beta.ARKnt) peptide, or a nucleic acid encoding Beta.ARKnt. Further disclosed are methods of using the compositions for treating or preventing heart failure in a subject or for altering Beta.-adrenergic receptor (Beta.AR) density in a subject.

3 Claims, 54 Drawing Sheets

Specification includes a Sequence Listing.

Pro-Hypertrophic Line: Cardiac-specific
βARK-NT – GRK2 nt expression

Pro Heart Failure Line: Cardiac-specific
BK12 – GRK2 expression

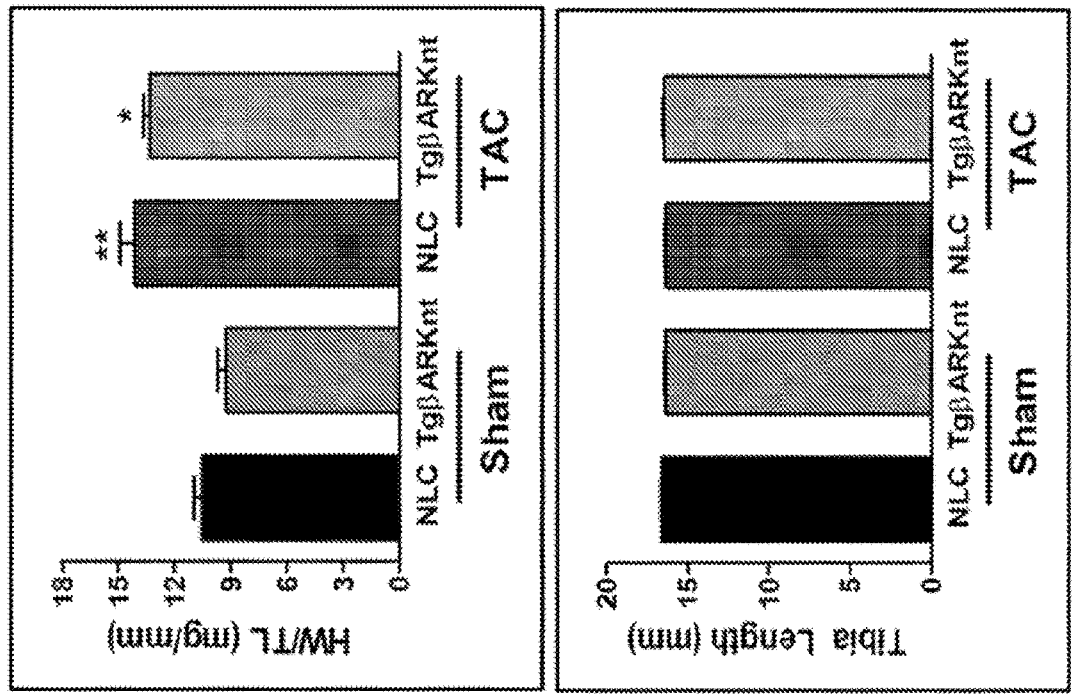
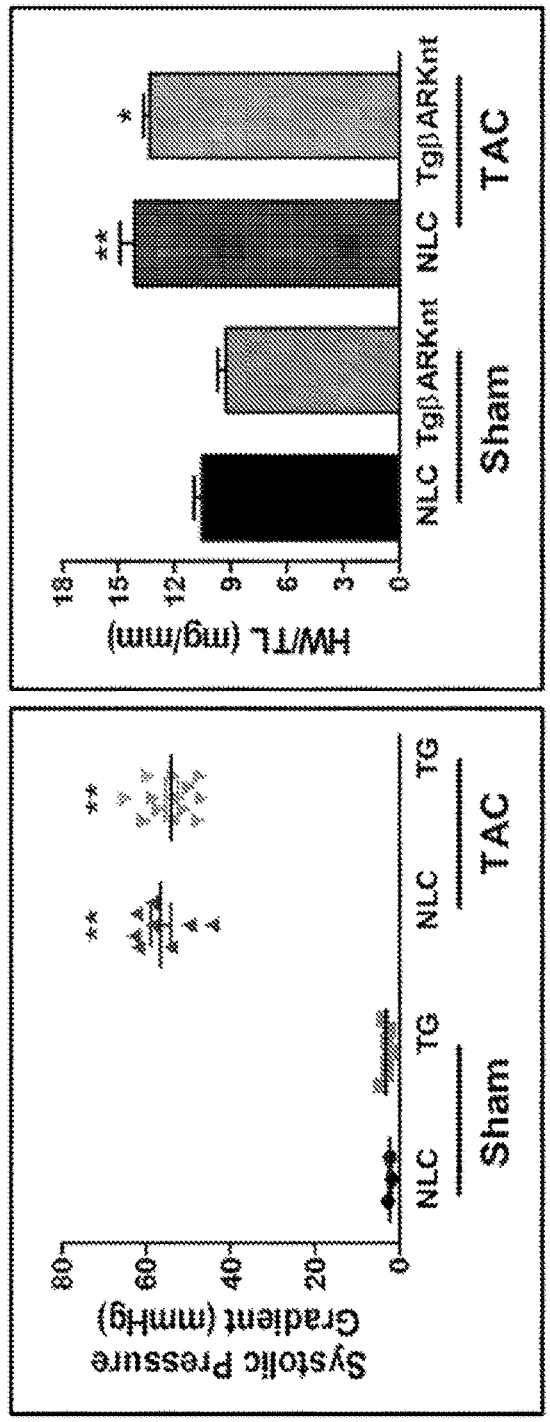
Figure 10A
Figure 10B
Figure 10C
Figure 10D

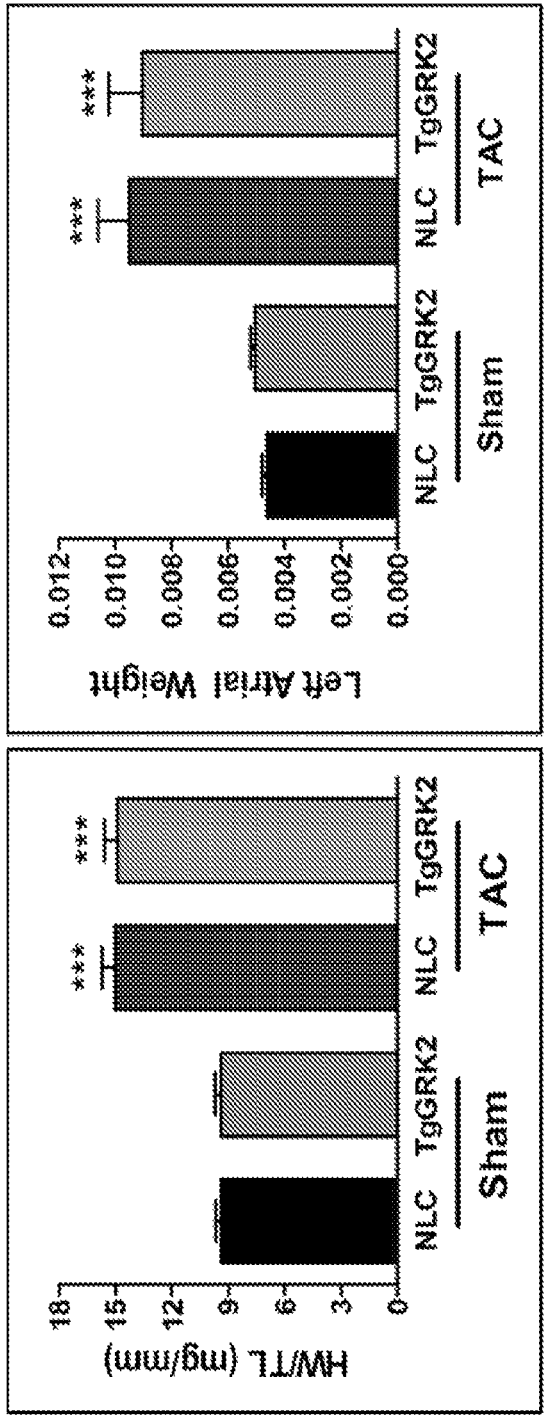
Figure 16B
Figure 16A
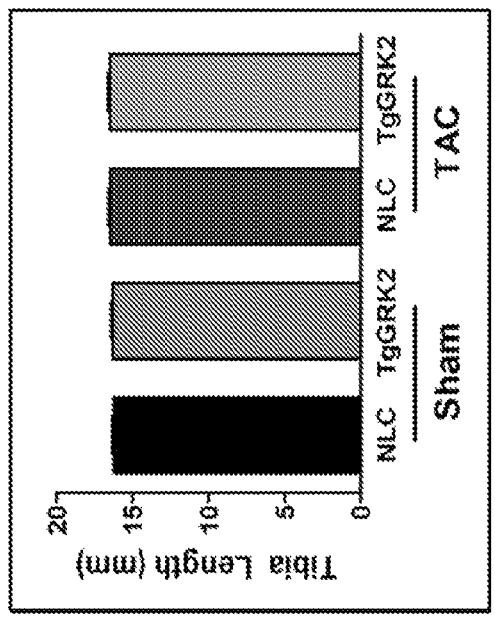
Figure 16C

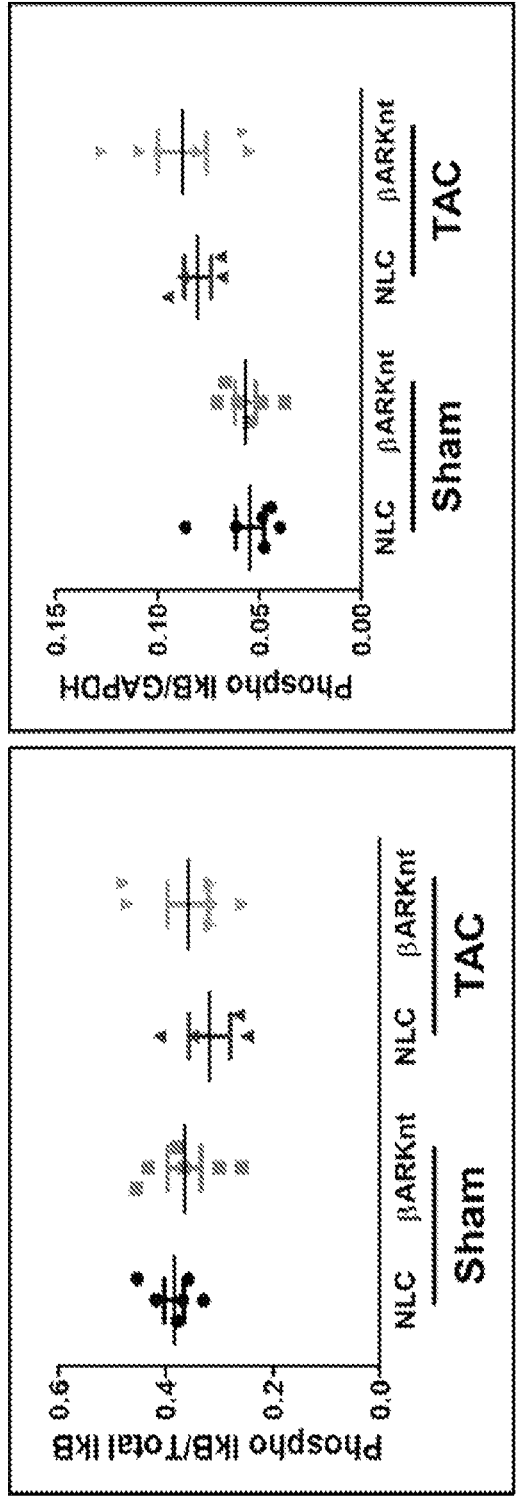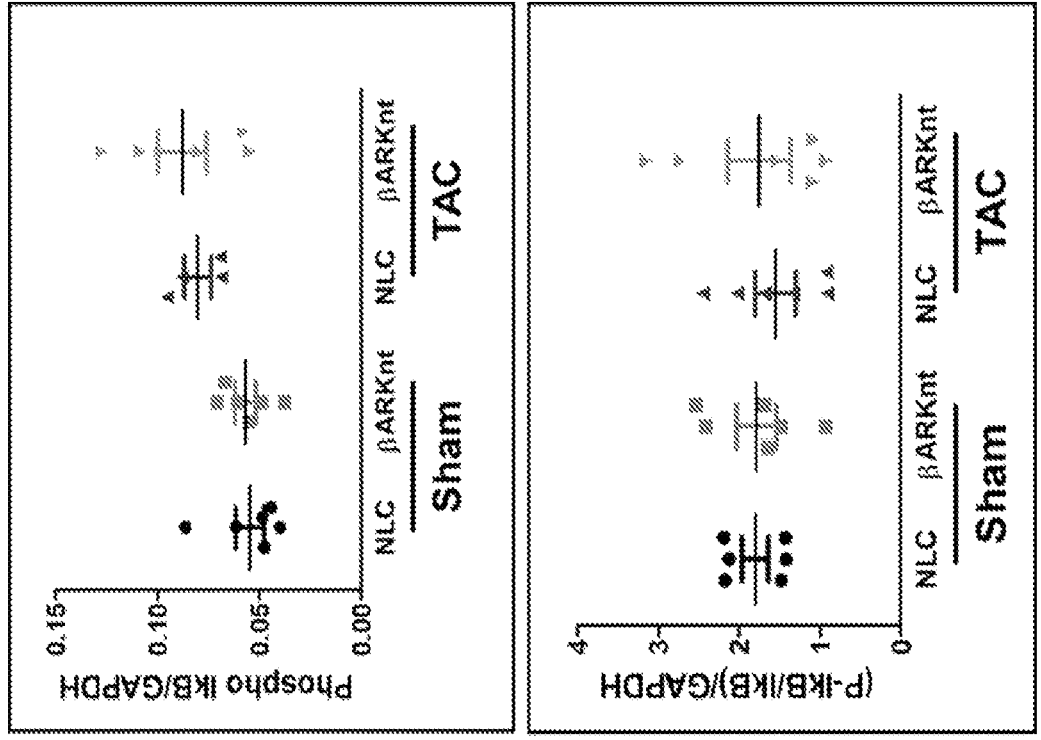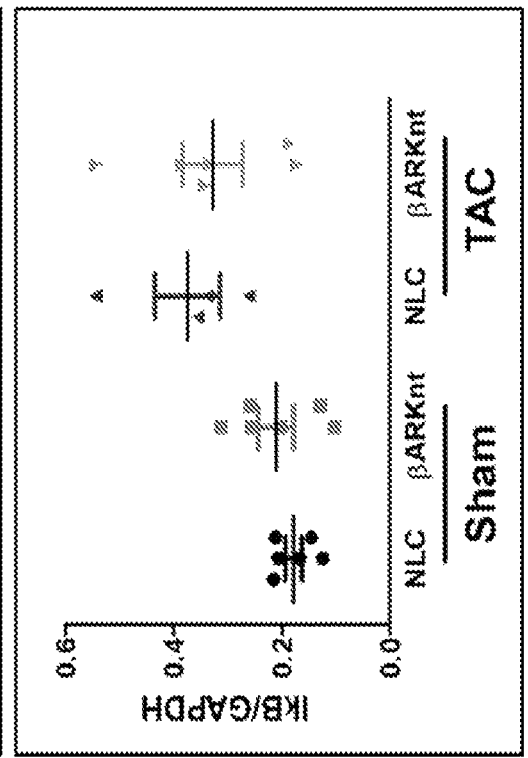
Figure 28A
Figure 28B
Figure 28C
Figure 28D

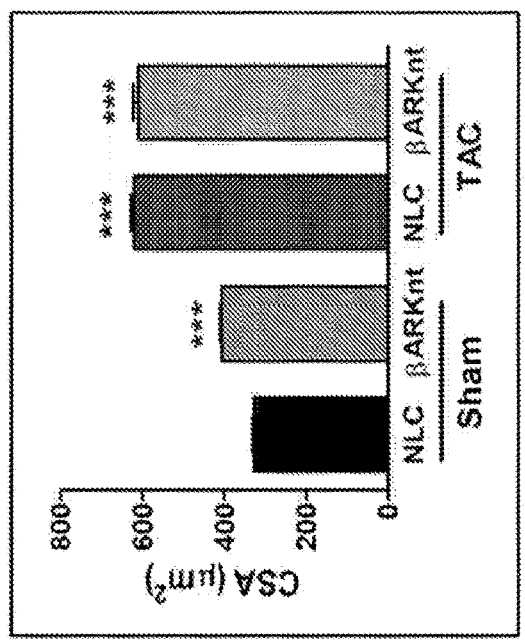
Figure 37E
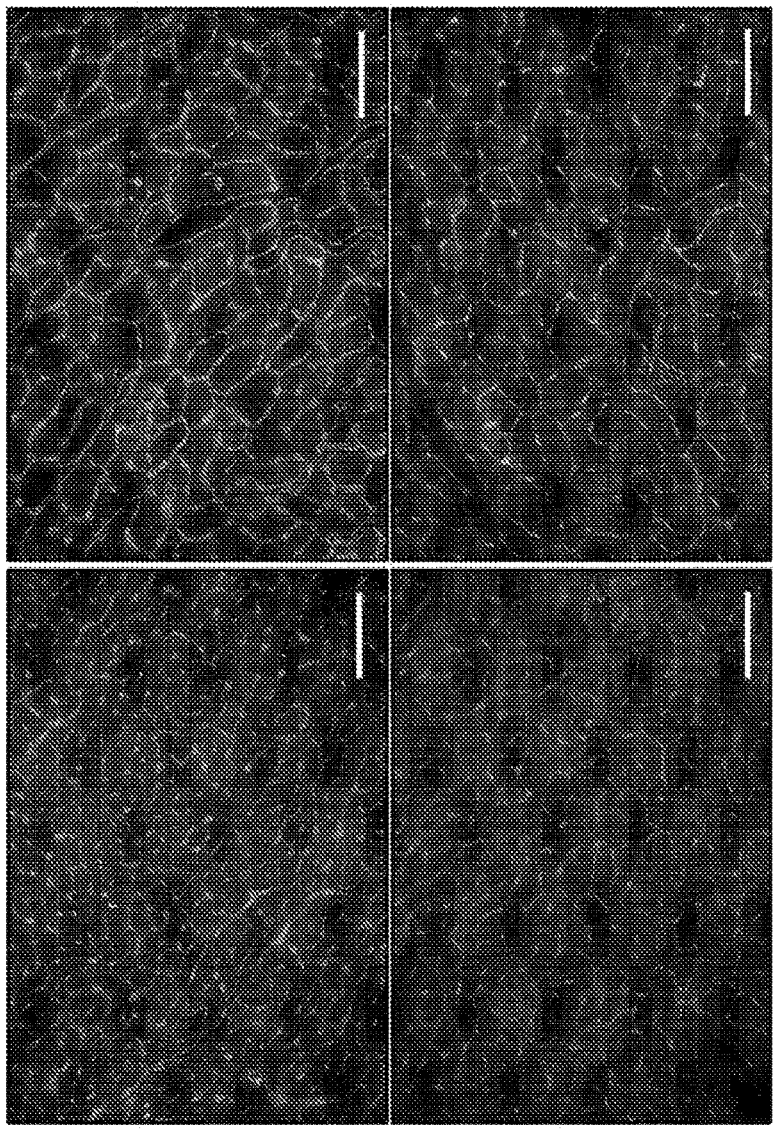
Figure 37A
Figure 37B
Figure 37C
Figure 37D

METHODS FOR TREATING HEART FAILURE USING BETA-ARKNT PEPTIDE

CROSS-REFERENCE TO RELATED APPLICATIONS

This application is a U.S. national phase application filed under 35 U.S.C. § 371 claiming benefit to PCT International Patent Application No. PCT/US2017/035897, filed on Jun. 5, 2017, which claims priority to U.S. Provisional Application No. 62/345,273, filed Jun. 3, 2016, each of which disclosures is incorporated herein by reference in its entirety.

STATEMENT REGARDING FEDERALLY SPONSORED RESEARCH OR DEVELOPMENT

This invention was made with government support under Grant Numbers R37 HL061690 and P01 HL075443 awarded by National Institutes of Health. The government has certain rights in the invention.

BACKGROUND OF THE INVENTION

Signaling via G protein-coupled receptors (GPCRs) is critical for normal heart function, and during disease GPCRs are uncoupled from their downstream effectors and receptor number is reduced. Signaling through these receptors is tightly controlled by GPCR kinases (GRKs) and one in particular, GRK2 (originally known as βARK1), has been shown to be intimately involved in heart failure (HF) progression. GRK2 upregulation in failing hearts represents one of the first molecular changes that occur after cardiac injury, and lowering GRK2 restores GPCR levels and preserves cardiac function. However, ongoing research has demonstrated great diversity in the functional roles of GRK2, including phosphorylation of non-GPCR substrates and numerous phosphorylation-independent regulatory binding partners. Many binding sites within GRK2 have been identified for such protein-protein interactions, and several are important for adaptive and maladaptive myocyte growth. However, to date it was not known whether domain-specific interactions with signaling and regulatory molecules could lead to novel targets for HF therapy.

Thus, there is a need in the art for novel approaches for HF therapy, including through the use of GRK2/βARK1 based therapies. The present invention addresses this unmet need.

SUMMARY OF THE INVENTION

In one aspect, the present invention provides a βARKnt peptide, a nucleic acid encoding a βARKnt peptide, or a composition comprising a βARKnt peptide or nucleic acid encoding a βARKnt peptide. In one embodiment, the βARKnt peptide comprises an amino acid sequence at least 90% homologous to SEQ ID NO:1. In one embodiment, the βARKnt peptide comprises the amino acid sequence of SEQ ID NO:1.

In one embodiment, the nucleic acid encoding a βARKnt peptide is contained within a vector. In one embodiment, the vector is an AAV vector. In one embodiment, the AAV vector is an AAV6 or AAV9. In one embodiment, the AAV vector comprises an EF1alpha promoter. In one embodiment, the EF1alpha promoter comprises mir122.

In another aspect, the invention provides a method for treating or preventing heart failure in a subject. In one embodiment, the method comprises βARKnt peptide, a nucleic acid encoding a βARKnt peptide, or a composition comprising a βARKnt peptide or nucleic acid encoding a βARKnt peptide. In one embodiment, the βARKnt peptide comprises an amino acid sequence at least 90% homologous to SEQ ID NO:1. In one embodiment, the βARKnt peptide comprises the amino acid sequence of SEQ ID NO:1. In one embodiment, the subject is human.

In another aspect, the invention provides a method for altering β-adrenergic receptor (βAR) density in a subject. In one embodiment, the method comprises βARKnt peptide, a nucleic acid encoding a βARKnt peptide, or a composition comprising a βARKnt peptide or nucleic acid encoding a βARKnt peptide. In one embodiment, the βARKnt peptide comprises an amino acid sequence at least 90% homologous to SEQ ID NO:1. In one embodiment, the βARKnt peptide comprises the amino acid sequence of SEQ ID NO:1.

In one embodiment, βAR density is increased. In one embodiment, the subject has low βAR density.

In one embodiment, the method further comprises administering a second therapeutic. In one embodiment, the second therapeutic is a βAR agonist.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts a diagram of βARK1 (GRK2) and FIG. 1B depicts a gel confirming the presence of βARK1 in transgenic animals.

FIG. 2, comprising FIG. 2A depicts a diagram and text outlining the experimental design utilized in example experiments. FIG. 2B depicts a diagram and text outlining the experimental design utilized in example experiments.

FIG. 3, comprising FIG. 3A depicts a mouse model of cardiac pressure overload using TAC. FIG. 3B depicts a mouse model of cardiac pressure overload using TAC. FIG. 3C depicts a mouse model of cardiac pressure overload using TAC.

FIG. 4, comprising FIG. 4A depicts ejection fraction plotted as a function of group (NLC Sham, TgβARKnt Sham, NLC TAC, TgβARKnt TAC), at 0 and 4 weeks. FIG. 4B depicts left ventricular mass plotted as a function of time (data taken at week 0, week 2, and week 4) for the four groups (NLC Sham, βARKnt Sham, NLC TAC, ηARKnt TAC). FIG. 4C depicts Left Ventricular Posterior Wall diastole (LVPWd, in mm) for the four groups (NLC Sham, βARKnt Sham, NLC TAC, (βARKnt TAC). FIG. 4D depicts Left Ventricular Posterior Wall systole (LVPWs, in mm) for the four groups (NLC Sham, βARKnt Sham, NLC TAC, βARKnt TAC). *P=0.01; ***P<0.0001 by two-way ANOVA with repeated measures and Bonferroni relative to NLC Sham. ττττP<0.0001 by two-way ANOVA with repeated measures and Bonferroni relative to NLC TAC. n=9 to 17 mice per group.

FIG. 5, comprising FIG. 5A depicts HW/TL (mg/mm) plotted as a function of group (NLC Sham, TgβARKnt Sham, NLC TAC, TgβARKnt TAC). FIG. 5B depicts % change in HW/TL plotted as a function of group (NLC Sham, TgβARKnt Sham, NLC TAC, TgβARKnt TAC). FIG. 5C depicts left atrial weight plotted as a function of group (NLC Sham, TgβARKnt Sham, NLC TAC, TgβARKnt TAC). FIG. 5D depicts tibia length (mm) plotted as a function of group (NLC Sham, TgβARKnt Sham, NLC TAC, TgβARKnt TAC). P=0.001; *P<0.0001 by one-way ANOVA with Tukey relative to NLC Sham. n=9 to 17 mice per group.

FIG. 6, comprising FIG. 6A depicts ANF (Fold Change) plotted as a function of group (NLC Sham, TgβARKnt Sham, NLC TAC, TgβARKnt TAC). FIG. 6B depicts BNP (Fold Change) plotted as a function of group (NLC Sham, TgβARKnt Sham, NLC TAC, TgβARKnt TAC). FIG. 6C depicts fβMHC (Fold Change) plotted as a function of group (NLC Sham, TgβARKnt Sham, NLC TAC, TgβARKnt TAC). n=12, 11, 12, 12. *P=0.01; ***P<0.0001 by nonparametric one-way ANOVA with Dunns post-hoc test.

FIG. 7, comprising FIG. 7A depicts a diagram depicting signaling pathways relevant in heart failure. FIG. 7B depicts LVPWs (mm) plotted as a function of time (data taken at week 0, week 2, and week 4), for the four groups (NLC Sham, TgGRK2 Sham, NLC TAC, TgGRK2 TAC). FIG. 7C depicts LV mass (mg) as a function of time (data taken at week 0, week 2, and week 4), for the four groups (NLC Sham, TgGRK2 Sham, NLC TAC, TgGRK2 TAC). FIG. 7D depicts HW/TL (mg/mm) plotted as a function of group (NLC Sham, TgGRK2 Sham, NLC TAC, TgGRK2 TAC). FIG. 7E depicts left atrial weight (g) plotted as a function of group (NLC Sham, TgGRK2 Sham, NLC TAC, TgGRK2 TAC). *P=0.01; P=0.001; *P<0.0001 by two-way ANOVA with repeated measures and Bonferroni or one-way ANOVA with Tukey relative to NLC sham. n=8 to 14 mice per group. See Schumacher S M, et al. Sci. Signal. 22 Mar. 2016 Vol. 9, Issue 420, pp. ra30.

FIG. 8, comprising FIG. 8A depicts relevant signaling pathways. FIG. 8B depicts LVPWs (mm) plotted as a function of time (data taken at week 0, week 2, and week 4), for the four groups (NLC Sham, βARKct Sham, NLC TAC, βARKct TAC). FIG. 8C depicts LV mass (mg) plotted as a function of time (data taken at week 0, week 2, and week 4), for the four groups (NLC Sham, βARKct Sham, NLC TAC, βARKct TAC). FIG. 8D depicts HW/TL (mg/mm) plotted as a function of group (NLC Sham, TgβARKct Sham, NLC TAC, TgβARKct TAC). FIG. 8E depicts left atrial weight plotted as a function of group (NLC Sham, TgβARKct Sham, NLC TAC, TgβARKct TAC). *P=0.01; P=0.001; *P<0.0001 by two-way ANOVA with repeated measures and Bonferroni or one-way ANOVA with Tukey relative to NLC sham. n=8 to 14 mice per group. See Schumacher S M, et al. Sci. Signal. 22 Mar. 2016 Vol. 9, Issue 420, pp. ra30.

FIG. 9, comprising FIG. 9A depicts ejection fraction (%) measured over time for the four groups (NLC Sham, βARKnt Sham, NLC TAC, βARKnt TAC). FIG. 9B depicts LV mass (mg) measured over time for the four groups (NLC Sham, βARKnt Sham, NLC TAC, βARKnt TAC). FIG. 9C depicts LVPWs (mm) measured over time for the four groups (NLC Sham, βARKnt Sham, NLC TAC, βARKnt TAC). FIG. 9D depicts LVPWd (mm) measured over time for the four groups (NLC Sham, βARKnt Sham, NLC TAC, βARKnt TAC). *, p=0.01; , p=0.001; *, p<0.0001 by two-way ANOVA with repeated measures and Bonferroni post-hoc test relative to NLC Sham mice. τ, p=0.01; ττ, p=0.001; τττ, p<0.0001 by two-way ANOVA with repeated measures and Bonferroni post-hoc test relative to NLC TAC mice. n=9-15 mice per group.

FIG. 10, comprising FIG. 10A through FIG. 10D, depicts results from example experiments demonstrating that chronic pressure-overload induced HF is blocked by cardiac βARKnt expression. FIG. 10A depicts systolic pressure gradient (mm Hg) for the four groups (NLC Sham, TgβARKnt Sham, NLC TAC, TgβARKnt TAC). FIG. 10B depicts HW/TL (mg/mm) for the four groups (NLC Sham, TgβARKnt Sham, NLC TAC, TgβARKnt TAC). FIG. 10C depicts left atrial weight for the four groups (NLC Sham, TgβARKnt Sham, NLC TAC, TgβARKnt TAC). FIG. 10D depicts tibia length (mm) for the four groups (NLC Sham, TgβARKnt Sham, NLC TAC, TgβARKnt TAC). *, p=0.01; , p=0.001; *, p<0.0001 by Kruskal-Wallis nonparametric one-way ANOVA and Dunns post-hoc test relative to NLC Sham mice. n=9-15 mice per group.

FIG. 11, comprising FIG. 11A depicts ANF (Fold Change) plotted as a function of group (NLC Sham, TgβARKnt Sham, NLC TAC, TgβARKnt TAC). FIG. 11B depicts BNP (Fold Change) plotted as a function of group (NLC Sham, TgβARKnt Sham, NLC TAC, TgβARKnt TAC). FIG. 11C depicts βMHC (Fold Change) plotted as a function of group (NLC Sham, TgβARKnt Sham, NLC TAC, TgβARKnt TAC). n=9, 11, 13, 12. *P=0.01; P=0.001; *P<0.0001 by nonparametric one-way ANOVA with Dunns post-hoc test.

FIG. 12, comprising FIG. 12A depicts ejection fraction (%) plotted as a function of time (weeks) for each group (NLC Sham, βARKnt Sham, NLC TAC, βARKnt TAC). FIG. 12B depicts LV mass (mg) plotted as a function of time (weeks) for each group (NLC Sham, βARKnt Sham, NLC TAC, βARKnt TAC). FIG. 12C depicts LVIDs (mm) plotted as a function of time (weeks) for each group (NLC Sham, βARKnt Sham, NLC TAC, βARKnt TAC). FIG. 12D depicts LVPWs (mm) plotted as a function of time (weeks) for each group (NLC Sham, βARKnt Sham, NLC TAC, βARKnt TAC). P=0.001; *P<0.0001 by two-way ANOVA with repeated measures and Bonferroni relative to NLC Sham. TP=0.01 by two-way ANOVA with repeated measures and Bonferroni relative to NLC TAC. n=9 to 13 mice per group.

FIG. 13, comprising FIG. 13A depicts HW/TL (mg/mm) plotted as a function of group (NLC Sham, TgβARKct Sham, NLC TAC, TgβARKct TAC). FIG. 13B depicts left atrial weight plotted as a function of group (NLC Sham, TgβARKct Sham, NLC TAC, TgβARKct TAC). FIG. 13C depicts tibia length (mm) plotted as a function of group (NLC Sham, TgβARKct Sham, NLC TAC, TgβARKct TAC). P=0.001; *P<0.0001 by one-way ANOVA with Tukey relative to NLC Sham. n=9 to 13 mice per group.

FIG. 14, comprising FIG. 14A depicts ANF (Fold Change) plotted as a function of group (NLC Sham, TgβARKct Sham, NLC TAC, TgβARKct TAC). FIG. 14B depicts BNP (Fold Change) plotted as a function of group (NLC Sham, TgβARKct Sham, NLC TAC, TgβARKct TAC). FIG. 14C depicts βMHC (Fold Change) plotted as a function of group (NLC Sham, TgβARKct Sham, NLC TAC, TgβARKct TAC). *P=0.01; ***P<0.0001 by one-way ANOVA with Tukey relative to NLC Sham. n=9 to 13 mice per group.

FIG. 15, comprising FIG. 15A depicts ejection fraction (%) plotted as a function of time (weeks), for each group (NLC Sham, TgGRK2 Sham, NLC TAC, TgGRK2 TAC). FIG. 15B depicts LV mass (mg) plotted as a function of time (weeks), for each group (NLC Sham, TgGRK2 Sham, NLC TAC, TgGRK2 TAC). FIG. 15C depicts LVIDs (mm) plotted as a function of time (weeks), for each group (NLC Sham, TgGRK2 Sham, NLC TAC, TgGRK2 TAC). FIG. 15D depicts LVPWs (mm) plotted as a function of time (weeks), for each group (NLC Sham, TgGRK2 Sham, NLC TAC, TgGRK2 TAC). *P=0.01 P=0.001; *P<0.0001 by two-way ANOVA with repeated measures and Bonferroni relative to NLC Sham. n=9 to 12 mice per group.

FIG. 16, comprising FIG. 16A through FIG. 16C, depicts results from example experiments demonstrating that cardiac GRK2 overexpression hastens progression to heart failure during chronic pressure-overload. FIG. 16A depicts HW/TL (mg/mm) plotted as a function of group (NLC Sham, TgGRK2 Sham, NLC TAC, TgGRK2 TAC). FIG. 16B depicts left atrial weight plotted as a function of group (NLC Sham, TgGRK2 Sham, NLC TAC, TgGRK2 TAC). FIG. 16C depicts tibia length (mm) plotted as a function of group (NLC Sham, TgGRK2 Sham, NLC TAC, TgGRK2 TAC). ***P<0.0001 by one-way ANOVA with Tukey relative to NLC Sham. n=9 to 12 mice per group.

FIG. 17, comprising FIG. 17A depicts HW/TL (mg/mm) plotted as a function of group (NLC Sham, TgGRK2 Sham, NLC TAC, TgGRK2 TAC). FIG. 17B depicts left atrial weight (g) plotted as a function of group (NLC Sham, TgGRK2 Sham, NLC TAC, TgGRK2 TAC). FIG. 17C depicts tibia length (mm) plotted as a function of group (NLC Sham, TgGRK2 Sham, NLC TAC, TgGRK2 TAC). ***P<0.0001 by one-way ANOVA with Tukey relative to NLC Sham. n=9 to 12 mice per group.

FIG. 18, comprising FIG. 18A depicts immunoprecipitation using anti-FLAG antibody, followed by western blot probed with anti-Gαq antibody. FIG. 18B depicts SDS-PAGE analysis, showing pre-IP, post-FLAG-IP, and post-Ms-IgG-IP for TG Sham and TG TAC groups. FIG. 18C depicts βARKnt-flag/GAPDH for the three groups pre-IP, FLAG-IP, and Ms-IgG-IP (n=8). FIG. 18D depicts immunoprecipitated (IP'd) βARKnt-FLAG for sham and TAC groups (n=8). FIG. 18E depicts Gαq/GAPDH quantitation for the three groups pre-IP, FLAG-IP, and Ms-IgG-IP (n=8). ***, p<0.0001 by nonparametric one-way ANOVA with Dunns relative to the Pre-immunoprecipitation control. n=8 mice per group.

FIG. 19, comprising FIG. 19A depicts a signaling pathway (GqGPCRs). FIG. 19B depicts IP3 levels (pg/mL) for each of the four groups (NLC Sham, TgβARKnt Sham, NLC TAC, TgβARKnt TAC). ***, p<0.0001 by one-way ANOVA with Tukey or Bonferroni post-hoc test. n=12, 6, 14, 10 respectively.

FIG. 20, comprising FIG. 20A depicts $β_1$AR (Fold Change) plotted as a function of group (NLC Sham, TgβARKnt Sham, NLC TAC, TgβARKnt TAC). FIG. 20B depicts $β_2$AR (Fold Change) plotted as a function of group (NLC Sham, TgβARKnt Sham, NLC TAC, TgβARKnt TAC). n=12, 11, 12, 12. *P=0.01 by nonparametric one-way ANOVA with Dunns post-hoc test.

FIG. 21, comprising FIG. 21A depicts $β_1$AR (Fold Change) plotted as a function of group (NLC Sham, TgβARKnt Sham, NLC TAC, TgβARKnt TAC). FIG. 21B depicts $β_2$AR (Fold Change) plotted as a function of group (NLC Sham, TgβARKnt Sham, NLC TAC, TgβARKnt TAC). n=9, 11, 13, 12.

FIG. 22 depicts $B_{max}$ (fmol/mg protein) plotted as a function of group (NLC Sham, TgβARKnt Sham, NLC TAC, TgβARKnt TAC). n=7, 8, 11, 12. *P=0.01 by nonparametric one-way ANOVA with Dunns post-hoc test.

FIG. 23, comprising FIG. 23A depicts FGFS (Fold Change) plotted as a function of group (NLC Sham, βARKnt Sham, NLC TAC, βARKnt TAC). FIG. 23B depicts VE-Cadherin (Fold Change) plotted as a function of group (NLC Sham, βARKnt Sham, NLC TAC, βARKnt TAC). FIG. 23C depicts eNOS (Fold Change) plotted as a function of group (NLC Sham, βARKnt Sham, NLC TAC, βARKnt TAC). n=8, 7, 11, 10 each.

FIG. 24, comprising FIG. 24A depicts VEGF A (Fold Change) plotted as a function of group (NLC Sham, βARKnt Sham, NLC TAC, βARKnt TAC). FIG. 24B depicts CD31 (Fold Change) plotted as a function of group (NLC Sham, βARKnt Sham, NLC TAC, βARKnt TAC). FIG. 24C depicts HIF1α (Fold Change) plotted as a function of group (NLC Sham, βARKnt Sham, NLC TAC, βARKnt TAC). FIG. 24D depicts VEGF R1 (Fold Change) plotted as a function of group (NLC Sham, βARKnt Sham, NLC TAC, βARKnt TAC). n=8, 7, 11, 10 each. *P=0.01; **P=0.001; by nonparametric one-way ANOVA with Dunns post-hoc test.

FIG. 25, comprising FIG. 25A depicts Col I (Fold Change) plotted as a function of group (NLC Sham, βARKnt Sham, NLC TAC, βARKnt TAC). FIG. 25B depicts Col III (Fold Change) plotted as a function of group (NLC Sham, βARKnt Sham, NLC TAC, βARKnt TAC). FIG. 25C depicts αSMA (Fold Change) plotted as a function of group (NLC Sham, βARKnt Sham, NLC TAC, βARKnt TAC). n=11 per group. P=0.001; *P<0.0001 by nonparametric one-way ANOVA with Dunns post-hoc test.

FIG. 26, comprising FIG. 26A depicts MMP2 (Fold Change) plotted as a function of group (NLC Sham, βARKnt Sham, NLC TAC, βARKnt TAC). FIG. 26B depicts MMP9 (Fold Change) plotted as a function of group (NLC Sham, βARKnt Sham, NLC TAC, βARKnt TAC). FIG. 26C depicts TGFβ (Fold Change) plotted as a function of group (NLC Sham, βARKnt Sham, NLC TAC, βARKnt TAC). FIG. 26D depicts Osteopontin (Fold Change) plotted as a function of group (NLC Sham, βARKnt Sham, NLC TAC, βARKnt TAC). n=11 per group. P=0.001; *P<0.0001 by nonparametric one-way ANOVA with Dunns post-hoc test.

FIG. 27, comprising FIG. 27A depicts an immunoblot for phospho-Akt for the four groups (NLC Sham, βARKnt Sham, NLC TAC, βARKnt TAC). FIG. 27B depicts an immunoblot for total Akt for the four groups (NLC Sham, βARKnt Sham, NLC TAC, βARKnt TAC). FIG. 27C depicts the ratio of phospho-Akt to total Akt for the four groups (NLC Sham, βARKnt Sham, NLC TAC, (βARKnt TAC).

FIG. 28, comprising FIG. 28A through FIG. 28D, depicts results from example experiments demonstrating there is no difference in phospho and total IkB in βARKnt versus NLC mice 4 weeks post-TAC. FIG. 28A depicts the ratio of phospho-IkB to total IkB in the four groups (NLC Sham, βARKnt Sham, NLC TAC, βARKnt TAC). FIG. 28B depicts the ratio of phospho-IkB to GAPDH in the four groups (NLC Sham, βARKnt Sham, NLC TAC, βARKnt TAC). FIG. 28C depicts the ratio of IkB to GAPDH in the four groups (NLC Sham, βARKnt Sham, NLC TAC, βARKnt TAC). FIG. 28D depicts the ratio of phospho-IkB/IkB to GAPDH for the four groups (NLC Sham, βARKnt Sham, NLC TAC, βARKnt TAC).

FIG. 29, comprising FIG. 29A depicts the ratio of phospho-p65 to total p65 for the four groups (NLC Sham, βARKnt Sham, NLC TAC, βARKnt TAC). FIG. 29B depicts the ratio of phospho-p65 to GAPDH for the four groups (NLC Sham, βARKnt TAC). FIG. 29C depicts the ratio of p65 to GAPDH for the four groups (NLC Sham, βARKnt Sham, NLC TAC, βARKnt TAC). FIG. 29D depicts the ratio of phospho-p65/total p65 to GAPDH for the four groups (NLC Sham, βARKnt Sham, NLC TAC, βARKnt TAC).

FIG. 30, comprising FIG. 30A depicts the ratio of phospho-Akt to total Akt for the four groups (NLC Sham, βARKnt Sham, NLC TAC, βARKnt TAC). FIG. 30B depicts the ratio of phospho-Akt to GAPDH for the four groups (NLC Sham, βARKnt Sham, NLC TAC, βARKnt TAC). FIG. 30C depicts the ratio of Akt to GAPDH for the four groups (NLC Sham, βARKnt Sham, NLC TAC, βARKnt TAC). FIG. 30D depicts the ratio of phospho-Akt/total Akt to GAPDH for the four groups (NLC Sham, βARKnt Sham, NLC TAC, βARKnt TAC).

FIG. 31, comprising FIG. 31A depicts the ratio of phospho-GSK3β to total GSK3β for the four groups (NLC Sham, βARKnt Sham, NLC TAC, βARKnt TAC). FIG. 31B depicts the ratio of phospho-GSK3β to GAPDH for the four groups (NLC Sham, βARKnt Sham, NLC TAC, βARKnt TAC). FIG. 31C depicts the ratio of GSK3β to GAPDH for the four groups (NLC Sham, βARKnt Sham, NLC TAC, βARKnt TAC). FIG. 31D depicts the ratio of phospho-GSK3β/total GSK3β to GAPDH for the four groups (NLC Sham, βARKnt Sham, NLC TAC, βARKnt TAC).

FIG. 32 depicts the ratio of GRK2 to GAPDH for the four groups (NLC Sham, βARKnt Sham, NLC TAC, βARKnt TAC). Bottom panel: *P=0.01 by nonparametric one-way ANOVA with Dunns post-hoc test relative to NLC Sham. n=6 mice per group for signaling.

FIG. 33, comprising FIG. 33A depicts results from a gel electrophoresis experiment, showing AP2 levels for the four groups (NLC Sham, TG Sham, NLC TAC, TG TAC). FIG. 33B depicts the ratio of AP2 to GAPDH for the four groups (NLC Sham, βARKnt Sham, NLC TAC, βARKnt TAC).

FIG. 34, comprising FIG. 34A depicts results from a gel electrophoresis experiment, showing clathrin levels for the four groups (NLC Sham, TG Sham, NLC TAC, TG TAC). FIG. 34B depicts the ratio of clathrin to GAPDH for the four groups (NLC Sham, βARKnt Sham, NLC TAC, βARKnt TAC).

FIG. 35, comprising FIG. 35A depicts results from a gel electrophoresis experiment, showing caveolin 3 levels for the four groups (NLC Sham, TG Sham, NLC TAC, TG TAC). FIG. 35B depicts the ratio of caveolin 3 to GAPDH for the four groups (NLC Sham, TG Sham, NLC TAC, TG TAC).

FIG. 36, comprising FIG. 36A depicts systemic pressure for NLC and TgβARKnt groups. FIG. 36B depicts mean heart rate (bpm) as a function of isoproterenol (ng) dose for NLC and TgβARKnt groups. FIG. 36C depicts (+) dP/dt (mm Hg per second) as a function of isoproterenol (ng) dose for NLC and TgβARKnt groups. FIG. 36D depicts (−) dP/dt (mm Hg per second) as a function of isoproterenol (ng) dose for NLC and TgβARKnt groups. n=10 NLC, 9 TgβARKnt.

FIG. 37, comprising FIG. 37A through FIG. 37E, depicts results from example experiments demonstrating cardiomyocyte cross-sectional area is enhanced in TgβARKnt Sham mice, but not after TAC. Cross-sectional area was measured in NLC Sham (FIG. 37A), NLC TAC (FIG. 37B), βARKnt Sham (FIG. 37C), and βARKnt TAC (FIG. 37D), and quantified in a graph (FIG. 37E). ***, p<0.0001 by one-way ANOVA with Bonferroni post-hoc test relative to corresponding NLC Sham. n=5-10 hearts per group, 40 images per heart.

DETAILED DESCRIPTION

Figure 1A:
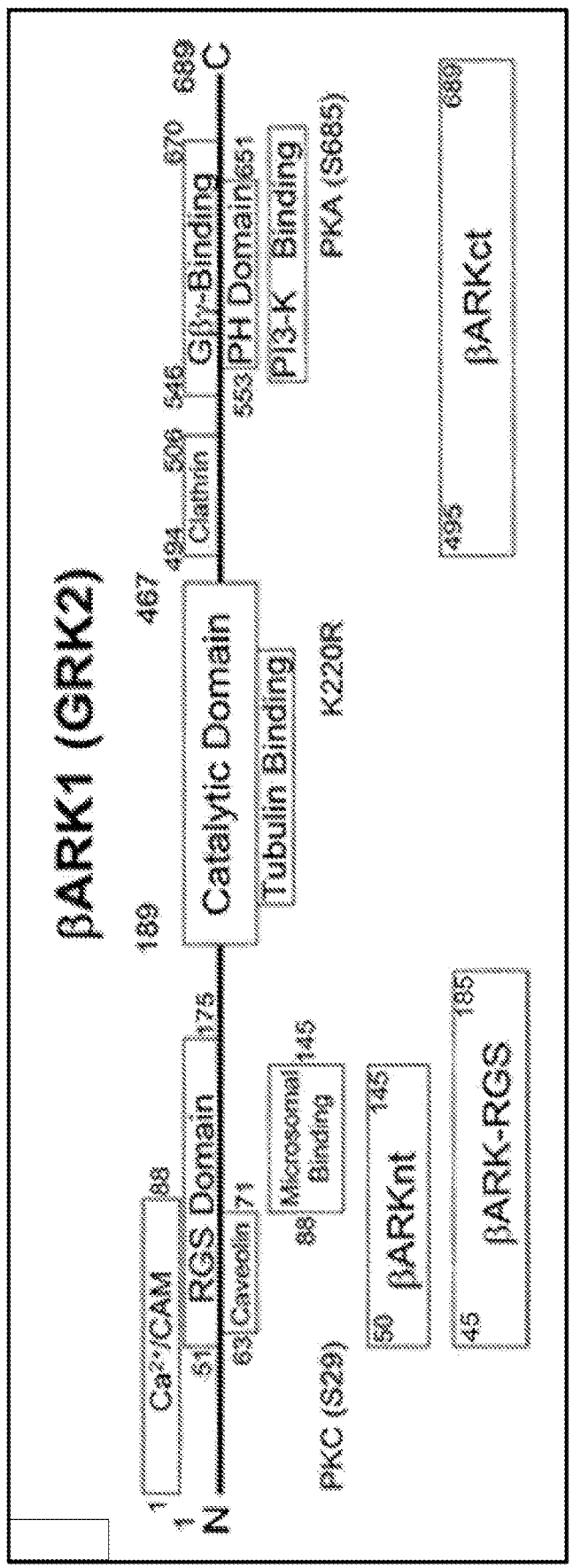
FIG. 1A and FIG. 1B, depicts that domain-specific interactions with the amino-terminus of GRK2 may reveal novel roles in cardiac signaling and function.
Figure 1B:
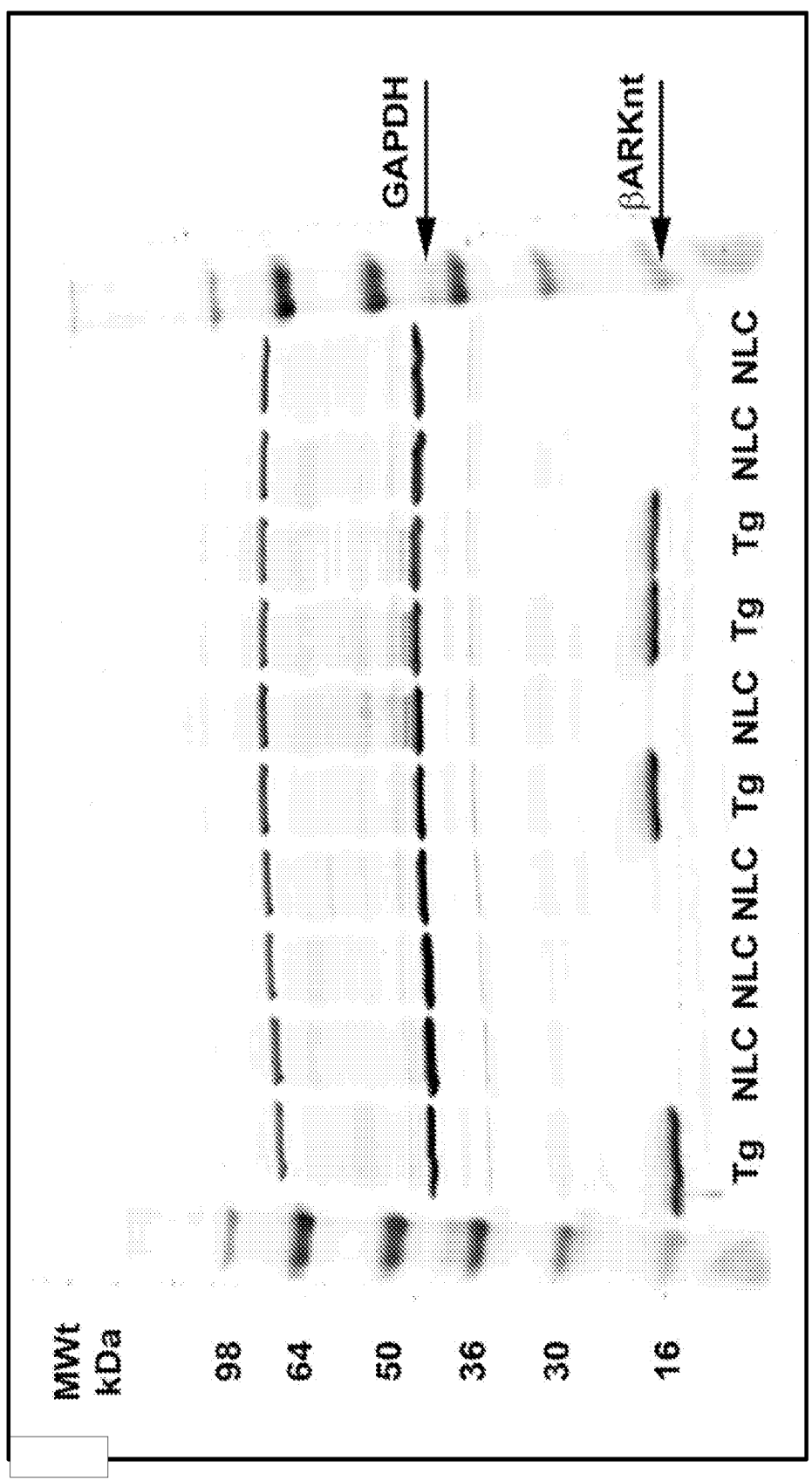
Figure 2A:
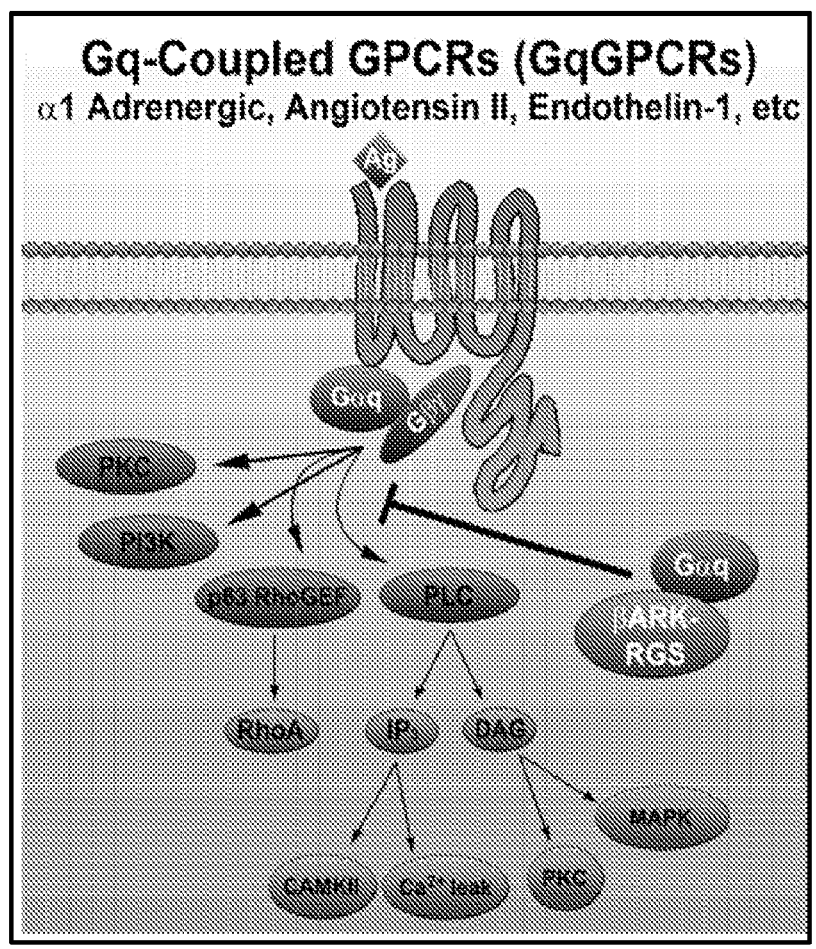
FIG. 2A and FIG. 2B, depicts a diagram and text outlining the experimental design utilized in example experiments.
Figure 2B:
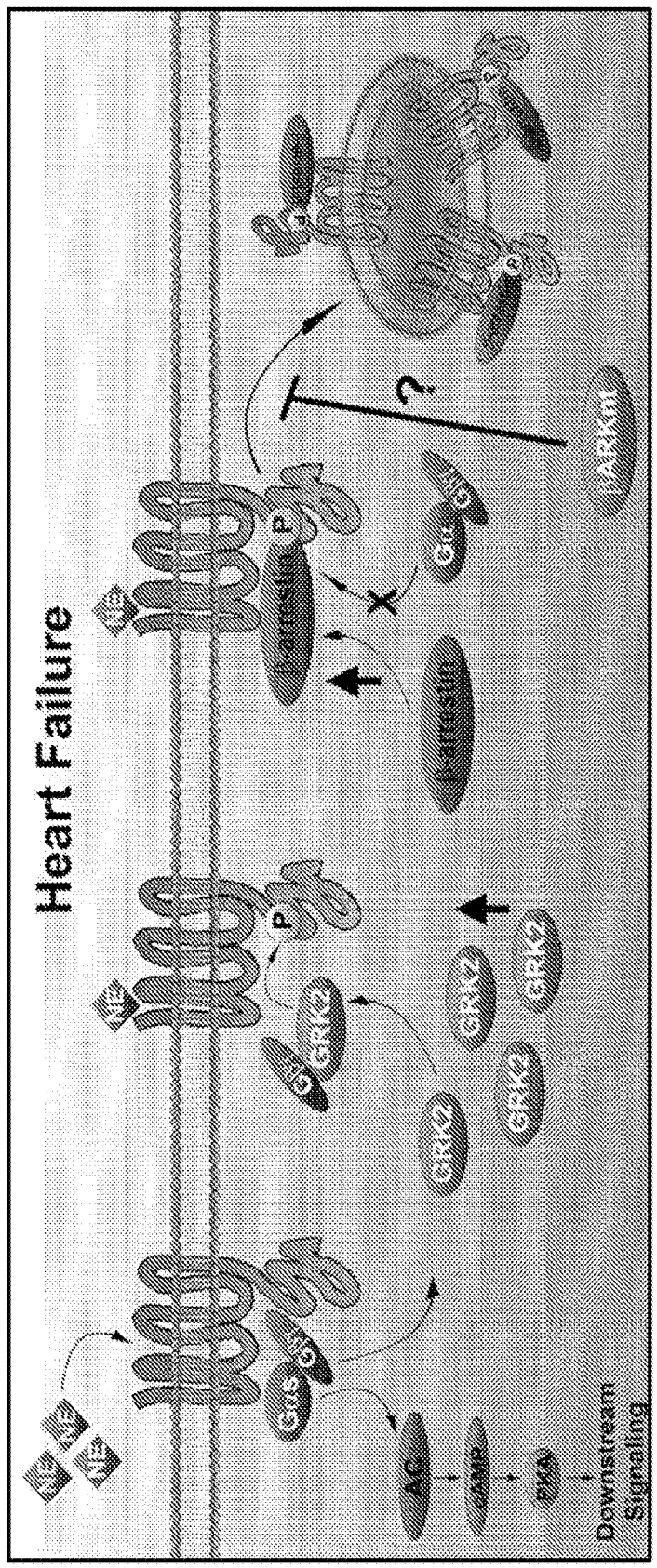

The present invention is based on the discovery of a novel peptide, βARKnt for the treatment or prevention of heart failure. βARKnt can be delivered as a peptide or as a nucleic acid. In some embodiments, a nucleic acid encoding βARKnt, a variant thereof or a fragment thereof is contained within an AAV vector. An AAV6 or AAV9 vector may be used for cardiac selective expression of the peptide following systemic injection.

Thus, the present invention provides compositions comprising a βARKnt peptide or a nucleic acid encoding a βARKnt peptide. In some embodiments, the nucleic acid encoding a βARKnt peptide is contained with in an AAV6 or AAV9 vector.

The present invention also provides methods for treating or preventing a cardiovascular disease or disorder, such as heart failure, in a subject in need thereof by administering a peptide, or nucleic acid of the invention or composition comprising a peptide, or nucleic acid of the invention to the subject. In some embodiments, the methods of the invention increase βAR density, thereby treating or preventing cardiovascular diseases and disorders.

The present invention also provides methods for altering βAR density, in a subject in need thereof by administering a peptide, or nucleic acid of the invention or composition comprising a peptide, or nucleic acid of the invention to the subject. In some embodiments, the methods of the invention increase βAR density.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In some embodiments, the patient, subject or individual is a mammal such as a non-primate (e.g., cows, pigs, horses, cats, dogs, rats, etc.) and a primate (e.g., monkey and human), most preferably a human. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, a "peptidomimetic" is a compound containing non-peptidic structural elements that is capable of mimicking the biological action of a parent peptide. A peptidomimetic may or may not comprise peptide bonds.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on the discovery that a fragment of the G protein-coupled receptor (GPCR) kinase (GRK) GRK2 terminal Regulator of G protein Signaling (RGS) domain (βARKnt) regulates β-adrenergic receptor (βAR) density and provides cardio-protection during pressure-overload induced heart failure (HF).

Thus, the present invention provides compositions comprising a βARKnt peptide or a nucleic acid encoding a βARKnt peptide. In some embodiments, the nucleic acid encoding a βARKnt peptide is contained with in an AAV6 or AAV9 vector.

The present invention also provides methods for treating or preventing a cardiovascular disease or disorder, such as heart failure, in a subject in need thereof by administering a βARKnt peptide or a nucleic acid encoding a βARKnt peptide or composition comprising a βARKnt peptide or a nucleic acid encoding a βARKnt peptide to the subject. In some embodiments, the methods of the invention increase βAR density, thereby treating or preventing cardiovascular diseases and disorders.

The present invention also provides methods for altering βAR density, in a subject in need thereof by administering a βARKnt peptide or a nucleic acid encoding a βARKnt peptide or composition comprising a βARKnt peptide or a nucleic acid encoding a βARKnt peptide to the subject. In some embodiments, the methods of the invention increase βAR density.

Peptides

In one aspect, the present invention provides isolated peptides and compositions for treating heart failure. For example, in certain instances the compositions improve regulate βAR density. In some instances, the compositions increase βAR density and prevent progression to HF.

In one embodiment, the composition comprises isolated peptides derived from the GRK2-RGS domain. In one embodiment, the composition comprises a βARKnt peptide, or a derivative or fragment thereof. In one embodiment, the isolated peptide comprises an amino acid sequence of RGEVTFEKIFSQKLGYLLFRDFCLKHLEEAKPLVEFY-EEIKKYEKLETEEERLVCS REIFDTYIMKELLACSH-PFSKSAIEHVQGHLVKKQVPPDL (SEQ ID NO:1), a derivative thereof or a fragment thereof.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a peptide having substantial homology to SEQ ID NO: 1. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to SEQ ID NO: 1.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the βARKnt peptide.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising a βARKnt peptide fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., bone, regenerating bone, degenerating bone, cartilage). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain a peptide comprising a βARKnt peptide fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Mimetics

In one embodiment, the present invention provides a βARKnt peptidomimetics. Peptidomimetics are compounds based on, or derived from, peptides and proteins. The peptidomimetics of the present invention typically can be obtained by structural modification of a βARKnt peptide using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptide.

Moreover, as is apparent from the present disclosure, mimetopes of the subject βARKnt peptide can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Nataraj an et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p 134). Also, see generally, Session III: Analytic and synthetic methods, in in Peptides: Chemistry and Biology, G. R. Marshall ed., ESCOM Publisher: Leiden, Netherlands, 1988)

In addition to a variety of side chain replacements which can be carried out to generate the peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the βARKnt peptide. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

In one embodiment, the βARKnt mimetic is a small molecule. When the βARKnt mimetic is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule βARKnt mimetic of the invention comprises an organic molecule, inorganic molecule, biomolecule, synthetic molecule, and the like.

Nucleic Acids

In one embodiment, the present invention provides a composition comprising an isolated nucleic acid encoding a βARKnt peptide, a fragment thereof or a derivative thereof. For example, in one embodiment, the composition comprises an isolated nucleic acid encoding SEQ ID NO:1, or a variant or fragment thereof.

Further, the invention encompasses an isolated nucleic acid encoding a peptide having substantial homology to SEQ ID NO:1. In certain embodiments, the isolated nucleic acid sequence encodes a peptide having at least 75%, 80%, 85%, 90%, 95%, 96%, 97%, 98%, or 99% sequence homology with SEQ ID NO:1.

The isolated nucleic acid sequence encoding a βARKnt peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a βARKnt peptide, or functional variant thereof. In one embodiment, the composition comprises an isolated RNA molecule encoding a βARKnt peptide, or a functional variant thereof.

The nucleic acid molecules of the present invention can be modified to improve stability in serum or in growth medium for cell cultures. Modifications can be added to enhance stability, functionality, and/or specificity and to minimize immuno-stimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a βARKnt peptide is typically achieved by operably linking a nucleic acid encoding a βARKnt peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a βARKnt peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. 2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Adeno-Associated Virus Vectors

Adeno-associated virus (AAV) is a unique, non-pathogenic member of the Parvoviridae family of small, non-enveloped, single-stranded DNA animal viruses. AAV require helper virus (e.g., adenovirus) for replication and, thus, do not replicate upon administration to a subject. AAV can infect a relatively wide range of cell types and stimulate only a mild immune response, particularly as compared to a number of other viruses, such as adenovirus. Over 100 AAV isolates have been reported. Biochemical and molecular characterization of many suggests that some exhibit different tissue tropism, persistence, and transduction efficiency (see, for example, Kwon et al., ibid.). Examples of AAV include AAV1, AAV2, AAV3, AAV4, AAV5, AAV6, AAV7, AAV8, AAV9, AAV10, AAV11, and AAV12, which appear to be of simian or human origin. AAV have also been found in other animals, including birds (e.g., avian AAV, or AAAV), bovines (e.g., bovine AAV, or BAAV), canines, equines, ovines, and porcines.

Vectors and virions based upon AAV have advanced to the forefront of gene therapy, due to their ability to achieve long-term transgene expression in vivo and low immunogenicity (see, for example, Halbert et al., 2000, J Virol 74, 1524-1532; Sumner-Jones et al., ibid.; Stieger et al., ibid.; Niemeyer et al., ibid.). AAV virions have hitherto not been associated with any malignant disease. Furthermore, all viral protein genes can be deleted from AAV vectors and AAV virions contributing to their safety profile (see, for example, Daya et al., ibid.). Several Phase I/II clinical trials support a good overall safety profile for AAV virions and little associated toxicity in humans (see, for example, Moss et al., ibid.; Mandel et al., ibid., Diaz-Nido et al., ibid., Simonelli et al., ibid; Bainbridge et al., ibid.).

An AAV vector is a recombinant nucleic acid molecule in which at least a portion of the AAV genome is replaced by a heterologous nucleic acid molecule. It is possible to replace about 4.7 kilobases (kb) of AAV genome DNA, e.g., by removing the viral replication and capsid genes. Often the heterologous nucleic acid molecule is simply flanked by AAV inverted terminal repeats (ITRs) on each terminus. The ITRs serve as origins of replication and contain cis acting elements required for rescue, integration, excision from cloning vectors, and packaging. Such vectors typically also include a promoter operatively linked to the heterologous nucleic acid molecule to control expression.

An AAV vector can be packaged into an AAV capsid in vitro with the assistance of a helper virus or helper functions expressed in cells to yield an AAV virion. The serotype and cell tropism of an AAV virion are conferred by the nature of the viral capsid proteins.

AAV vectors and AAV virions have been shown to transduce cells efficiently, including both dividing and non-dividing cells (see, for example, Lai et al., 2002, DNA Cell Biol 21, 895-913). Among AAVs, serotype 5 (AAV5) has demonstrated enhanced gene transfer activity in lung, eye and central nervous system (CNS) as well as rodent salivary glands (see, for example, Katano et al., ibid.). AAV vectors and virions have been shown to be safe and to lead to long term in vivo persistence and expression in a variety of cell types.

As used herein, an AAV vector that encodes an βARKnt peptide is a nucleic acid molecule that comprises a nucleic acid molecule that encodes an βARKnt peptide of the invention, an ITR joined to 5' terminus of the βARKnt encoding nucleic acid molecule, and an ITR joined to the 3' terminus of the βARKnt encoding nucleic acid molecule. Examples of ITRs include, but are not limited to, AAV1, AAV2, AAV3, AAV4, AAV5, AAV6, AAV7, AAV8, AAV9, AAV10, AAV11, AAV12, AAAV, BAAV, and other AAV ITRs known to those skilled in the art. In one embodiment, an AAV ITR is selected from an AAV2 ITR, an AAV5 ITR, an AAV6 ITR, and a BAAV ITR. In one embodiment, an AAV ITR is an AAV2 ITR. In one embodiment, an AAV ITR is an AAV5 ITR. In one embodiment, an AAV ITR is an AAV6 ITR. In one embodiment, an AAV ITR is a BAAV ITR.

An AAV vector of the embodiments can also include other sequences, such as expression control sequences. Examples of expression control sequences include, but are not limited to, a promoter, an enhancer, a repressor, a ribosome binding site, an RNA splice site, a polyadenylation site, a transcriptional terminator sequence, and a microRNA binding site. Examples of promoters include, but are not limited to, an AAV promoter, such as a p5, p19 or p40 promoters, an adenovirus promoter, such as an adenoviral major later promoter, a cytomegalovirus (CMV) promoter, a papilloma virus promoter, a polyoma virus promoter, a respiratory syncytial virus (RSV) promoter, a sarcoma virus promoter, an SV40 promoter other viral promoters, an actin promoter, an amylase promoter, an immunoglobulin promoter, a kallikrein promoter, a metallothionein promoter, a heat shock promoter, an endogenous promoter, a promoter regulated by rapamycin or other small molecules, other cellular promoters, and other promoters known to those skilled in the art. In one embodiment, the promoter is an AAV promoter. In one embodiment, the promoter is a CMV promoter. Selection of expression control sequences to include can be accomplished by one skilled in the art.

The disclosure provides AAV vectors of different serotypes (as determined by the serotype of the ITRs within such vector) that encode an βARKnt peptide. Such an AAV vector can be selected from an AAV1 vector, an AAV2 vector, an AAV3 vector, an AAV4 vector, an AAV5 vector, an AAV6 vector, an AAV7 vector, an AAV8 vector, an AAV9 vector, an AAV10 vector, an AAV11 vector, an AAV12 vector, an AAAV vector, and a BAAV vector, and other AAV vectors known to those skilled in the art, wherein any of such vectors encode an βARKnt peptide. One embodiment is an AAV2 vector, an AAV5 vector, an AAV6 vector or a BAAV vector, wherein the respective vector encodes an βARKnt peptide. One embodiment is an AAV2 vector that encodes an βARKnt peptide. One embodiment is an AAV5 vector that encodes an βARKnt peptide. One embodiment is an AAV6 vector that encodes an βARKnt peptide. One embodiment is a BAAV vector that encodes an βARKnt peptide.

One embodiment is an AAV vector that comprises AAV ITRs and a CMV promoter operatively linked to a nucleic acid molecule encoding a βARKnt peptide. One embodiment is an AAV5 vector that comprises AAV5 ITRs and a CMV promoter operatively linked to a nucleic acid molecule encoding βARKnt peptide.

In one embodiment, the AAV vector provides cardio-specific expression of the encoded βARKnt peptide. In one embodiment, the EF1alpha promoter comprises mir122. In one embodiment, the AAV vector is an AAV serotype 6 vector. In one embodiment, the AAV vector is an AAV serotype 9 vector. In one embodiment, the AAV vector comprises a cardiac-specific promoter operably linked to the nucleic acid sequence encoding the βARKnt peptide. For example, in one embodiment, the AAV vector comprises an alpha cardiac actin enhancer. In one embodiment, the AAV vector comprises an EF1alpha promoter. In one embodiment the AAV vector comprises a nucleic acid that reduces liver retention. For example, in one embodiment, the AAV vector comprises a nucleic acid encoding mir122. In one embodiment, the EF1alpha promoter comprises mir122. In one embodiment, mir122 comprises the nucleic acid sequence of CCTTAGCAGAGCTGTGGAGTGTGACAATGGTGTTT-GTGTCTAAACTATCAAAC GCCATTATCA-CACTAAATAGCTACTGCTAGGC (SEQ ID NO:2), or a functional equivalent sequence having at least 80%, more preferably 90%, 95%, 96%, 97%, 98%, 99%, sequence identity thereto.

Treatment Methods

The present invention provides a method for the treatment or prevention of a cardiovascular disease or disorder, or a condition associated with a cardiovascular disease or disorder, in a subject in need thereof. The present invention also provides a method for altering the β-adrenergic receptor (βAR) density, in a subject in need thereof. For example, chronic βAR agonist administration may downregulate the density of βAR. Accordingly, in one embodiment, the method comprises increasing βAR density in a patient with decreased βAR density.

Exemplary conditions treated or prevented by way of the present invention include, but are not limited to, heart failure and cardiac infarction, stroke, hypertension, and diseases associated with altered vascular or other smooth muscle responsiveness. In one embodiment, the condition is heart failure. In one embodiment, the methods of the invention prevent or treat a disease or disorder associated with cardiac or vascular dysfunction. For example, in one embodiment, the methods of the invention prevent or treat diabetes.

In one embodiment, the invention comprises a method of treating or preventing a cardiovascular disease or disorder. In one embodiment, the invention comprises a method of treating or preventing heart failure. In one embodiment, the method comprises administering an effective amount of a peptide or nucleic acid described herein to a subject diagnosed with, suspected of having, or at risk for a cardiovascular disease or disorder. Thus, the present invention relates to the prevention and treatment of a disease or disorder by administration of a therapeutically effective amount of a βARKnt peptide, a composition comprising said peptide, a nucleic acid encoding a βARKnt peptide, or a composition comprising a nucleic acid encoding a βARKnt peptide to a subject in need thereof, for the treatment or prevention of a cardiovascular disease or disorder, including but not limited to heart failure.

The following are non-limiting examples of cardiovascular diseases that can be treated by the disclosed methods and compositions: arterial cardiovascular thromboembolic disorders, venous cardiovascular thromboembolic disorders, and thromboembolic disorders in the chambers of the heart; ahtherosclerosis; restensosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); first or recurrent myocardial infarction; acute myocardial infarction (AMI); myocardial infarction; non-Q wave myocardial infarction; non-STE myocardial infarction; coronary artery disease; cardiac ischemia; ischemia; ischemic sudden death;

transient ischemic attack; stroke; atherosclerosis; peripheral occlusive arterial disease; venous thrombosis; deep vein thrombosis; thrombophlebitis; arterial embolism; coronary arterial thrombosis; cerebral arterial thrombosis; cerebral embolism; kidney embolism; pulmonary embolism; thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis; thrombosis resulting from atherosclerosis, surgery or surgical complications, prolonged immobilization, arterial fibrillation, congenital thrombophilia, cancer, diabetes, effects of medications or hormones, and complications of pregnancy; cardiac arrhythmias including supraventricular arrhythmias, atrial arrhythmias, atrial flutter, and atrial fibrillation.

In one embodiment, the invention comprises a method of altering βAR density, in a subject in need thereof. In one embodiment, the invention provides a method of increasing βAR density, in a subject in need thereof. In one embodiment, the method comprises administering an effective amount of a peptide or nucleic acid described herein to a subject diagnosed with, suspected of having, or at risk for a downregulated βAR density. Thus, the present invention relates to the prevention and treatment of decreased βAR density by administration of a therapeutically effective amount of a βARKnt peptide, a composition comprising said peptide, a nucleic acid encoding a βARKnt peptide, or a composition comprising a nucleic acid encoding a βARKnt peptide to a subject in need thereof, to increase βAR density.

In one embodiment, the subject has low βAR density. For example, chronic βAR agonist administration may downregulate the density of βAR. Accordingly, in one embodiment, the subject has taken a βAR agonist. In one embodiment, the method comprises administering a comprises administering an effective amount of a peptide or nucleic acid described herein with a second therapeutic. In one embodiment, the second therapeutic is a βAR agonist.

Exemplary βAR agonist include, but are not limited to, selected from isoproterenol, metaproterenol, formoterol, salmeterol, salbutamol, albuterol, terbutaline, fenoterol, and vilanterol.

In one embodiment, the method comprises administering to the subject a AAV vector comprising a nucleic acid encoding a βARKnt peptide. In some embodiments, the AAV vector is a serotype 6 or serotype 9 AAV. In one embodiment, the AAV vector comprises a comprises an alpha cardiac actin enhancer. In one embodiment, the AAV vector comprises an EF1alpha promoter. In one embodiment the AAV vector comprises a nucleic acid that reduces liver retention. For example, in one embodiment, the AAV vector comprises a nucleic acid encoding mir122. In one embodiment, the EF1alpha promoter comprises mir122.

Subjects to which administration of a peptide, nucleic acid or composition of the invention is contemplated include, but are not limited to, humans and other primates, mammals including commercially relevant mammals such as non-human primates, cattle, pigs, horses, sheep, cats, and dogs.

The peptide, nucleic acid or composition of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the peptide or the composition may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

Methods of treatment of the diseases encompassed by the invention can comprise the transplantation of single cells, cell lines, compositions, or cell populations of the invention into a subject in need thereof. In certain embodiments, the subject is a human.

Pharmaceutical Composition and Administration

The peptides, nucleic acids and compositions of the invention can be formulated and administered to a subject. For example, a βARKnt peptide or nucleic acids encoding a βARKnt peptide can be formulated and administered to a subject for the treatment and/or prevention of a disease or disorder.

The present invention also provides pharmaceutical compositions comprising one or more of the compositions described herein. In some aspects, the invention encompasses the preparation and use of pharmaceutical compositions comprising a βARKnt peptide or nucleic acid encoding a βARKnt peptide as an active ingredient for the treatment or prevention of a disease or disorder, including but not limited to, diabetes. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the HMW-HA or other composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, mulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, subcutaneous, intramuscular, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Typically dosages of the compound of the invention which may be administered to an animal, preferably a human, range in amount from about 0.01 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 1 mg to about 100 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Domain-Specific Interactions with the Amino-Terminus of GRK2 may Reveal Novel Roles in Cardiac Signaling and Function During heart failure (HF), cardiac levels and activity of the G protein-coupled receptor (GPCR) kinase (GRK) GRK2 are elevated and contribute to adverse remodeling and contractile dysfunction, while inhibition via a carboxyl-terminal peptide, βARKct, enhances heart function and can prevent HF development. Mounting evidence supports the idea of a dynamic "interactome" in which GRK2 can uncouple GPCRs via novel protein-protein interactions. Several GRK2 interacting partners are important for adaptive and maladaptive myocyte growth; therefore, an understanding of domain-specific interactions with signaling and regulatory molecules could lead to novel targets for HF therapy. For instance, GRK2 contains a putative amino-terminal Regulator of G protein Signaling (RGS) domain (βARK-RGS) that directly interacts with Gq and appears to inhibit signaling without altering Gq enzymatic activity. Cardiac-specific transgenic (Tg) expression of a fragment of this RGS domain (βARKnt) did not alter acute hypertrophy after pressure overload or demonstrate RGS activity in vivo against Gq-mediated signaling. In contrast, βARKnt induced hypertrophy and elevated β-adrenergic receptor (βAR) density without altering agonist-induced contractility or adenylyl cyclase activity, due to a compensatory increase in GRK2 activity. Importantly, though, βAR downregulation in response to chronic agonist administration was attenuated by βARKnt expression, indicating a novel regulation of βAR receptor density. Given these findings we have recently investigated the effect of βARKnt expression during chronic pressure overload post trans-aortic constriction (TAC). Echocardiographic analysis revealed increased posterior wall thickness and left-ventricular mass 4 weeks post-TAC compared to non-transgenic littermate controls (NLC). Importantly, despite enhanced hypertrophy, the progression to HF was inhibited in βARKnt mice 14 weeks post-TAC (% LV Ejection Fraction of 36.1±0.2 in NLC versus 56.6±0.9 in Tg mice). Histological analysis of interstitial fibrosis and cross-sectional areas determines any alterations in maladaptive remodeling. Further, cardiomyocyte signaling and βARKnt protein-binding partners are important as these data indicate that βARKnt-mediated regulation of βAR density may provide a novel means of cardioprotection during pressure-overload induced HF. Further, AAV6- and AAV9-βARKnt constructs are developed for cardiac selective expression of the peptide following systemic injection. This would all for the definition of the dose range capable of preventing the progression of cardiovascular injury and the therapeutic window of when during disease progression this therapeutic intervention can be administered and maintain a beneficial effect. The adeno-associated viral vector of serotypes 6 and 9 are expressed under an alpha cardiac actin enhancer and EF1alpha promoter containing mir122 inserts that reduce liver retention. This construct allows the virus to be injected systemically through intravenous injection yet be predominantly expressed in the myocardium. This system allows delivery of the virus at any time point prior to or after disease development to investigate the disease states that are positively affected by βARKnt expression. Further, this method of delivery facilitates a detailed determination of the dose-response relationship to determine the optimal dose range for patient therapy. This is particularly important given the vast array of cardiovascular disease etiologies and contributing factors including lifestyle and medical history, wherein intravenous viral delivery could be titrated up to each patient's individual effective dose.

Example 2: βARKnt Mice Exhibit an Improved Response in an Experimental Model of Heart Failure With approximately 550,000 new cases of heart failure (HF) diagnosed in the U.S. alone each year this disease represents a growing healthcare concern. Importantly, despite substantial improvements in its management, including improved mechanical and pharmacotherapy, outcomes in HF remain poor. Thus, there is an urgent need to develop new therapeutic strategies, including cell and gene-based therapies, and recent research has been aimed at the underlying mechanisms of HF progression. Developing new approaches to HF therapy has included development and characterization of transgenic animals with αMHC promoter driven expression of the cDNA that encodes bovine GRK2 residues 50-145 (βARKnt) with a carboxy-terminal flag-tag. In this model, proof-of-concept has been demonstrated for inhibiting decompensation to HF in a murine model of trans-aortic constriction-mediated chronic pressure overload hypertrophy and heart failure in transgenic animals with continuous expression of the peptide beginning with post-natal activation of the promoter. While this is an in vivo beneficial effect, a limitation of this invention was that it did not allow thorough investigation into whether βARKnt can reverse or attenuate established left-ventricular remodeling in various disease models, but is limited to prophylactic or protective applications.

Importantly, current pharmacotherapy targeting the sympathetic overdrive and GRK2-mediated decrease in βAR signaling and density uses β-blocking agents to shield the receptors from agonist binding. This remains the first line of defense in the heart and a standard of care for HF patients. The present data indicate that the βARKnt peptide enhances βAR signaling by a different mechanism wherein it restores βAR density and signaling in the presence of enhanced GRK2 activity, potentially by facilitating internalization and recycling of agonist bound receptors. This process of internalization and recycling restores the βAR receptors to the membrane where they may again be bound by agonist for signaling, and preserves them from the degradation pathway. Thus, rather than shielding the heart from overstimulation, the present invention enhances its natural ability to manage the stimulation and regulate it in a sustainable manner. Further, the ability to target cardiovascular expression via the tropism of the AAV6- and AAV9-βARKnt constructs can provide a significant advance over a main limitation of β-blocker therapy by removing the side-effects resulting from inhibition of βAR signaling in other tissues throughout the body.

Therefore, the present invention includes the development of adeno-associated viral vectors that can be utilized as gene therapy agents, and the development of a small molecule mimic of the peptide is being performed, both of which can allow study of the protective effects of βARKnt in large animals models of disease. Furthermore, these new compounds can allow thorough investigation into whether βARKnt can reverse or attenuate established left-ventricular remodeling in various disease models. The AAV6- and AAV9-βARKnt constructs would provide the means necessary to achieve effective gene delivery of βARKnt to its desired site of action, the heart, in animals and eventually in humans.

The invention comprises an adeno-associated viral vector of serotypes 6 and 9 expressed under an alpha cardiac actin enhancer and EF1alpha promoter comprising mir122 inserts that reduce liver retention. This construct allows the virus to be injected systemically through intravenous injection yet be predominantly expressed in the myocardium. This system allows delivery of the virus at any time point prior to or after disease development to investigate the disease states that are positively affected by βARKnt expression. Further, this method of delivery facilitates a detailed determination of the dose-response relationship to determine the optimal dose range for patient therapy. This is particularly important given the vast array of cardiovascular disease etiologies and contributing factors including lifestyle and medical history, wherein intravenous viral delivery could be titrated up to each patients individual effective dose.

Introduction

There is no cure for heart failure (HF) except cardiac transplantation, and that can only occur in ~3,000 patients worldwide. This is significant because HF currently affects more than 5 million Americans and contributes to 300,000 deaths per year, a rising number due to increased survival rates post-myocardial infarction (MI). While MI is the major cause of HF, several other co-morbid conditions, including chronic hypertension or ischemic and valvular heart disease, can reduce myocardial efficiency and ultimately lead to HF. The present data demonstrate that a peptide can prevent decompensation to HF in a murine model of pressure overload-induced hypertrophy and HF despite significant left-ventricular remodeling. This peptide is unique to the present invention of AAV6- and AAV9-βARKnt constructs, which can allow the investigation of dosing, timing of administration during disease progression, and side effect profiles in multiple disease models representing the various etiologies that cause human HF.

During heart failure (HF), cardiac levels and activity of the G protein-coupled receptor (GPCR) kinase (GRK) GRK2 are elevated and contribute to adverse remodeling and contractile dysfunction, while inhibition via a carboxyl-terminal peptide, βARKct, enhances heart function and can prevent HF development. Mounting evidence supports the idea of a dynamic "interactome" in which GRK2 can uncouple GPCRs via novel protein-protein interactions. Several GRK2 interacting partners are important for adaptive and maladaptive myocyte growth; therefore, an understanding of domain-specific interactions with signaling and regulatory molecules can lead to novel targets for HF therapy. For instance, GRK2 has a putative amino-terminal Regulator of G protein Signaling (RGS) domain (βARK-RGS) that directly interacts with Gq and appears to inhibit signaling without altering Gq enzymatic activity. Previously, cardiac-specific transgenic (Tg) expression of a fragment of this RGS domain (βARKnt) was investigated. This fragment did not alter acute hypertrophy after pressure overload or demonstrate RGS activity in vivo against Gq-mediated signaling. In contrast, βARKnt induced hypertrophy and elevated β-adrenergic receptor (βAR) density without altering agonist-induced contractility or adenylyl cyclase activity, due to a compensatory increase in GRK2 activity. Importantly, though, βAR downregulation in response to chronic agonist administration was attenuated by βARKnt expression, indicating a novel regulation of βAR receptor density. Given these findings the effect of βARKnt expression during chronic pressure overload post trans-aortic constriction (TAC) has been investigated. Echocardiographic analysis revealed increased posterior wall thickness and left-ventricular mass 4 weeks post-TAC compared to non-transgenic littermate controls (NLC). Importantly, despite enhanced hypertrophy, the progression to HF was inhibited in βARKnt mice 14 weeks post-TAC (% LV Ejection Fraction of 36.1±0.2 in NLC versus 56.6±0.9 in Tg mice). These data indicate that βARKnt-mediated regulation of βAR density may provide a novel means of cardioprotection during pressure-overload induced HF. (Schumacher, S M et al., 2015, Circulation Research, 117:A365).

GRK2 comprises a putative amino-terminal Regulator of G protein Signaling (RGS) domain (βARKrgs) that directly interacts with Gq and appears to inhibit signaling without altering Gq enzymatic activity. It is presently demonstrated that cardiac-specific transgenic (Tg) expression of both the RGS domain of GRK2 and a shorter N-terminal peptide (βARKnt) can alter cardiac physiology when expressed in myocytes. Of note, they both halt HF progression in mice after pressure overload but have differential effects on the initial hypertrophic response.

Previously, it was demonstrated that cardiac expression of the βARKnt peptide did not alter acute hypertrophy 7 days after pressure overload or demonstrate RGS activity in vivo against Gq-mediated signaling. In contrast, βARKnt induced hypertrophy and elevated β-adrenergic receptor (βAR) density without altering agonist-induced contractility or adenylyl cyclase activity, due to a compensatory increase in GRK2 activity. Importantly, though, βAR downregulation in response to 7 days of agonist administration was attenuated by βARKnt expression, indicating a novel regulation of βAR receptor density by an unknown mechanism. Unfortunately, this original line was lost before the mechanism could be investigated. A new variation of this line has therefore been generated. While the baseline phenotype was milder (no significant increase in βAR density) the effect of βARKnt expression during chronic pressure overload after transaortic constriction (TAC) was investigated. Echocardiographic analysis revealed increased posterior wall thickness and left ventricular mass 4 weeks post-TAC compared to non-transgenic littermate controls (NLC). Importantly, despite enhanced hypertrophy, the progression to HF was inhibited in βARKnt mice 14 weeks post-TAC (% LV Ejection Fraction of 34.8±3.2 in NLC versus 57.3±0.65 in Tg mice). These data indicate that βARKnt-mediated regulation of βAR density may provide a novel means of cardioprotection during pressure-overload induced HF.

Based on these data, AAV6- and AAV9-βARKnt constructs for cardiac selective expression of the peptide following systemic injection can be used for HF therapy. This would allow one to define the dose range capable of preventing the progression of cardiovascular injury and the therapeutic window of when during disease progression this therapeutic intervention can be administered and maintain a beneficial effect.

Systemic injection of AAV6- or AAV9-βARKnt as a therapeutic intervention in patients is envisioned, with chronic hypertension or vascular disease prior to or during the deterioration of cardiovascular function to prevent decompensation to HF. Projected doses for large animal studies are as follows: Cohort 1: $7.5 \times 10^{11}$ vg per subject (~$1 \times 10^{10}$ vg/kg); Cohort 2: $3.75 \times 10^{12}$ vg per subject (~$5 \times 10^{10}$ vg/kg); Cohort 3: $7.5 \times 10^{12}$ vg per subject (~$1 \times 10^{11}$ vg/kg); Cohort 4: $3.75 \times 10^{13}$ vg per subject (~$5 \times 10^{11}$ vg/kg). Two lower doses are included because no data are available on the efficacy of βARKnt in humans, whereas Cohorts 3 and 4 are in the range where it is expected to see some efficacy and are at or near what has been delivered through the coronary arteries to human HF patients in other trials. In fact, the dose of AAV-SERCA2a in the CUPID Trial that appeared to have some efficacy was the highest dose ($1 \times 10^{13}$ vg), so the planned Cohort 3 is just short of this and Cohort 4 is above so there should be sufficient dose coverage to potentially see some efficacy and certainly, the doses will cover the range needed for seeing any adverse events.

Results

During initial characterization of the βARKnt line, cardiovascular function and adrenergic responsiveness were analyzed via terminal hemodynamics at baseline and upon challenge with increasing doses of the β-adrenergic receptor agonist isoproterenol (ISO) in Tg and NLC mice. No difference was observed in mean systemic pressure, the heart rate (HR) response to isoproterenol, or cardiac contractility and relaxation (dP/dt maximum and minimum) at baseline or in response to ISO, demonstrating that cardiac function and βAR responsiveness were not altered in the transgenic animals (FIG. 36).

Figure 3A:
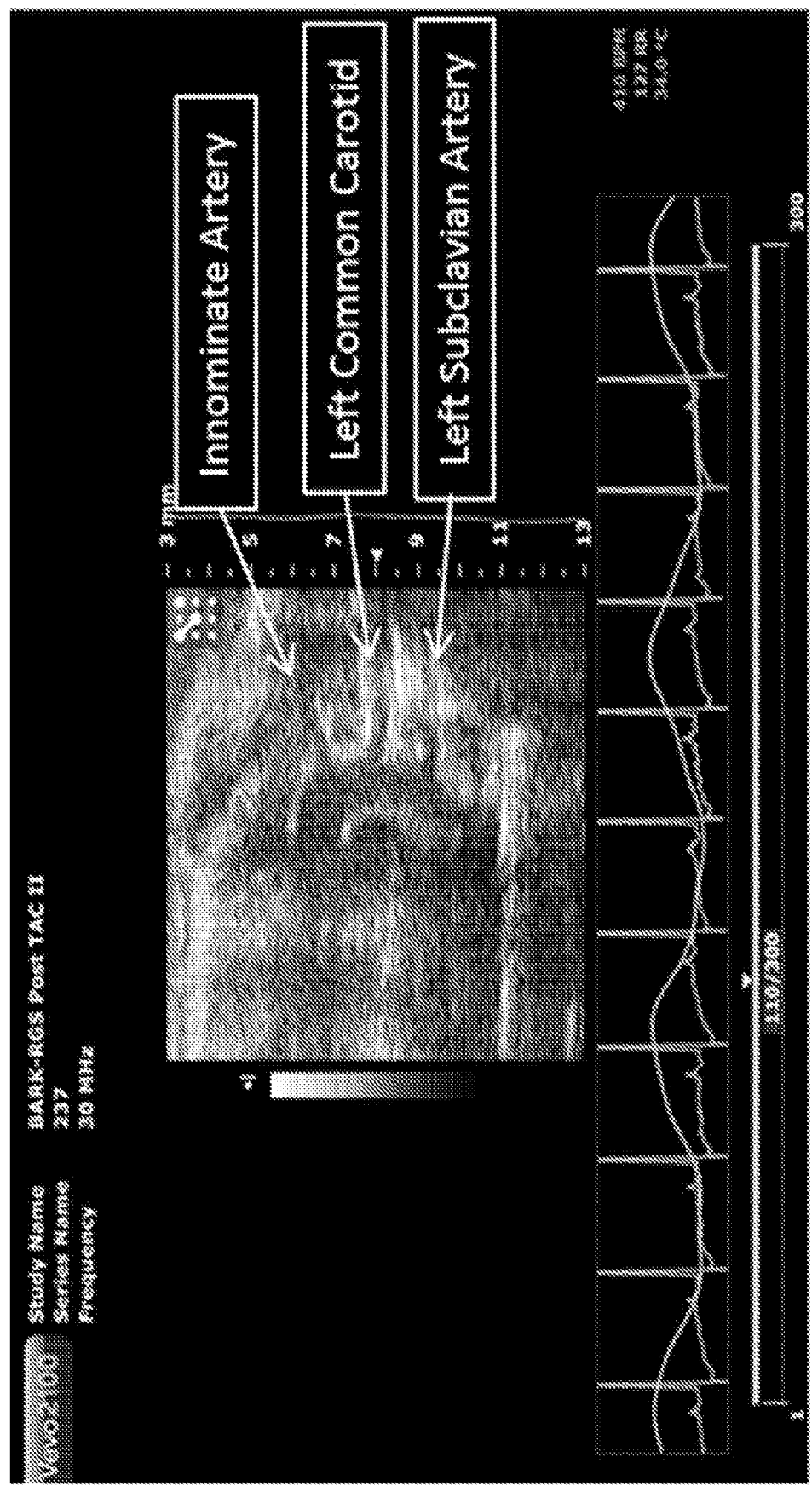
FIG. 3A through FIG. 3C, depicts a mouse model of cardiac pressure overload using transaortic constriction (TAC). ***, P<0.0001 by two-way ANOVA with Bonferroni post-hoc test relative to NLC Sham. n=7-26 mice per group.
Figure 3B:
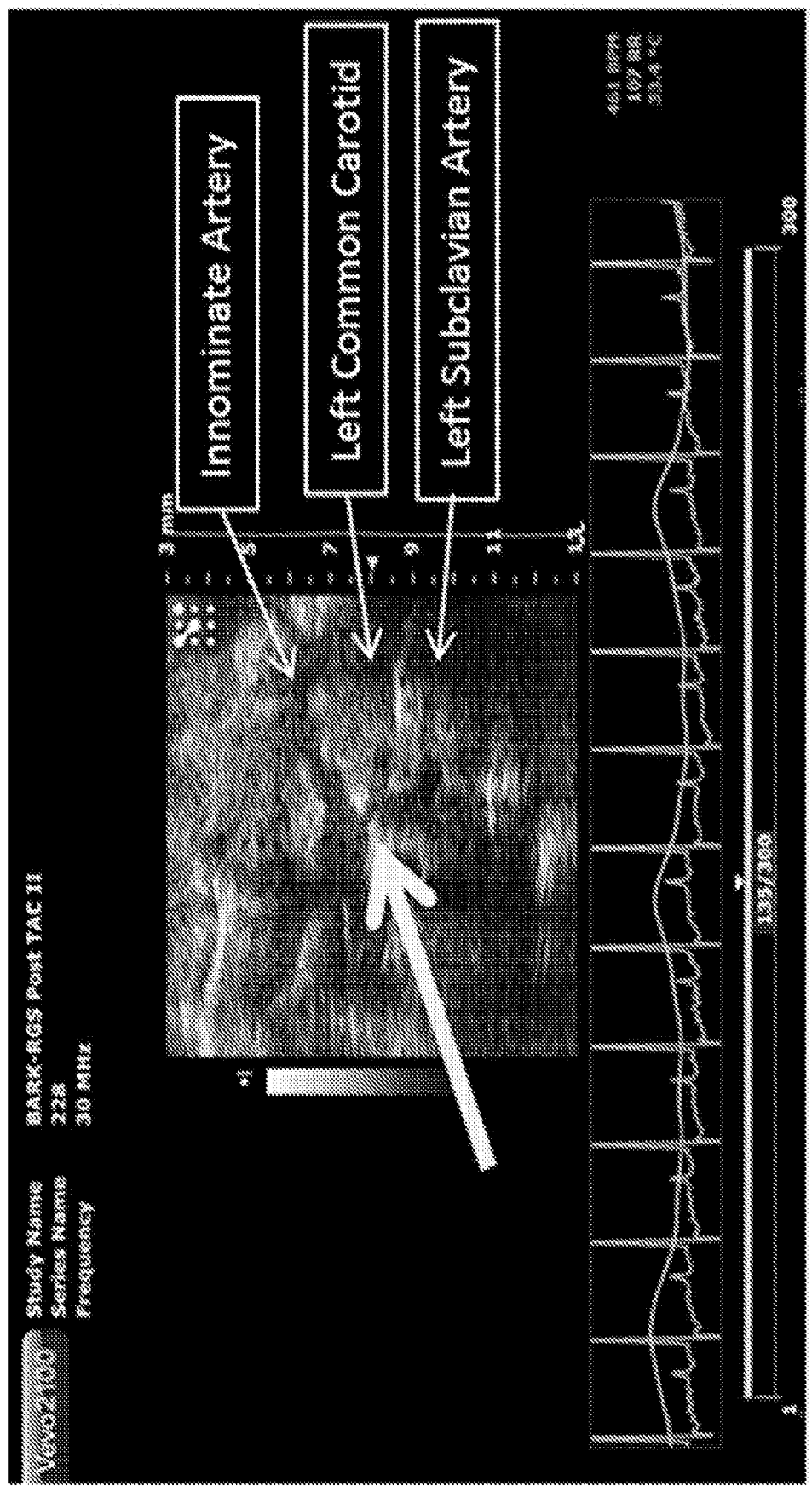
Figure 3C:
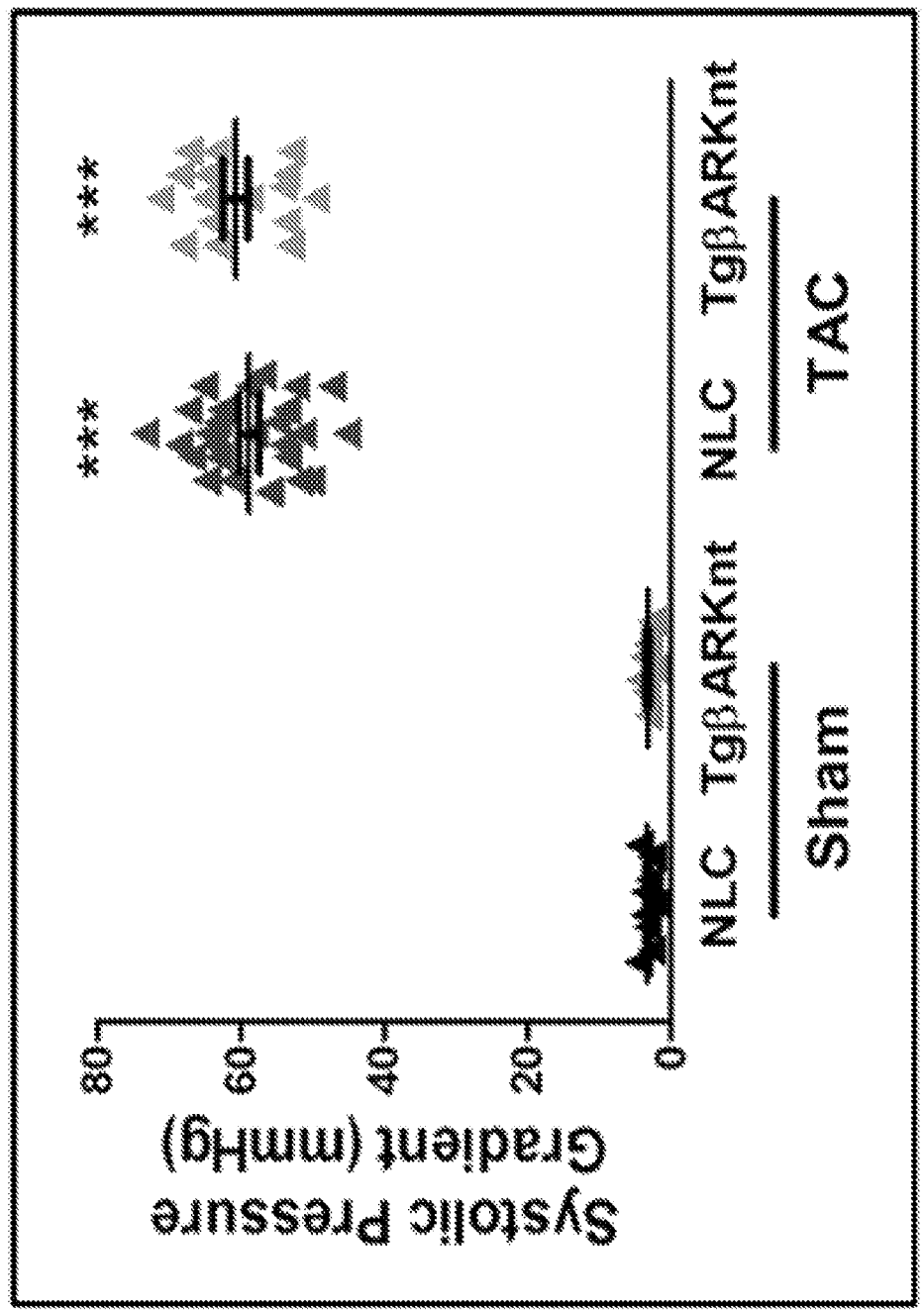
Figure 4A:
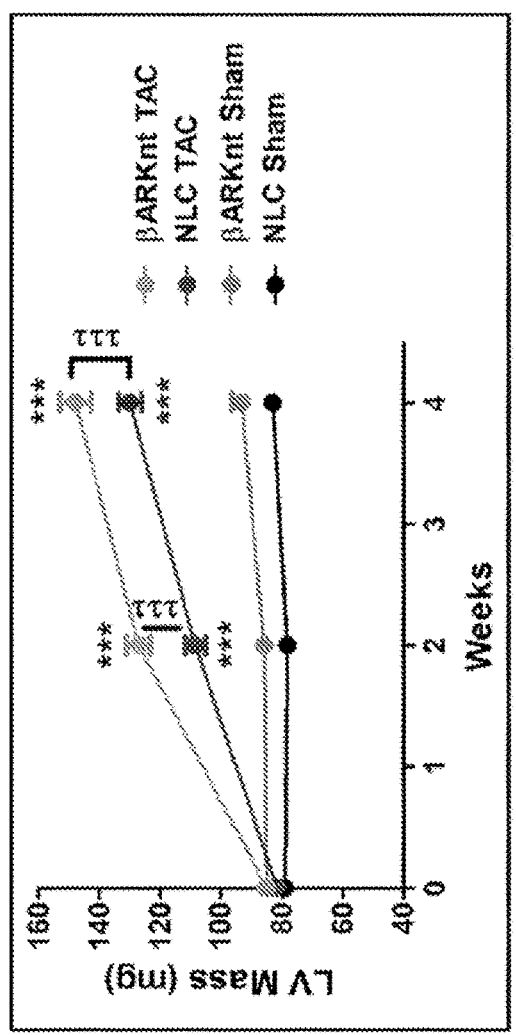
FIG. 4A through FIG. 4D, depicts results from example experiments demonstrating that cardiac-specific βARKnt expression exacerbates left ventricular hypertrophy after TAC.
Figure 4B:
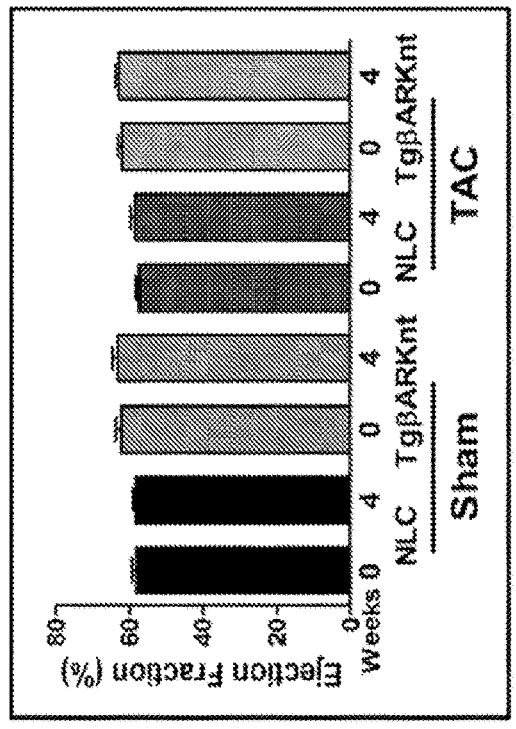
Figure 4C:
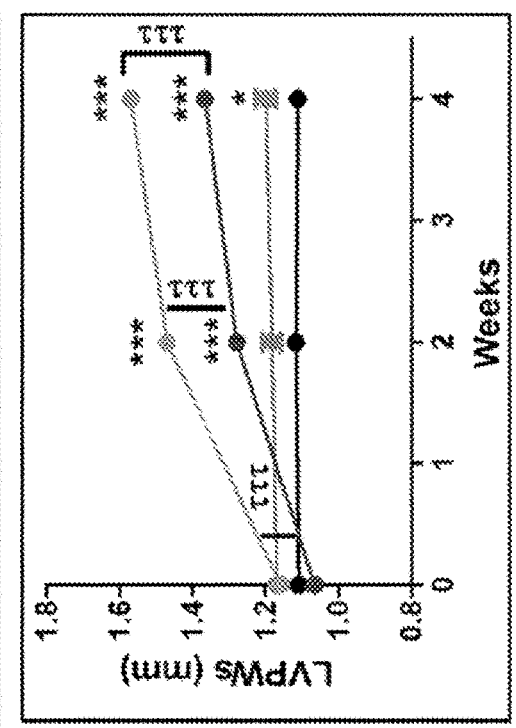
Figure 4D:
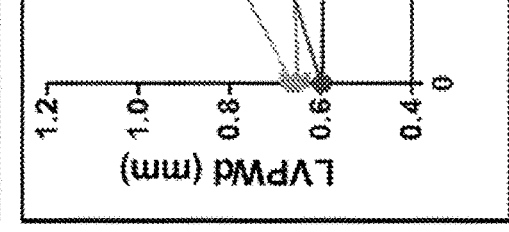
Figure 5A:
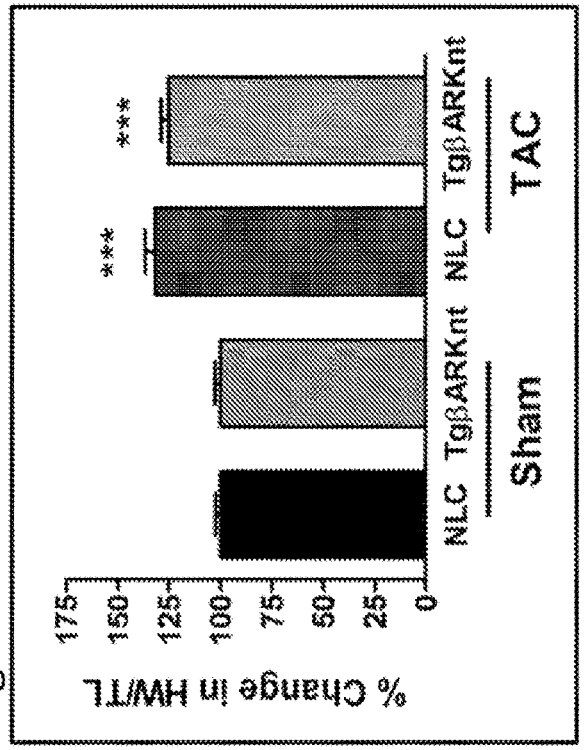
FIG. 5A through 5D, depicts results from example experiments demonstrating that increased HW and LAW is similar in TgβARKnt and NLC mice 4 weeks after TAC.
Figure 5B:
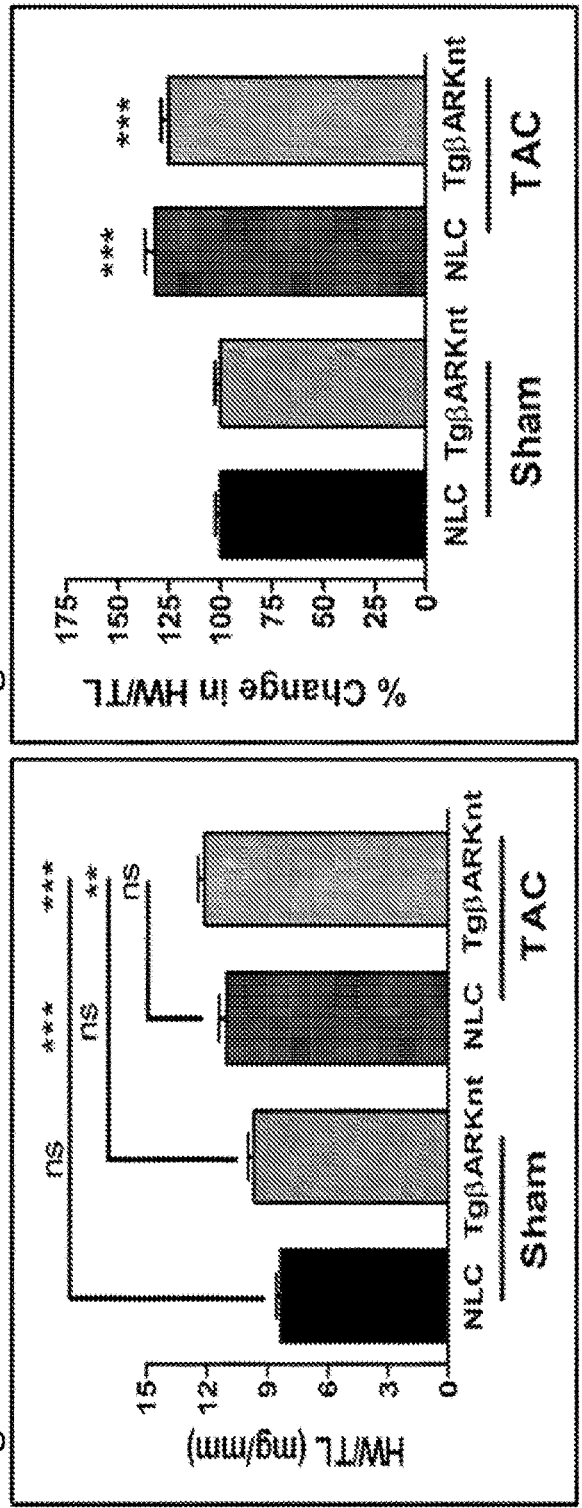
Figure 5C:
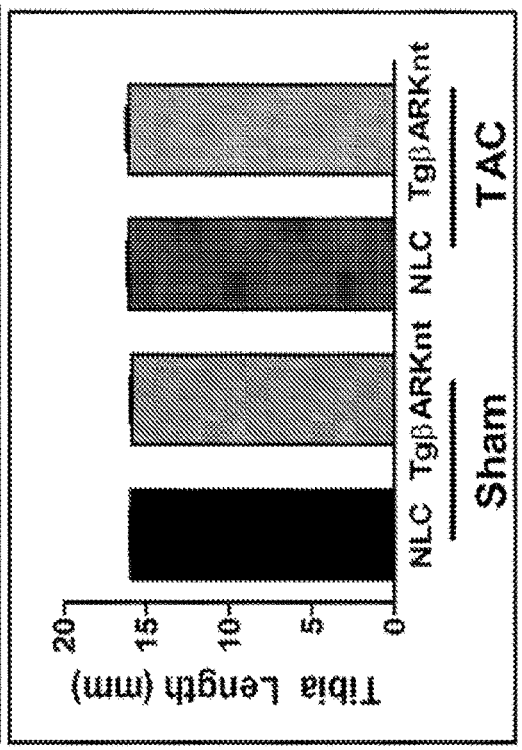
Figure 5D:
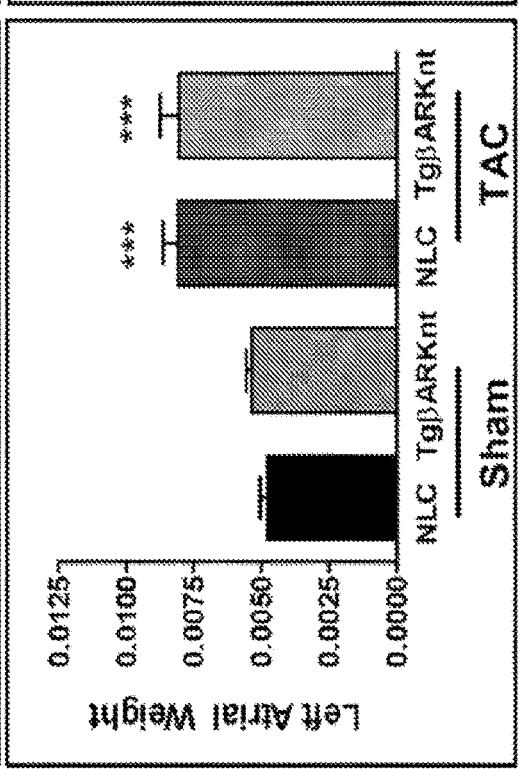
Figures 6A, 6B, 6C:
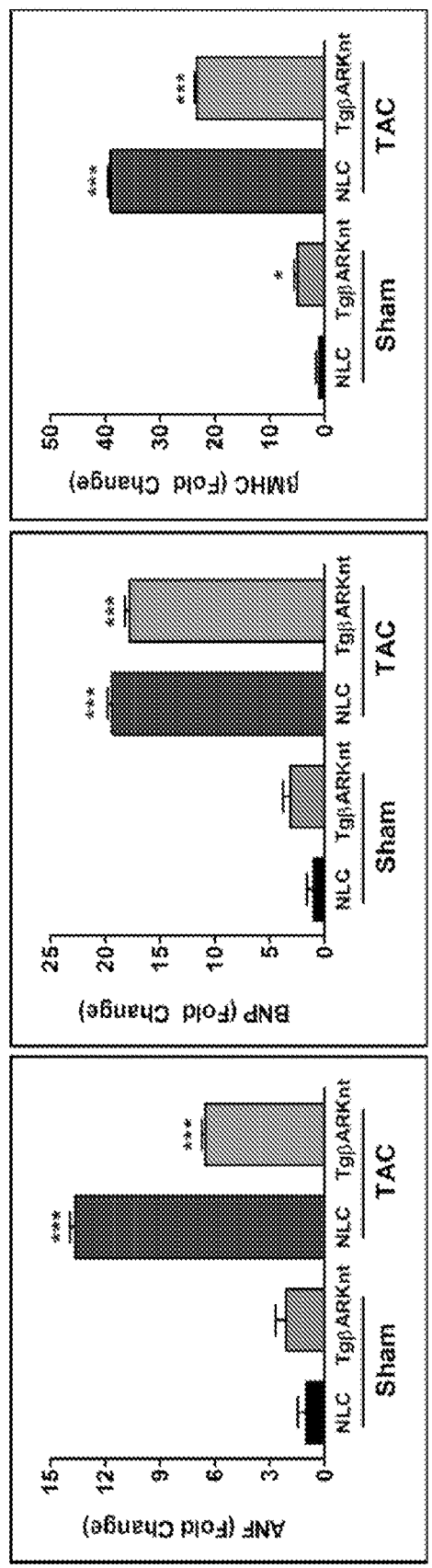
FIG. 6A through FIG. 6C, depicts results from example experiments demonstrating that fetal gene induction is similar in βARKnt and NLC mice 4 wks post-TAC.
Figure 7A:
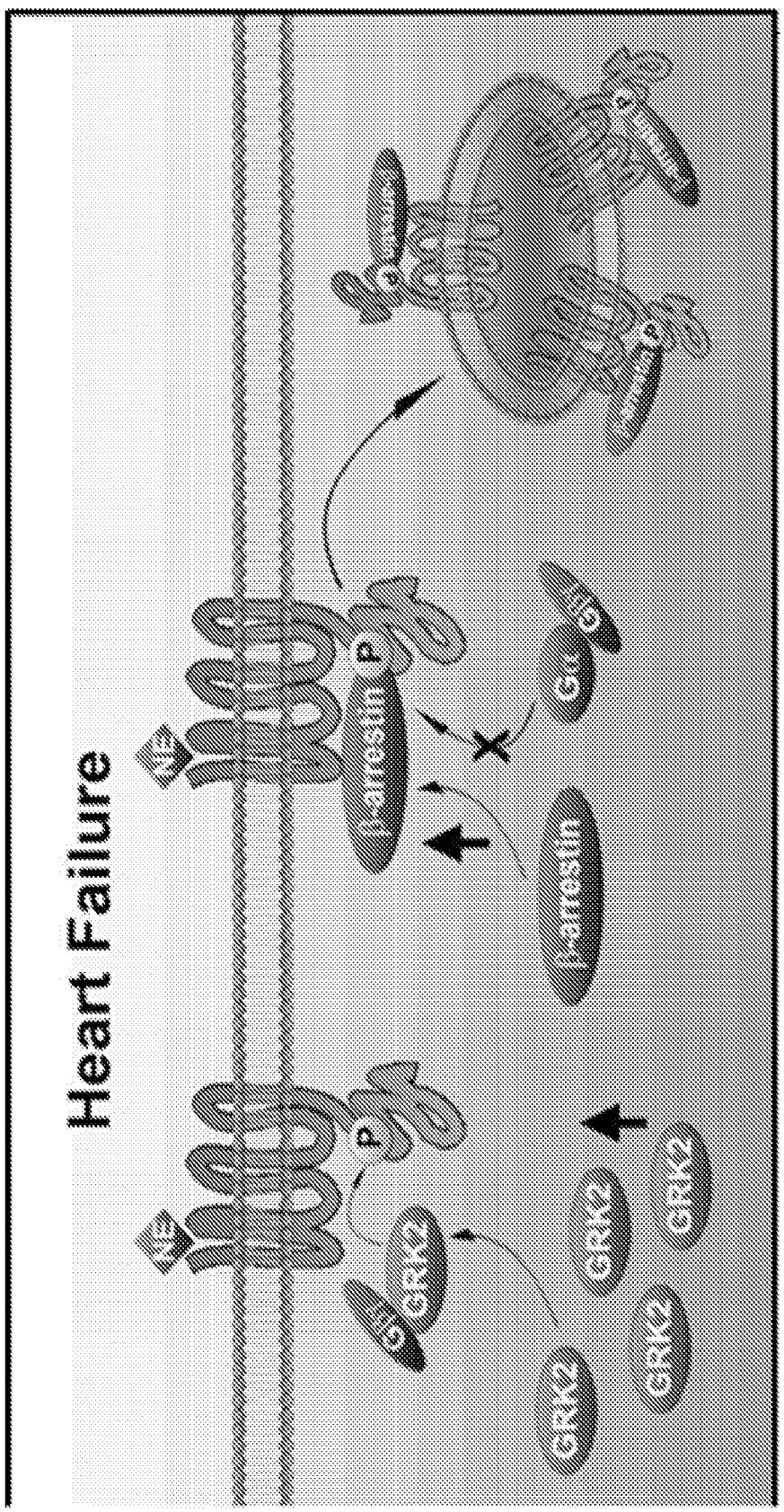
FIG. 7A through FIG. 7E, depicts results from example experiments demonstrating that hypertrophy is unaltered in TgGRK2 mice after TAC.
Figure 7B:
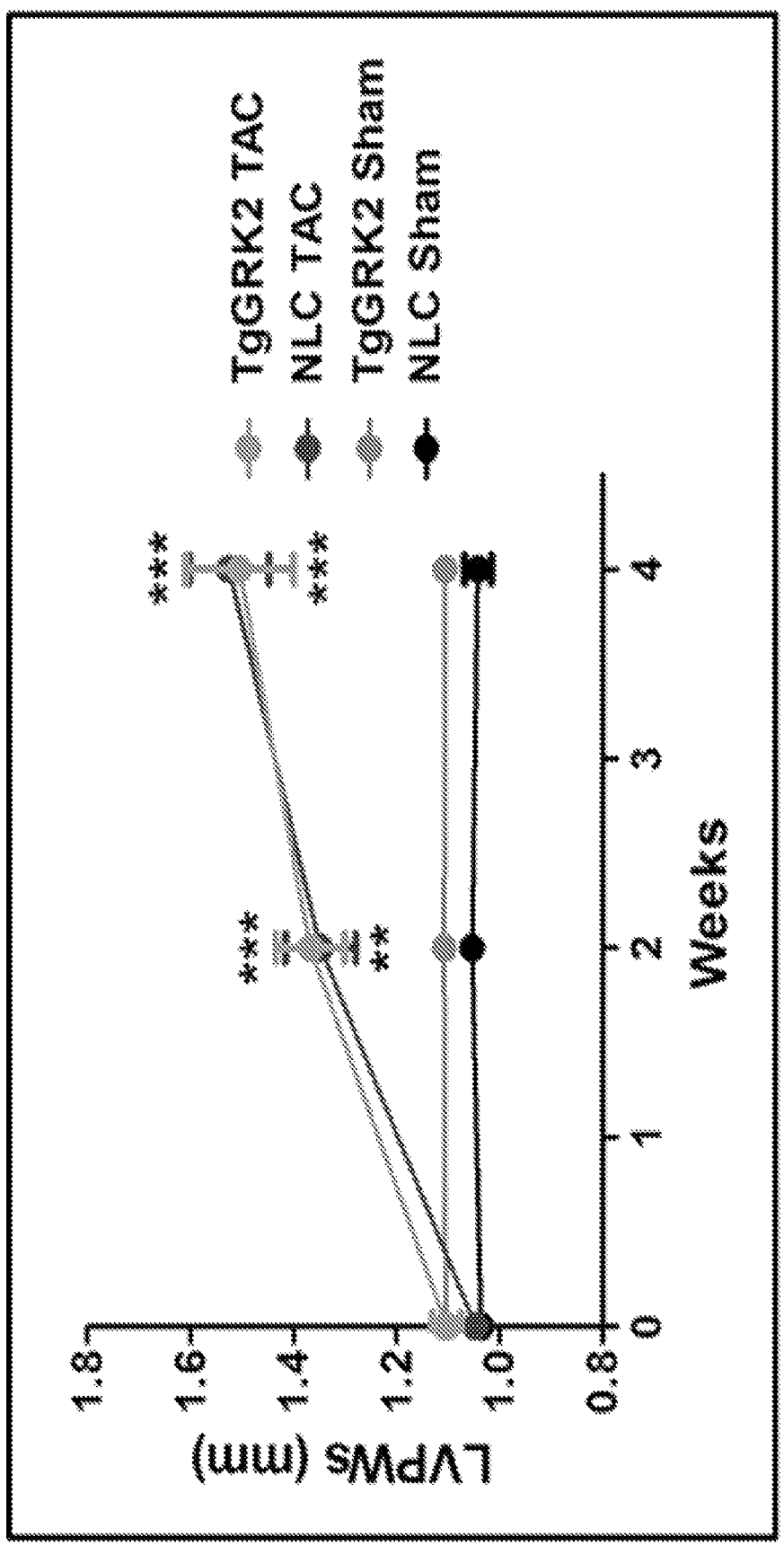
Figure 7C:
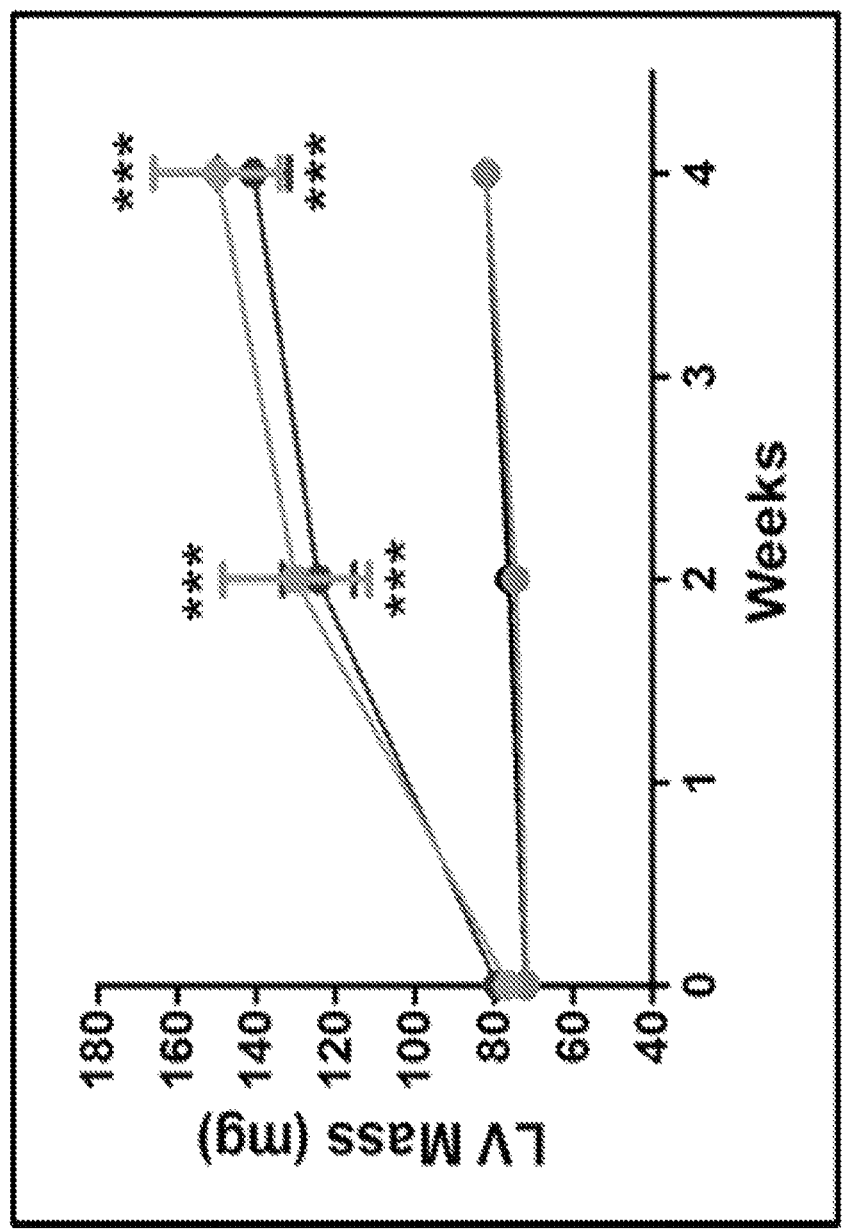
Figure 7D:
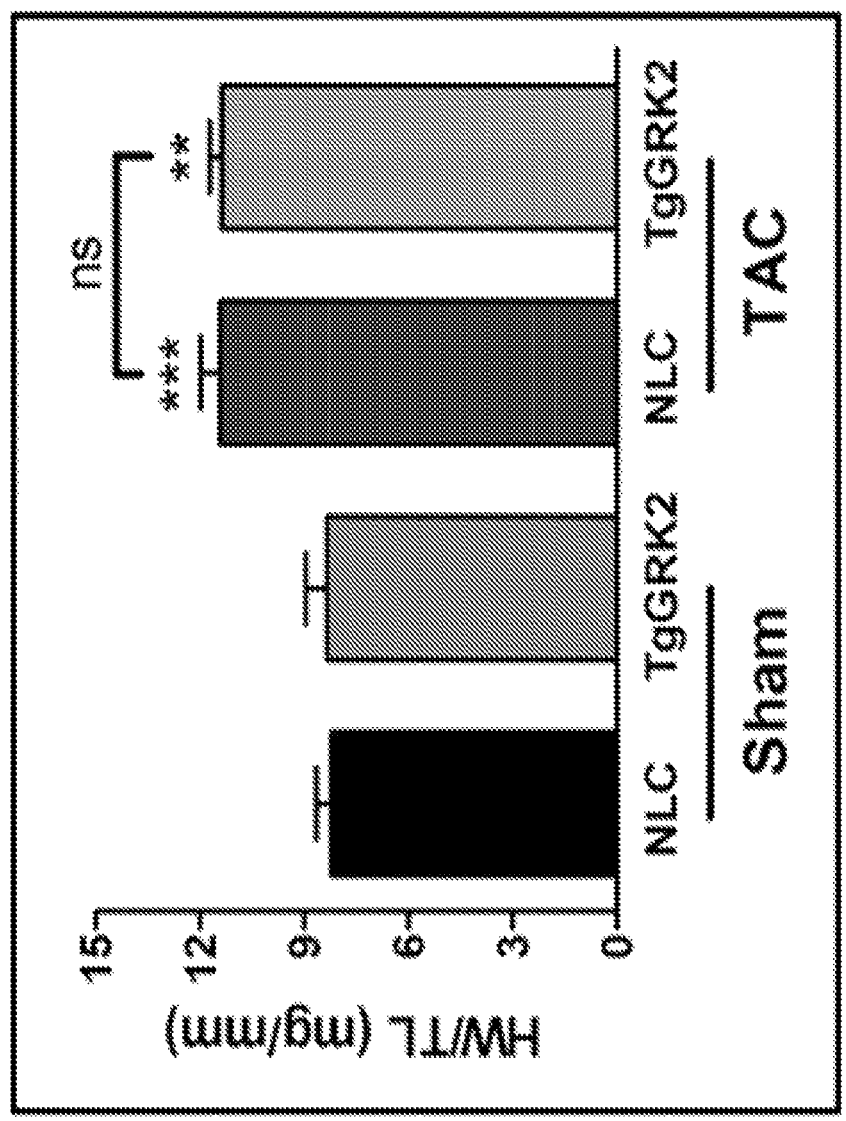
Figure 7E:
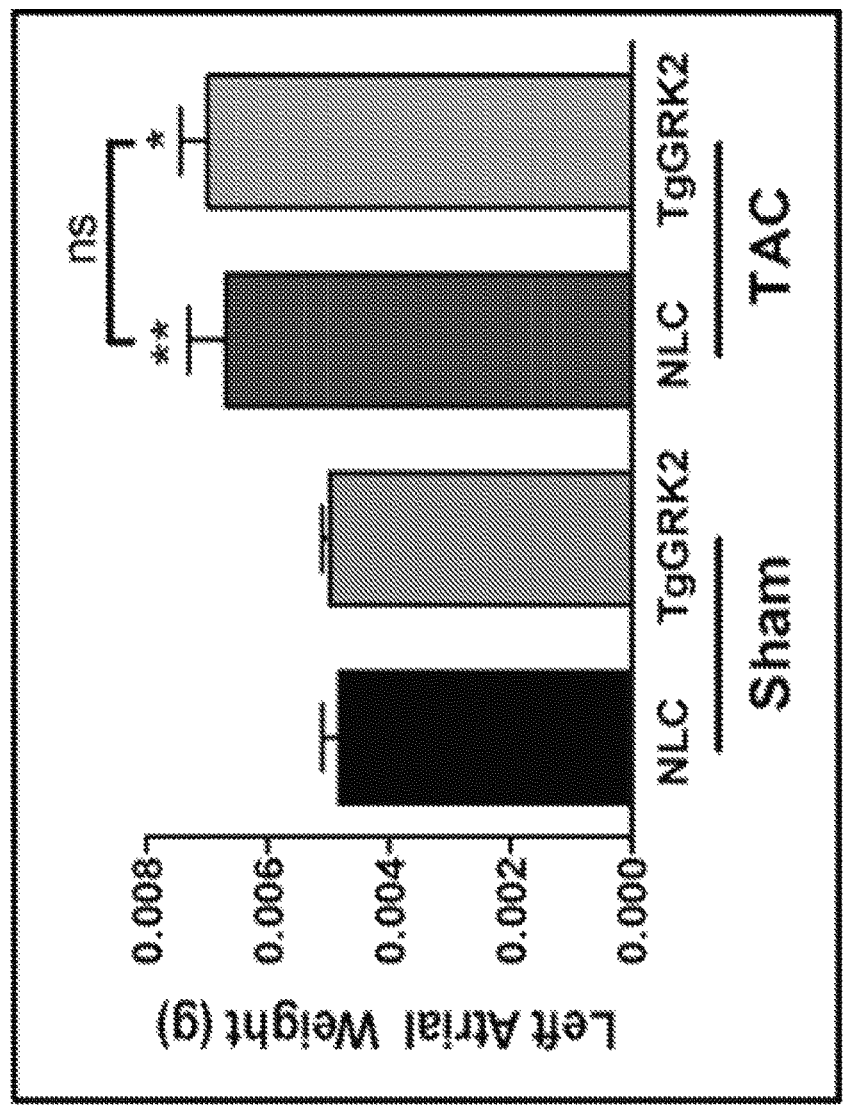
Figure 8A:
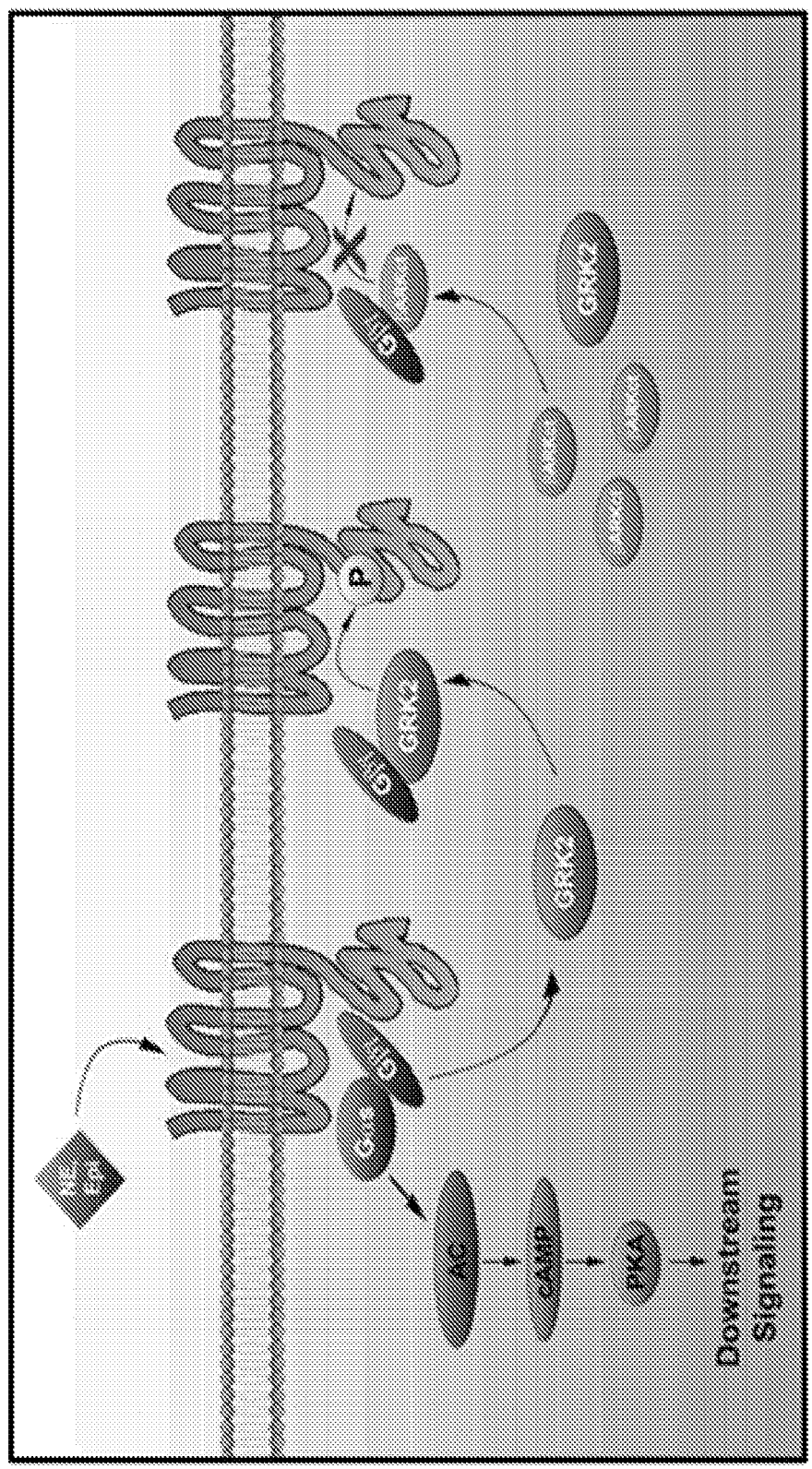
FIG. 8A through FIG. 8E, depicts results from example experiments demonstrating that hypertrophy is unaltered in TgβARKct mice after TAC.
Figure 8B:
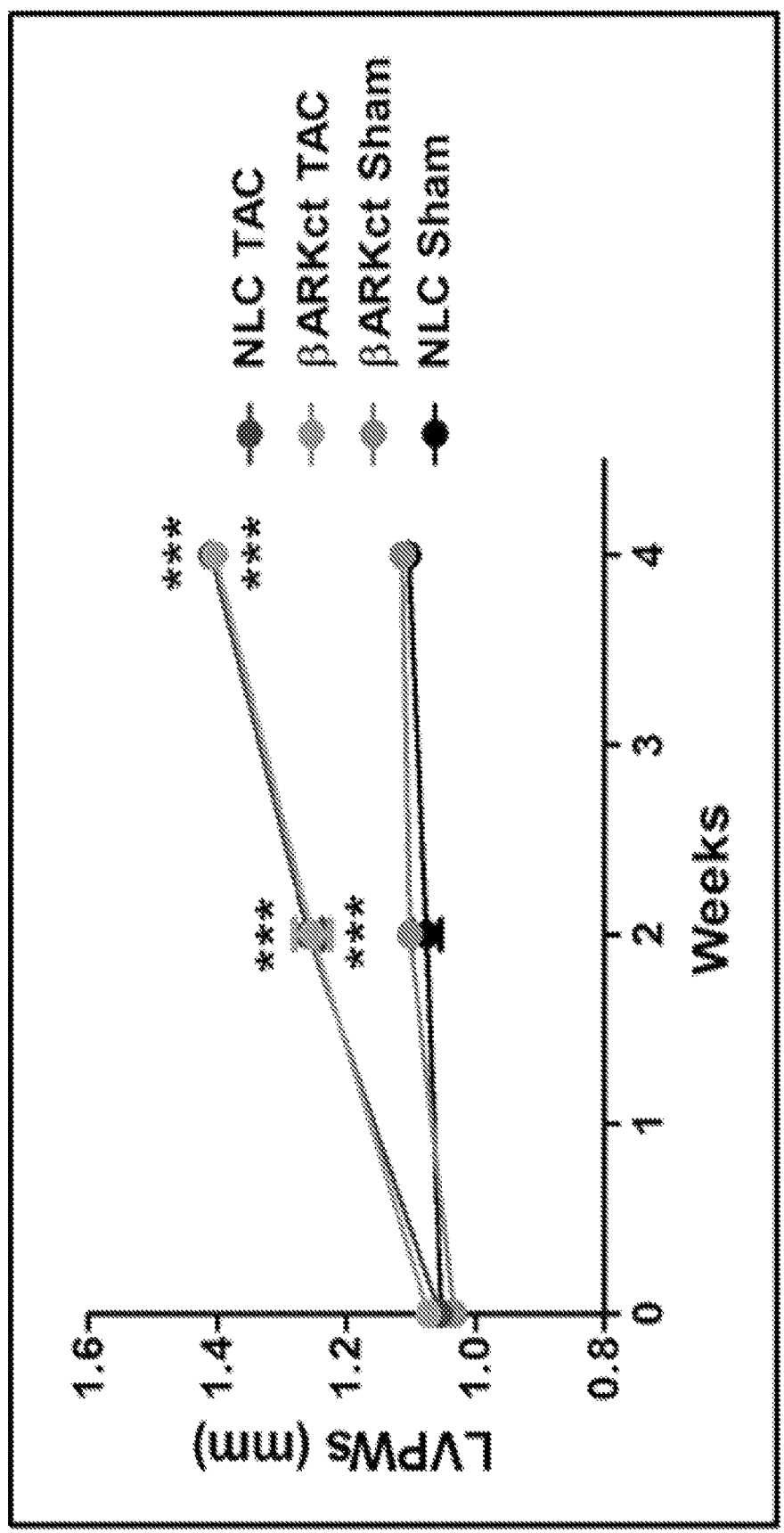
Figure 8C:
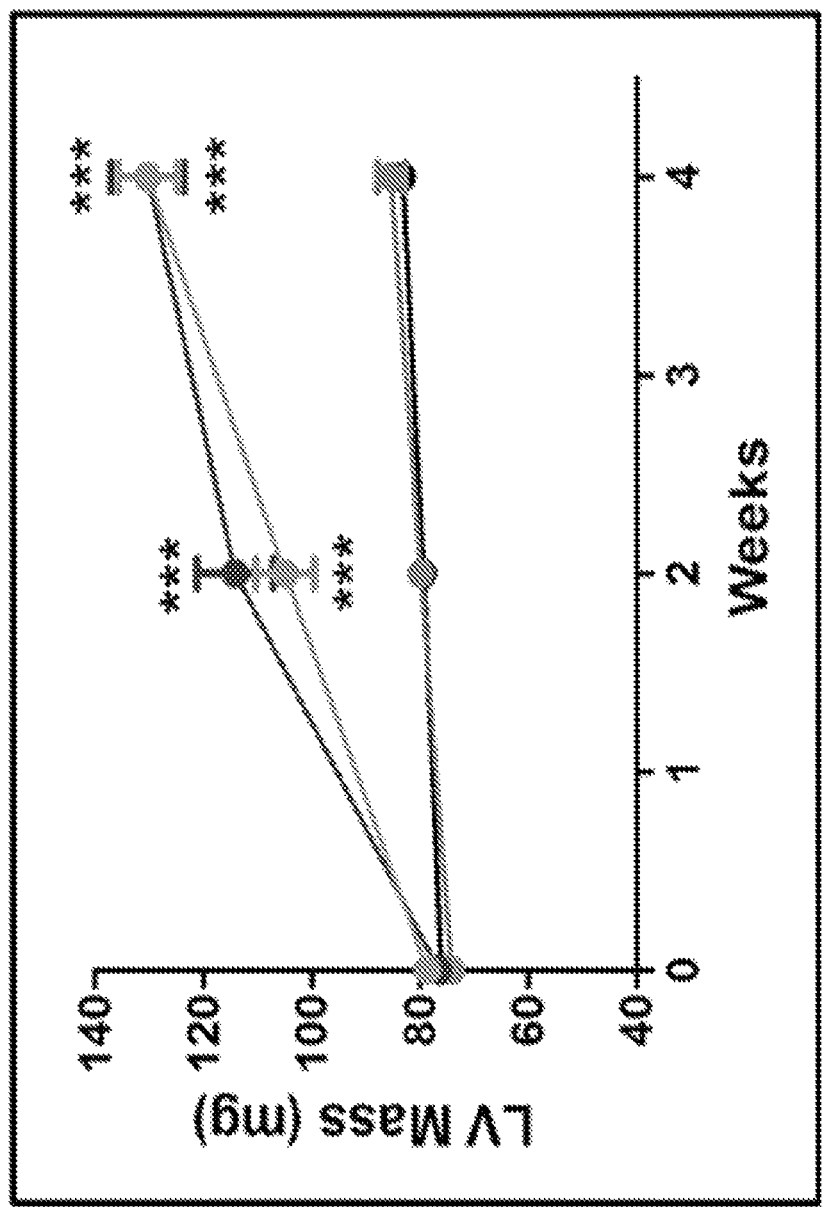
Figure 8D:
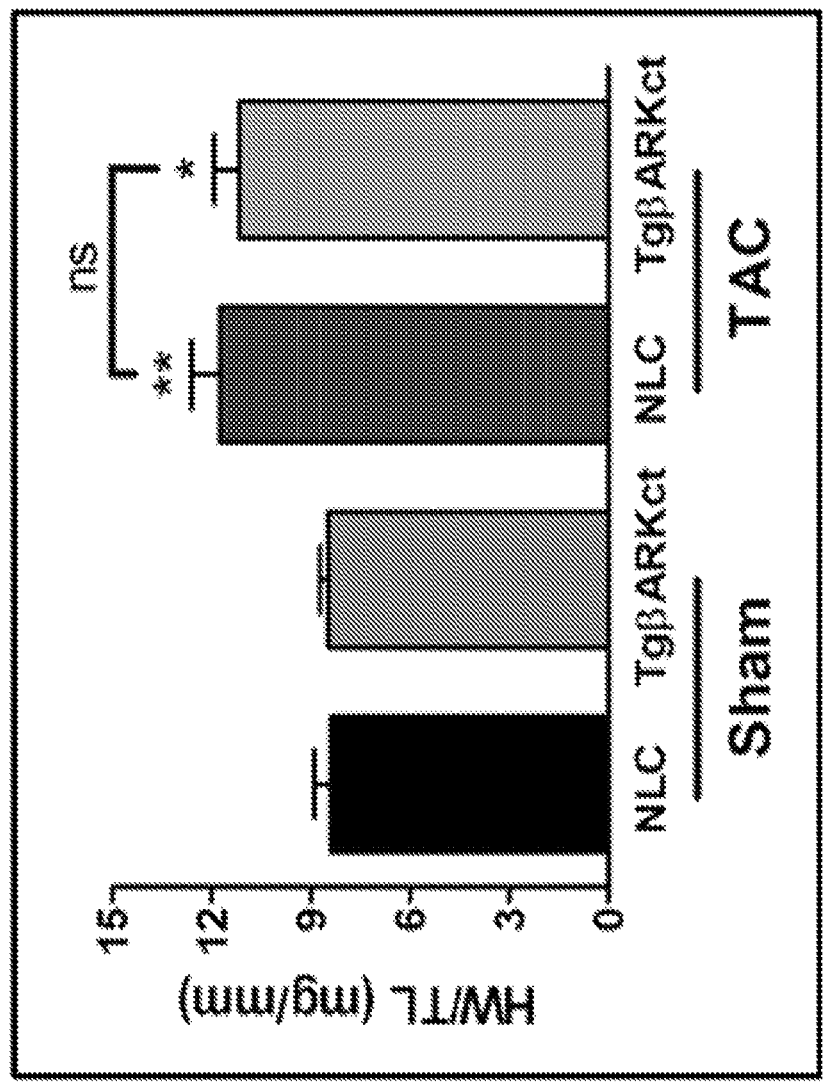
Figure 8E:
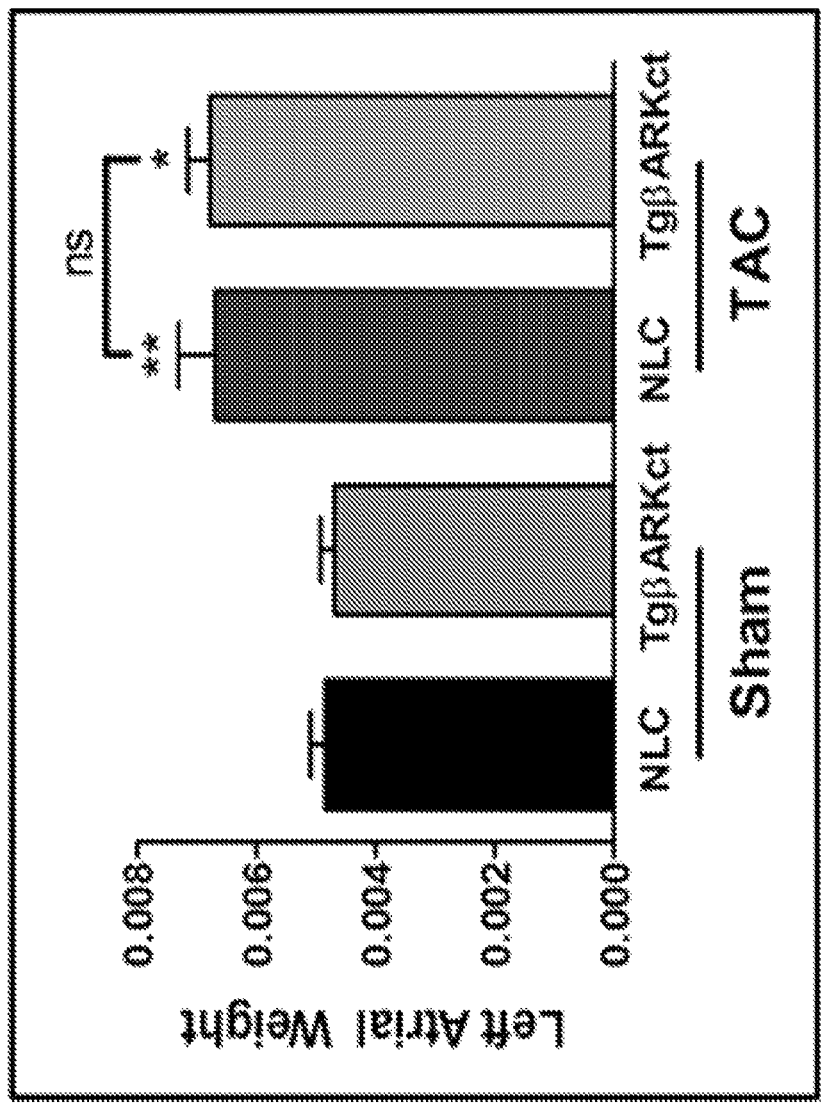
Figure 9B:
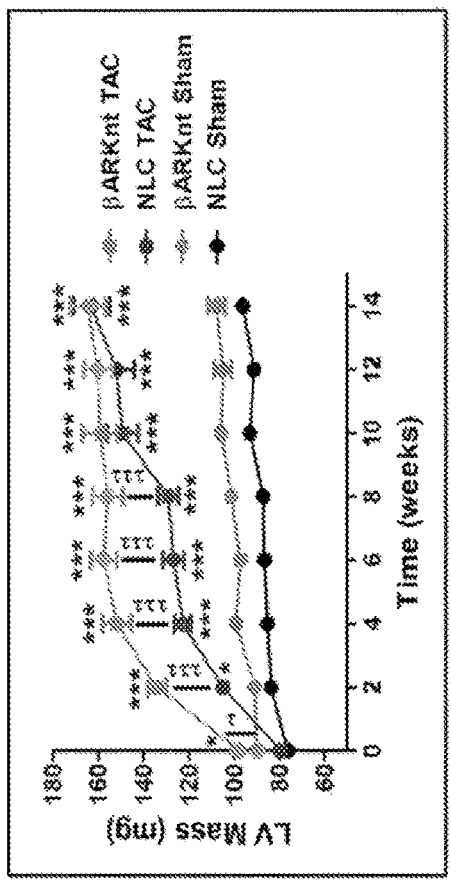
FIG. 9A through FIG. 9D, depicts results from example experiments demonstrating that chronic pressure-overload induced HF is blocked by cardiac βARKnt expression.
Figure 9D:
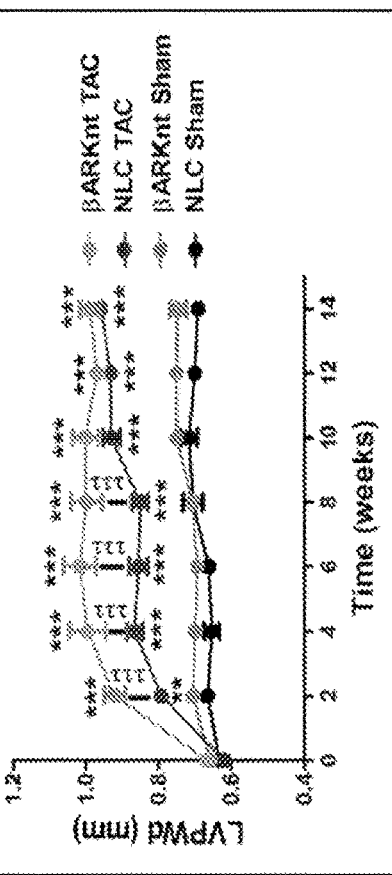
Figure 9A:
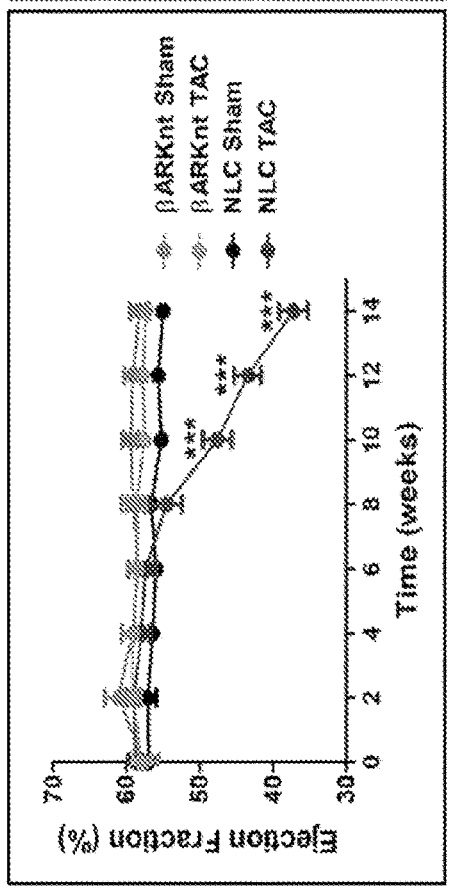
Figure 9C:
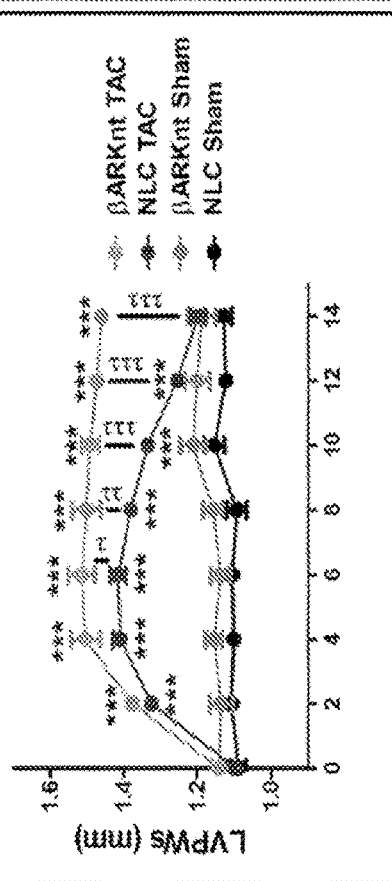
Figure 11A:
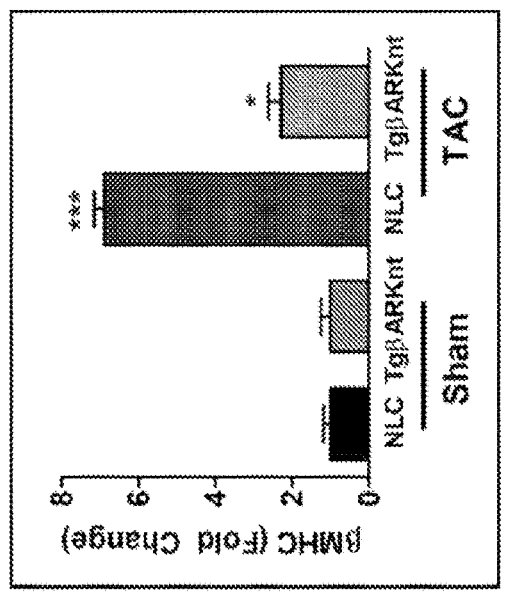
FIG. 11A through FIG. 11C, depicts results from example experiments demonstrating that fetal gene expression is normalized in βARKnt mice compared to NLC 14 weeks post-TAC.
Figure 11B:
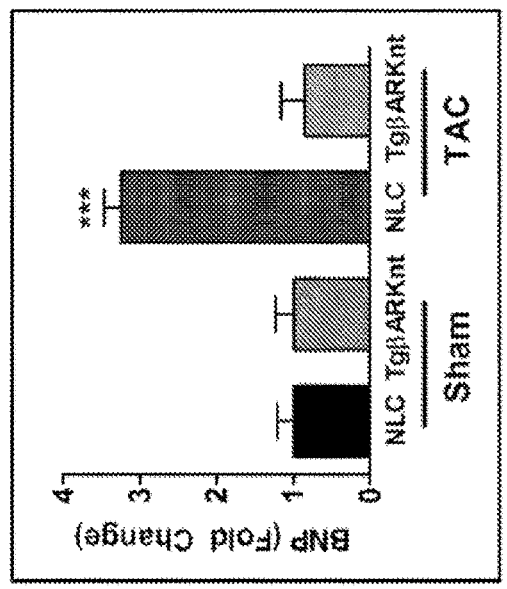
Figure 11C:
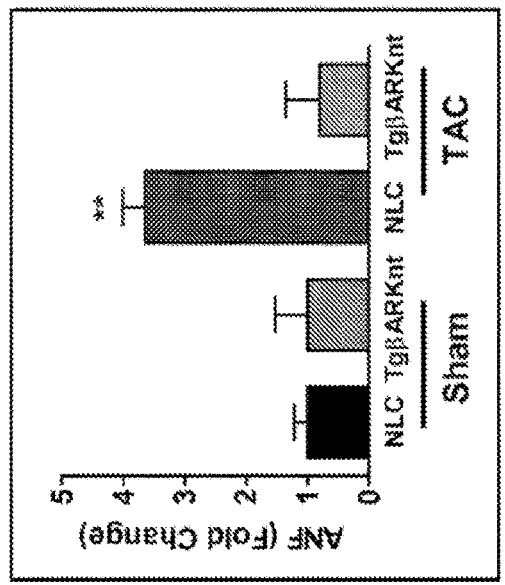
Figure 12B:
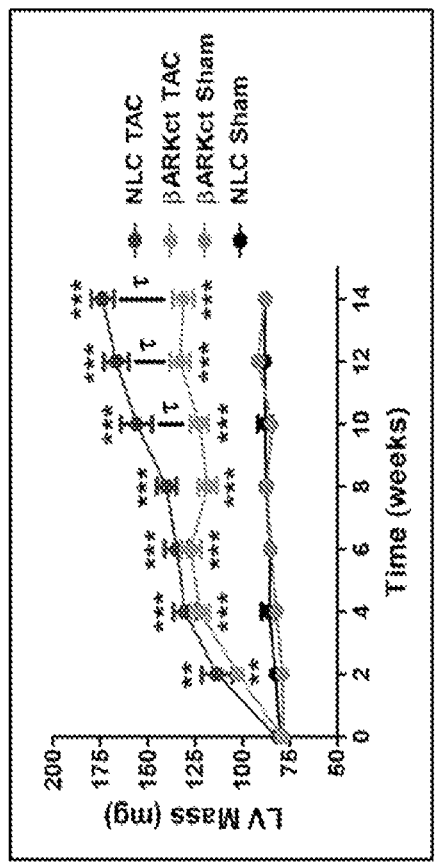
FIG. 12A through FIG. 12D, depicts results from example experiments demonstrating that chronic pressure-overload induced heart failure is inhibited by cardiac βARKct expression.
Figure 12D:
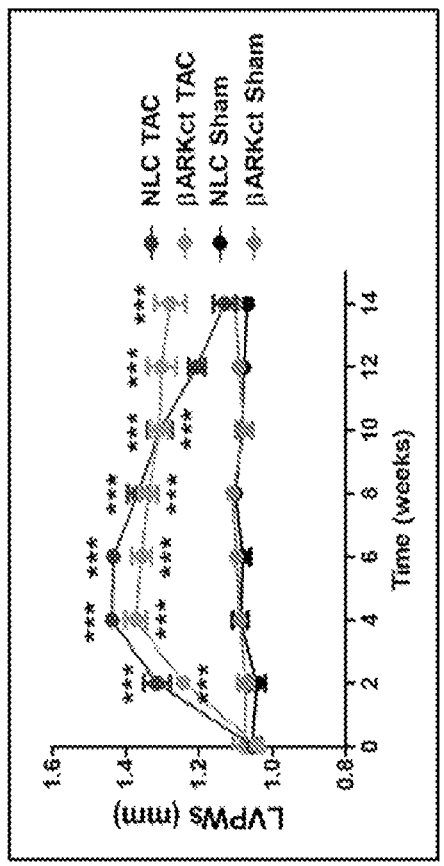
Figure 12A:
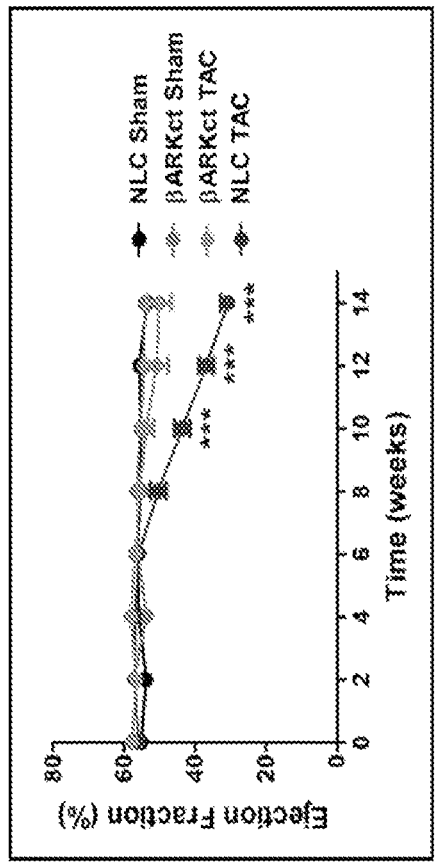
Figure 12C:
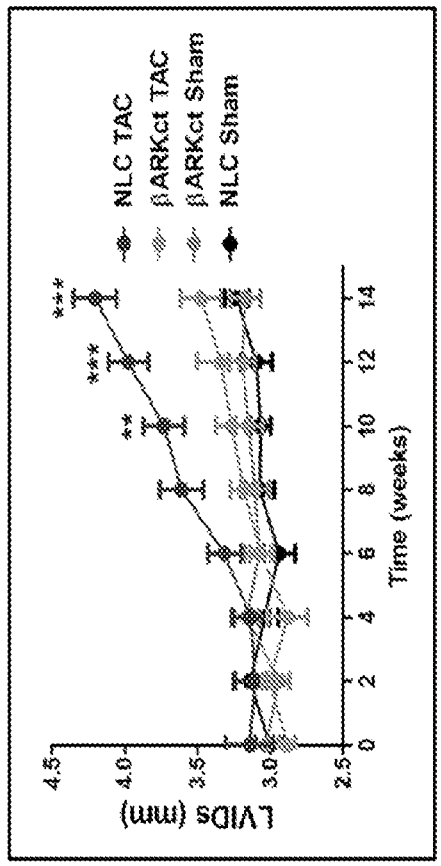
Figure 13B:
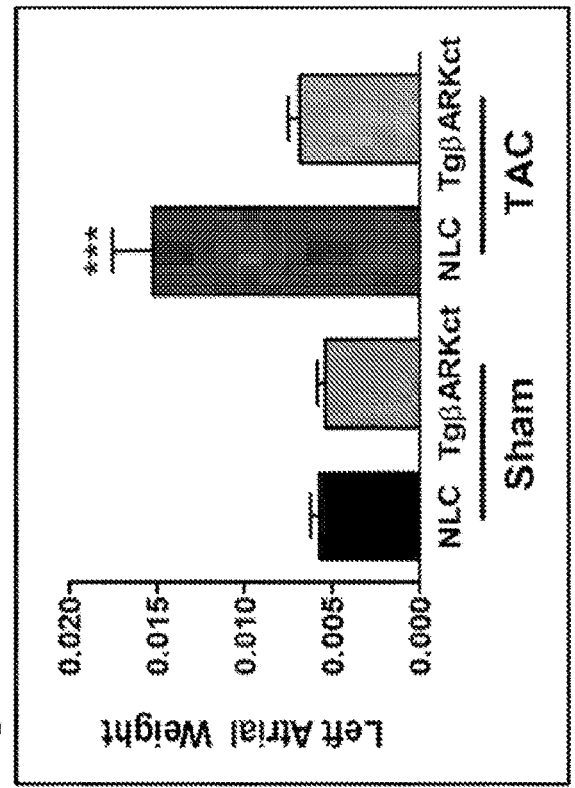
FIG. 13A through FIG. 13C, depicts results from example experiments demonstrating that chronic pressure-overload induced heart failure is inhibited by cardiac βARKct expression.
Figure 13A:
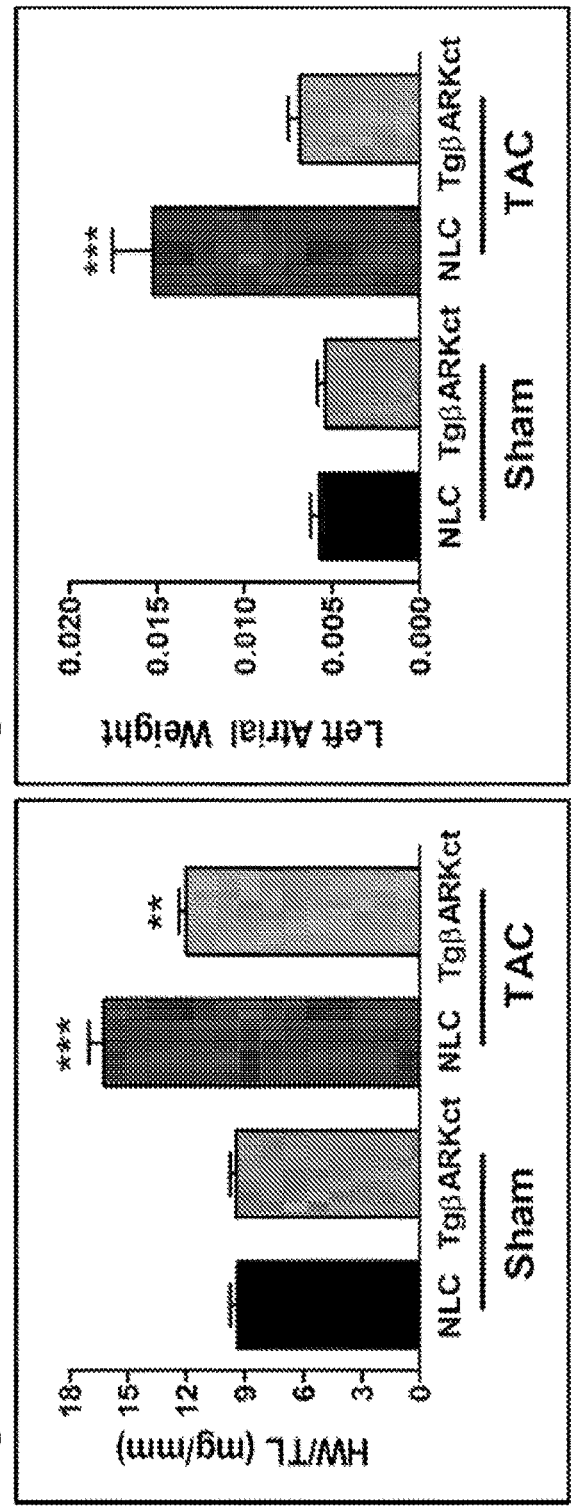
Figure 13C:
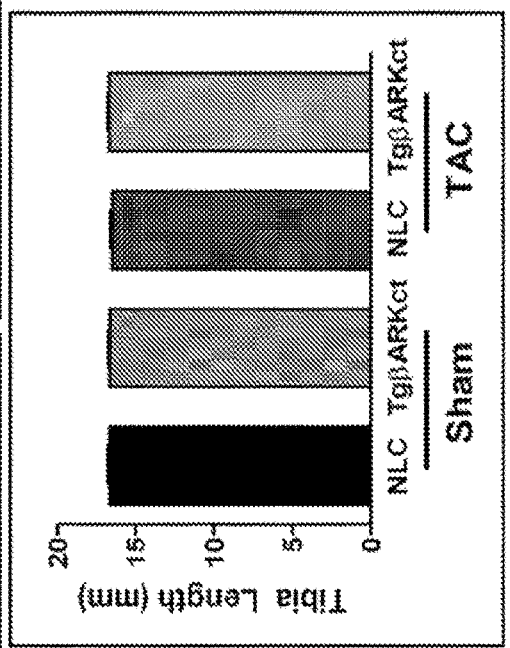

To determine whether βARKrgs expression could alter hypertrophy in an animal model of pressure-overload, transgenic and NLC mice underwent trans-aortic constriction (TAC) or sham surgery. TAC was confirmed by pulsed-wave Doppler of the aortic arch 24 hr post-surgery to measure the systolic pressure gradient across the point of constriction, and this was important to confirm the level of cardiac stress was the same between TAC groups. Echocardiography was performed at baseline, 2, and 4 weeks to monitor cardiac function and dimensions. Over this time course no effect of TAC on LVEF was typically found (FIG. 3).

To further elucidate whether the observed effects were a selective interaction of βARKrgs with Gq and not a GRK2-mediated effect, mice with cardiac-restricted GRK2 overexpression were studied, wherein the levels of GRK2 are similar to those observed in human HF. Unlike the βARKrgs and GqI mice, cardiac hypertrophy was unaltered in GRK2 overexpressing mice, with the significant increase in LVPWs and mass nearly identical between transgenic and their respective NLCs 4 weeks post-TAC. Similarly, HW and LAW were elevated to the same degree. These data demonstrate that gain-of-function of full-length GRK2 is not sufficient to alter cardiac hypertrophic responses, and suggests that the RGS domain of GRK2 embodies distinct functional interactions that prevent hypertrophic signaling in the heart (FIG. 7).

To further elucidate whether there was a selective interaction of βARKrgs with Gq and not a GRK2-mediated effect, cardiac-targeted bARKct transgenic mice (TgbARKct) were utilized, which express the c-terminal 194 amino acids of GRK2 that competes for binding to Gβγ and membrane translocation, acting as a peptide inhibitor of GRK2 activity on GPCRs. Unlike βARKrgs and GqI Tg mice, cardiac hypertrophy was unaltered in TgbARKct mice, with the significant increase in LVPWs and LV mass nearly identical between TgbARKct and their respective NLCs 4 weeks post-TAC. Similarly, heart weight and left atrial weight were elevated to the same degree (FIG. 8).

Figure 14A:
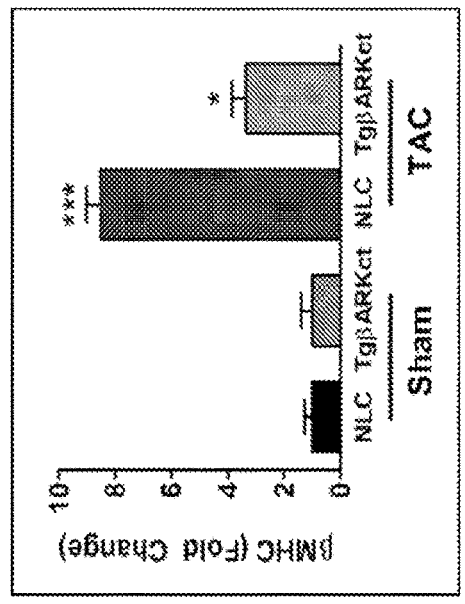
FIG. 14A through FIG. 14C, depicts results from example experiments, demonstrating that chronic pressure-overload induced heart failure is inhibited by cardiac βARKct expression.
Figure 14B:
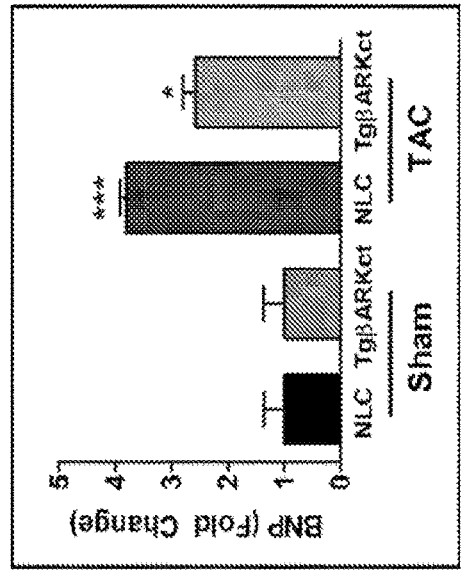
Figure 14C:
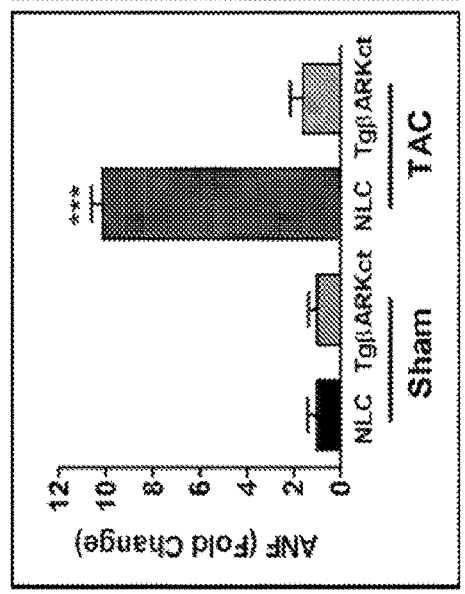
Figure 15B:
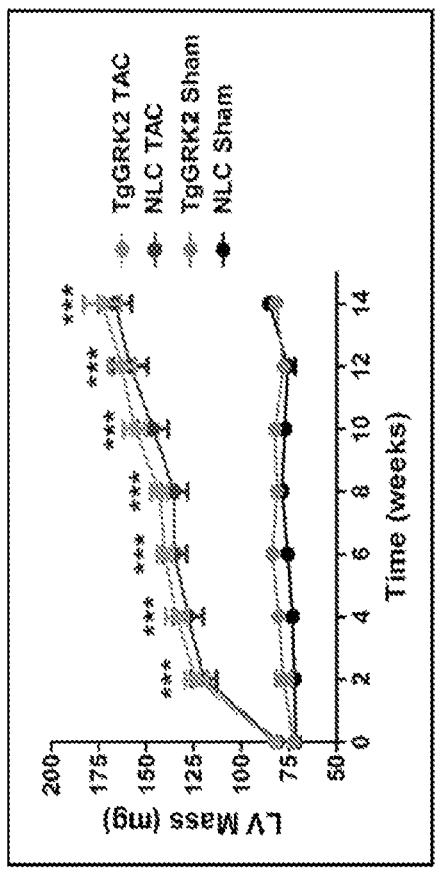
FIG. 15A through FIG. 15D, depicts results from example experiments demonstrating that cardiac GRK2 overexpression hastens progression to heart failure during chronic pressure-overload.
Figure 15D:
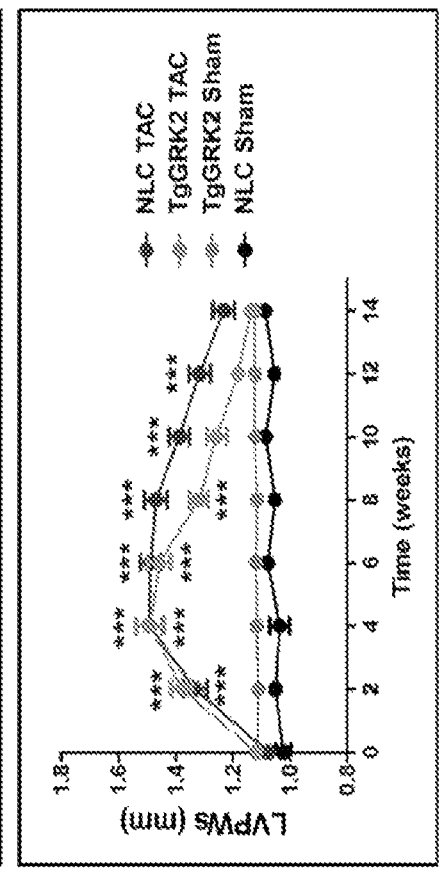
Figure 15A:
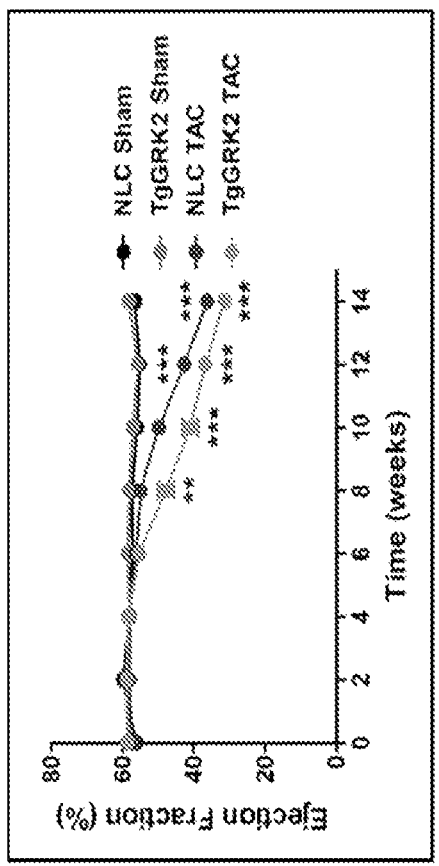
Figure 15C:
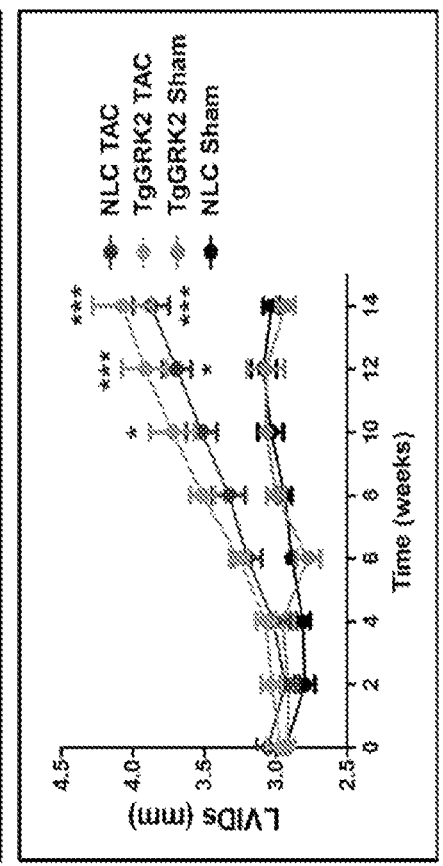
Figure 17C:
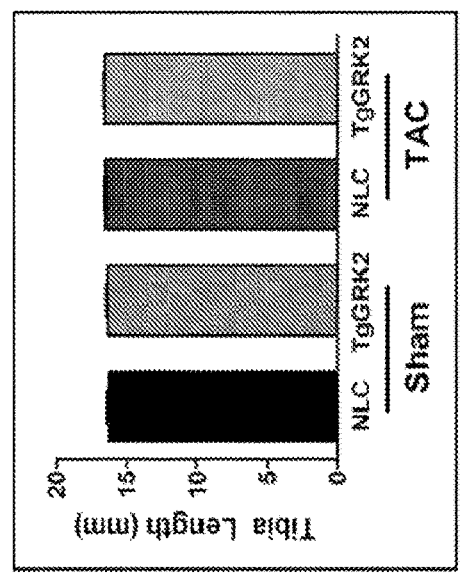
FIG. 17A through FIG. 17C, depicts results from example experiments demonstrating that cardiac GRK2 overexpression hastens progression to heart failure during chronic pressure-overload.
Figure 17B:
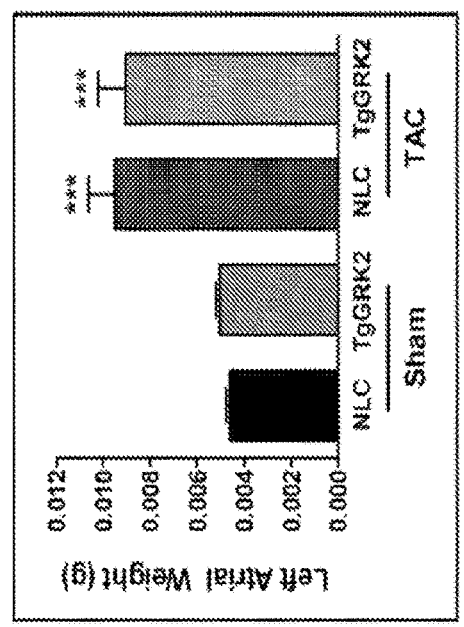
Figure 17A:
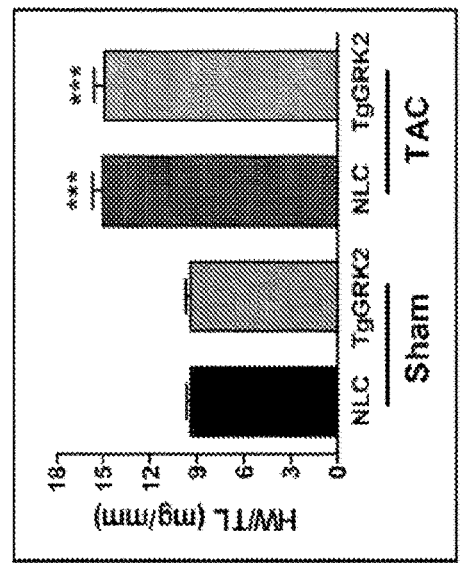
Figure 18B:
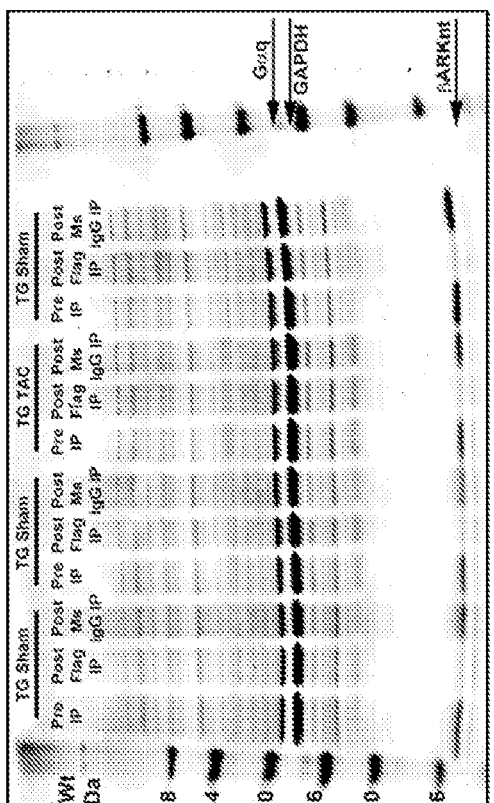
FIG. 18A through FIG. 18E, depicts results from example experiments demonstrating that the βARKnt peptide does not interact with endogenous Gαq or GRK2 in the heart.
Figure 18A:
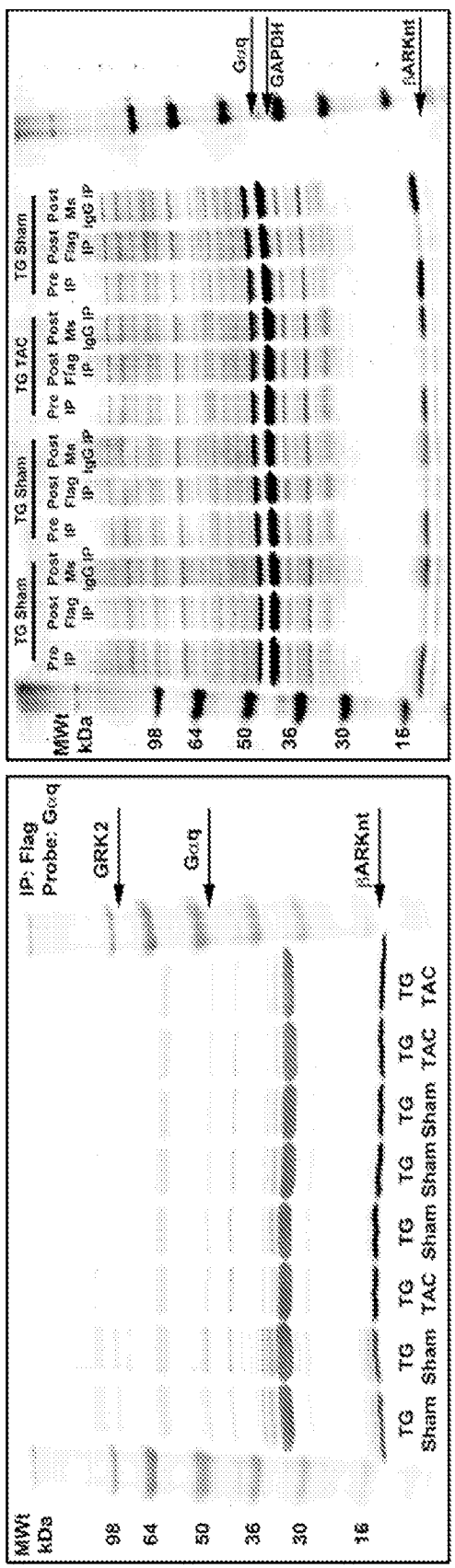
Figure 18E:
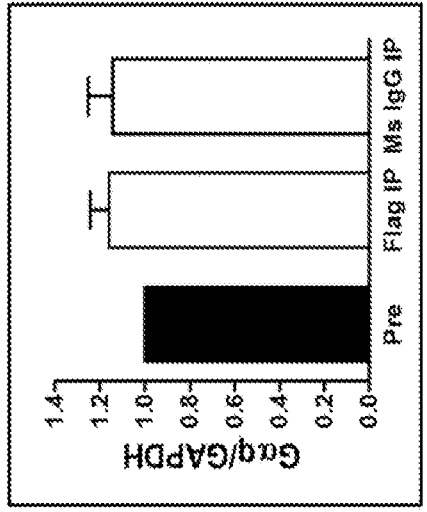
Figure 18D:
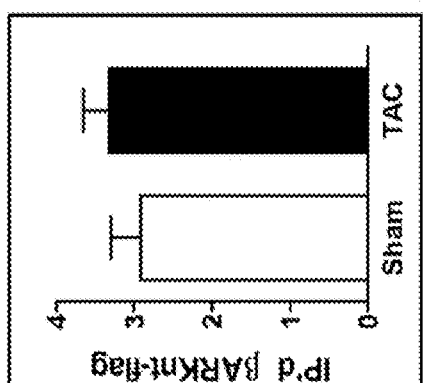
Figure 18C:
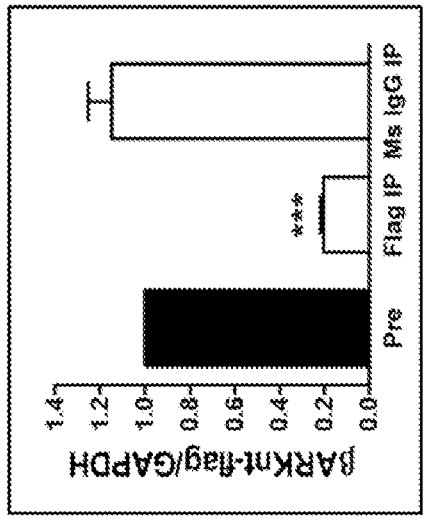

One hallmark of human HF is the induction of the fetal gene program; therefore atrial natriuretic factor, brain natriuretic factor, and beta myosin heavy chain mRNA expression was analyzed via RT-PCR in the myocardial samples. Induction of the fetal gene program was observed. Further, hypertrophic gene expression was measured via RT-PCR of cardiac mRNA and fetal gene induction was similar between these animals. Together, these data demonstrate proportional hypertrophic growth in the βARKnt transgenic and NLC mice in response to cardiac stress (FIG. 14).

In contrast to the cardioprotection provided by βARKrgs, GRK2 overexpression demonstrated the opposite effect, hastening the decompensation to HF with a more rapid deterioration in function and expansion of the LV, and a more progressive reduction in wall thickness, further suggesting that the βARKrgs peptide alone encompasses functional interactions that do not occur within the full-length enzyme in vivo. To investigate the underlying mechanisms of action of the βARKrgs peptide, tissues were taken for biochemical and histological analysis 4 weeks post-TAC (FIG. 15).

To elucidate the underlying mechanisms of action of the βARKnt peptide, tissues were taken for histological and biochemical analysis 4 weeks after TAC and immunoprecipitation reactions were performed on NLC and TgβARKnt mice 4 weeks after Sham or TAC surgery to confirm that unlike the βARKrgs peptide, IP of flag-tagged βARKnt did not co-immunoprecipitate with Gαq, demonstrating that they do interact in complex with each other in vivo. Further, it was also found that the βARKnt did not co-IP with full-length GRK2. Western blot of cardiac lysates prior to and remaining after IP demonstrated that the flag IP was efficient and there was no difference in the amount of βARKnt IP'd from sham or TAC animals, confirming that βARKnt does not co-IP with Gaq (FIG. 18).

Figure 19A:
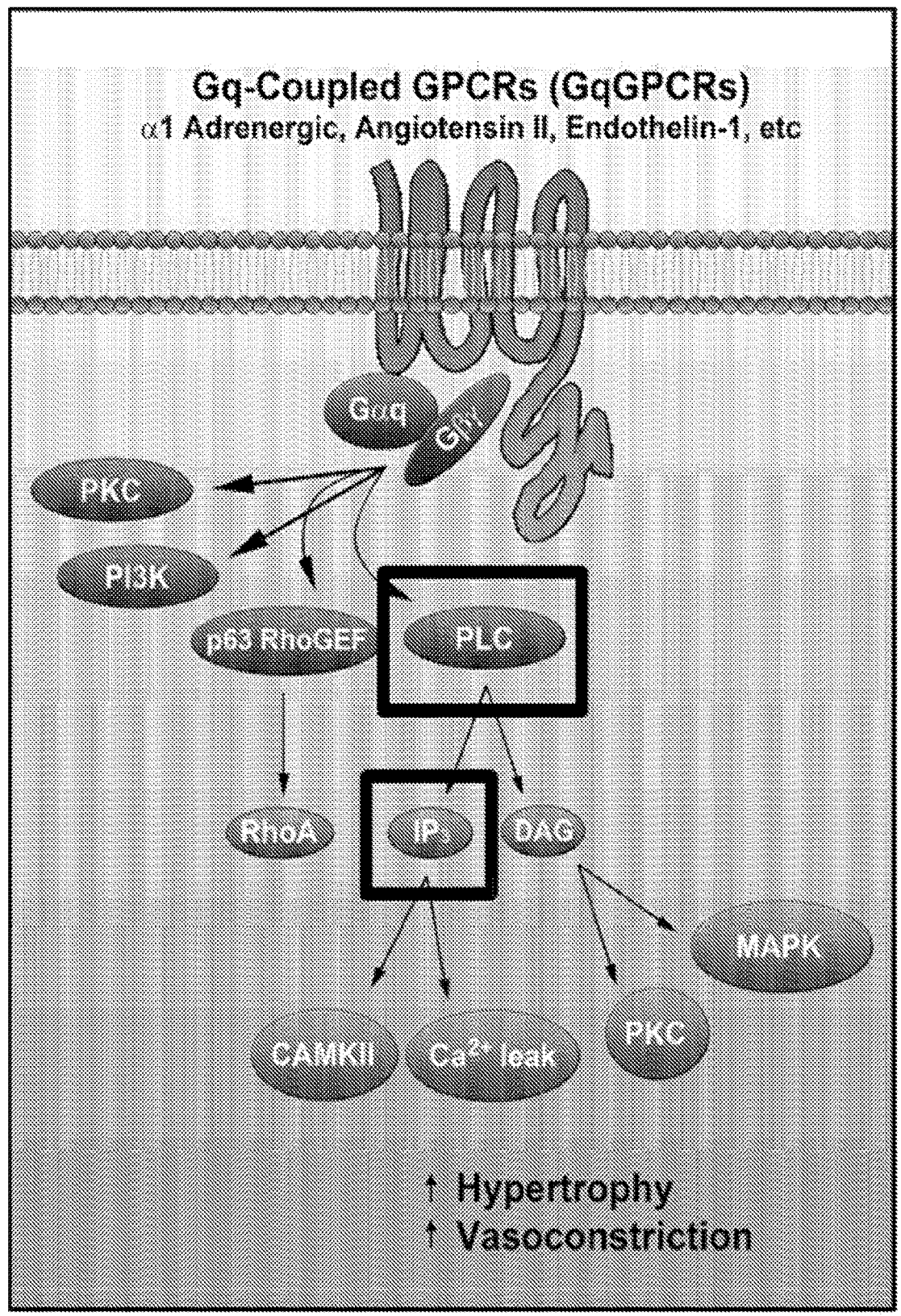
FIG. 19A and FIG. 19B, depicts results from example experiments, demonstrating that no significant difference between NLC and TgβARKnt IP$_3$ levels 4 weeks after Sham or TAC.
Figure 19B:
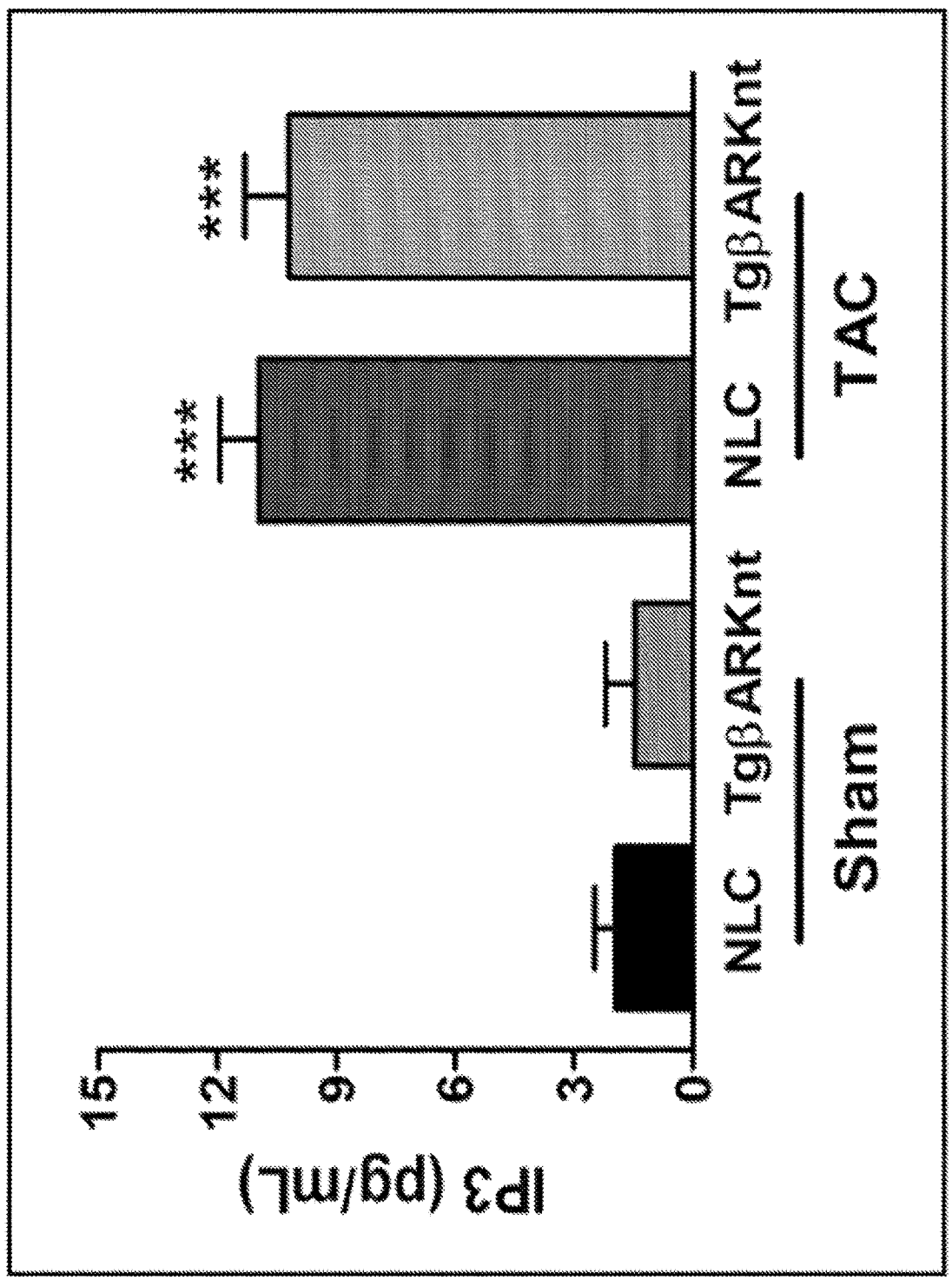
Figure 20B:
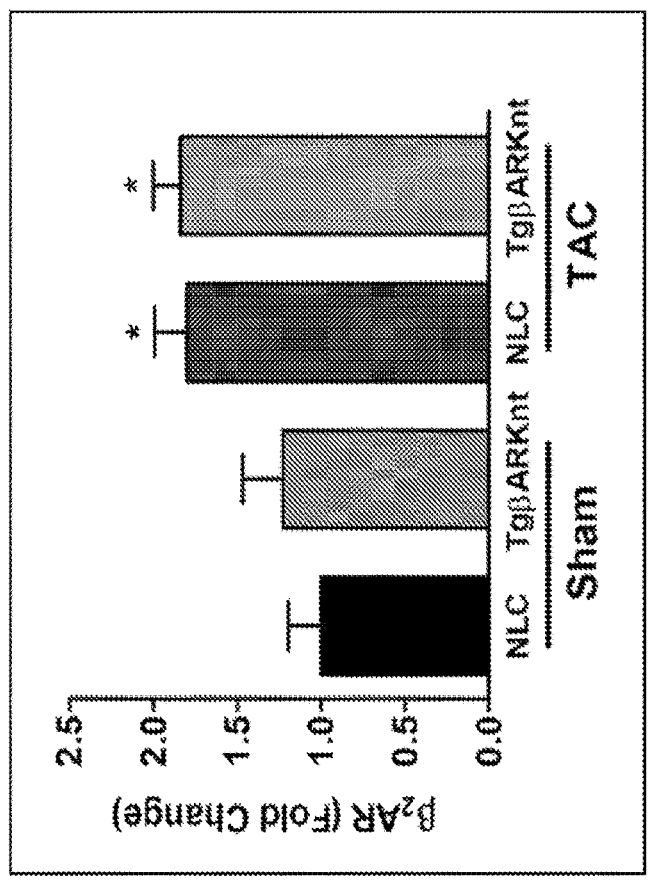
FIG. 20A and FIG. 20B, depicts results from example experiments demonstrating that β Adrenergic Receptor (βAR) is similar in βARKnt and NLC mice 4 weeks post-TAC.
Figure 20A:
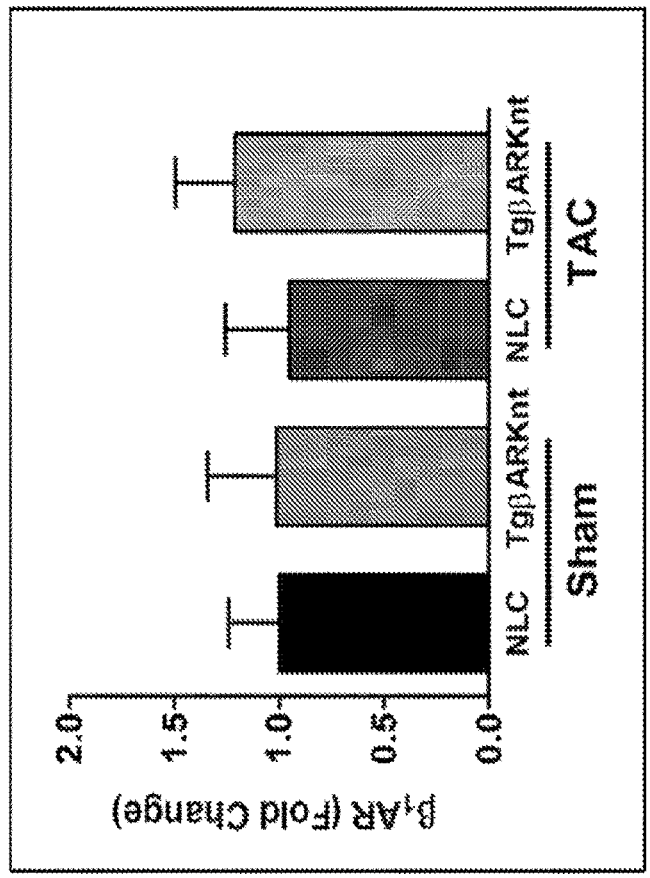
Figure 21B:
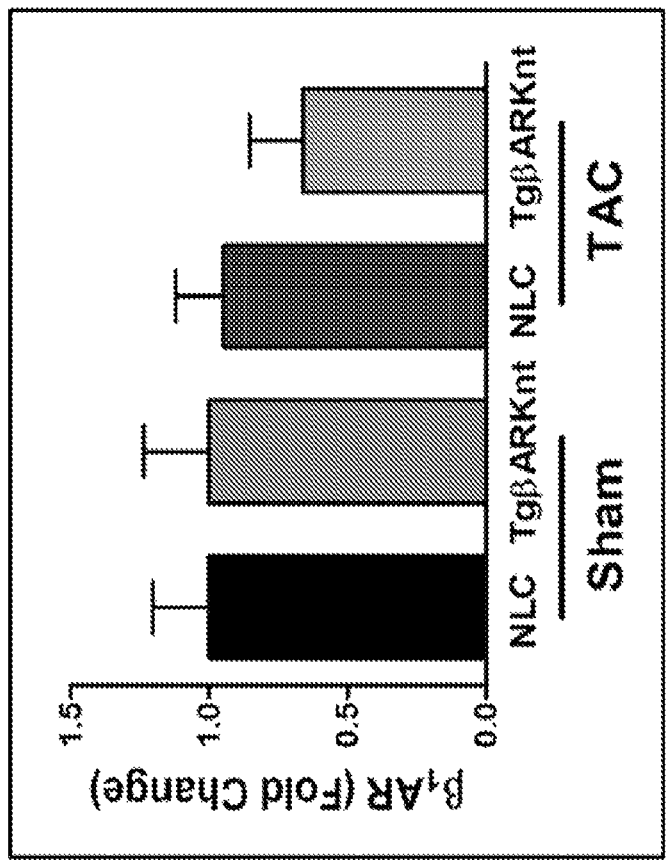
FIG. 21A and FIG. 21B, depicts results from example experiments demonstrating that there is no significant difference in $β_1$AR or $β_2$AR mRNA expression in βARKnt or NLC mice 14 weeks post-TAC.
Figure 21A:
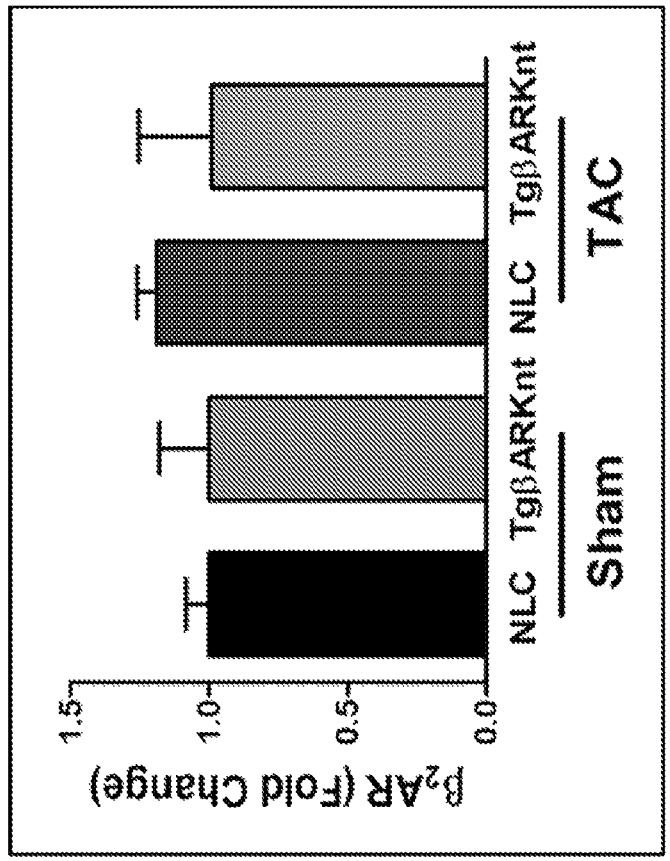

In addition, Gq-mediated activation of PLC via $IP_3$ production was measured and it was found that $IP_3$ levels were elevated to the same degree in NLC and TgβARKnt mice after TAC, suggesting that the physiological effects of βARKnt are not due to altered Gq-coupled GPCR activation (FIG. 19).

To visualize the effect of βARKnt peptide expression on myocardial structure, wheat germ agglutinin staining was performed to measure myocyte cross-sectional area in these mice and a significant increase in myocyte size was observed in transgenic sham animals and an even greater, but equal, increase in NLC and βARKnt mice after TAC, demonstrating an alteration in cardiomyocyte size prior to cardiac stress (FIG. 37).

Figure 38:
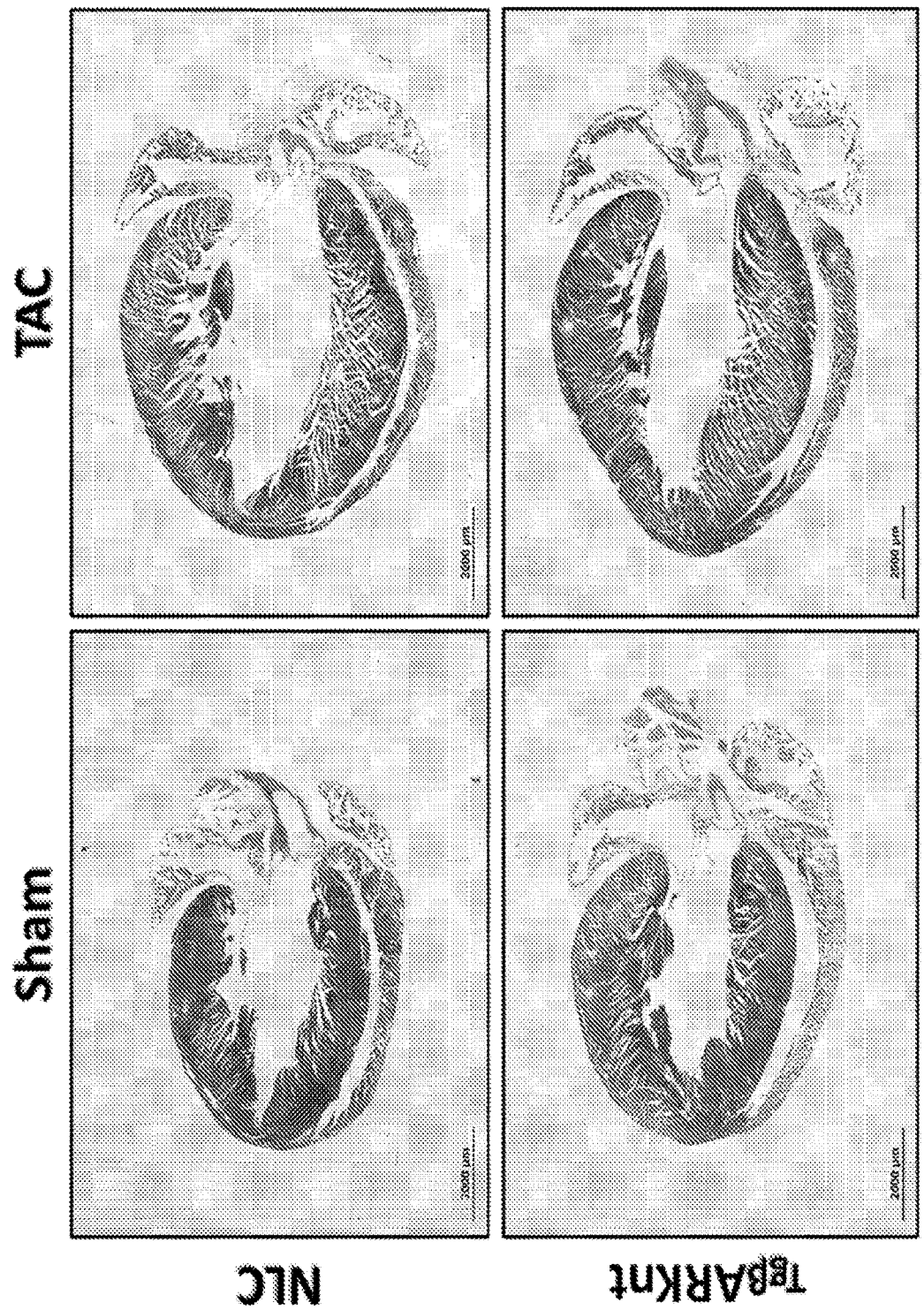
FIG. 38 depicts results from example experiments demonstrating left ventricular structural remodeling is limited in TgβARKnt mice 4 weeks after TAC.
Figure 39:
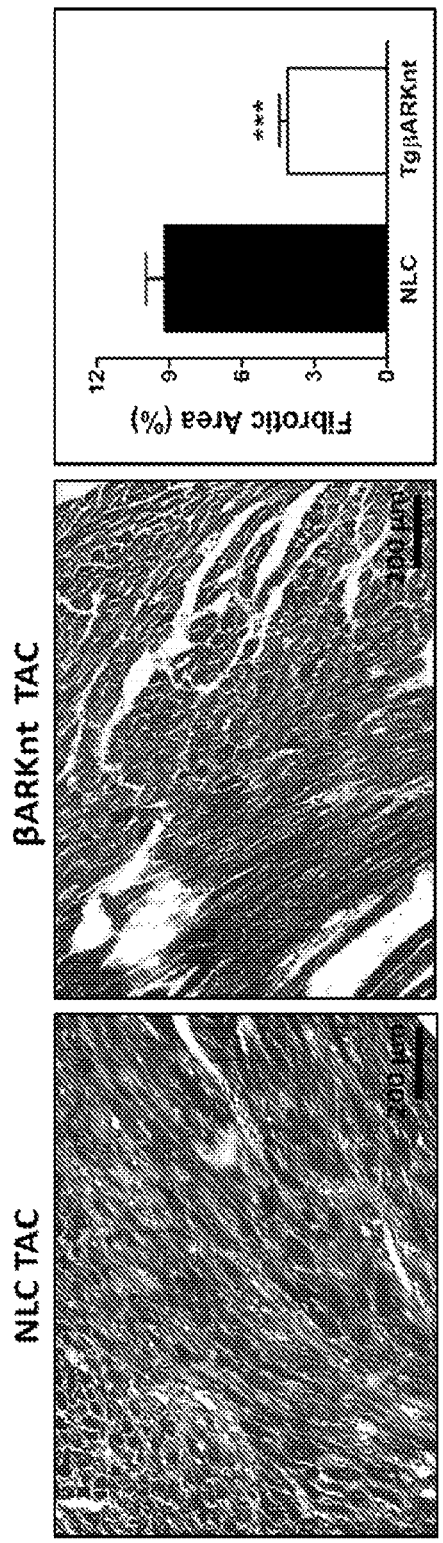
FIG. 39 depicts results from example experiments demonstrating left ventricular structural remodeling is limited in TgβARKnt mice 4 weeks after TAC.

Furthermore, Masson Trichrome staining was performed on paraffin sections taken at the level of the aortic outflow tract. Four chamber images of the myocardium revealed a proportional increase in cardiac size in NLC and βARKnt hearts 4 weeks after TAC. To further investigate the integrity of the myocardium, higher magnification images of the LV were collected and a potential decrease in interstitial fibrosis in the βARKnt transgenic mice was observed. Together, these data suggest that the βARKnt peptide may limit LV remodeling after TAC (FIG. 38).

Figure 22:
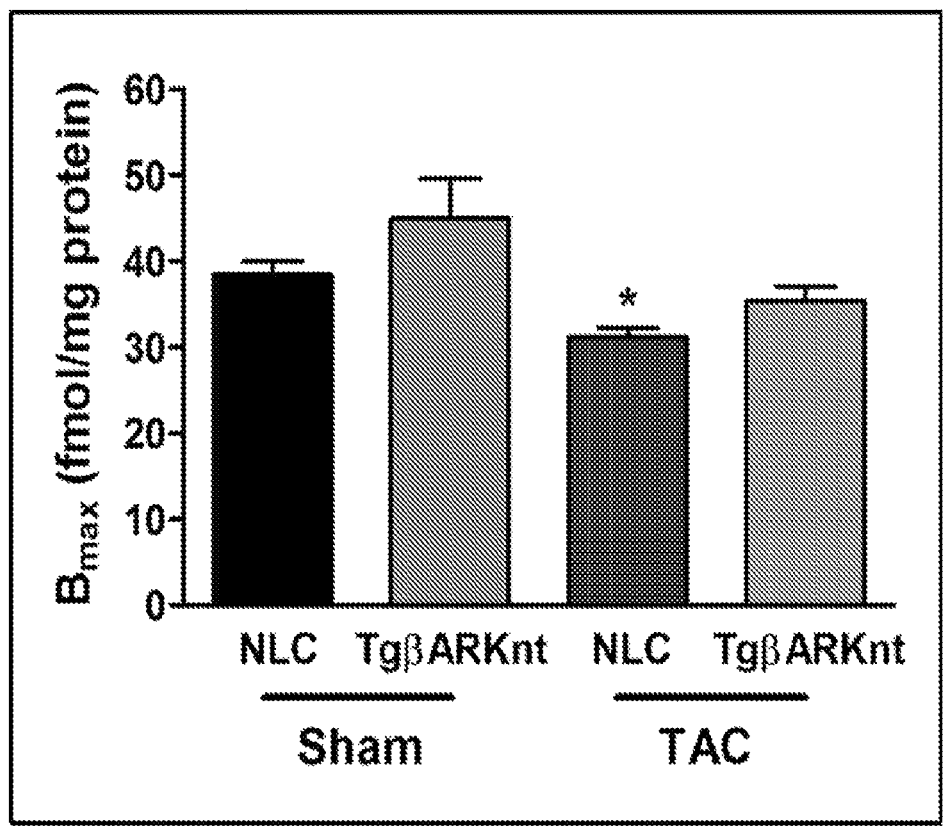
FIG. 22 depicts results from example experiments, demonstrating βAR density is significantly reduced in NLC mice 4 weeks post-TAC.
Figure 23C:
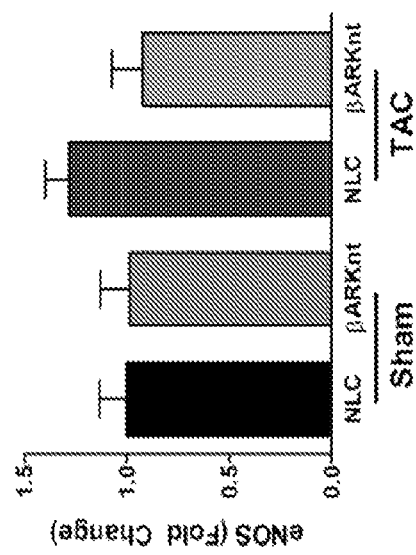
FIG. 23A through FIG. 23C, depicts results from example experiments demonstrating RT-PCR of angiogenesis markers in NLC and TgβARKnt mice 4 weeks post-TAC.
Figure 23B:
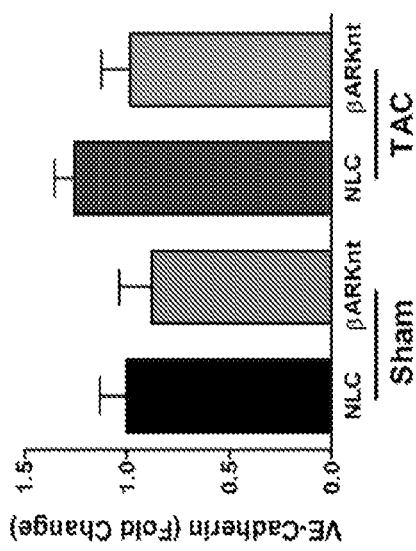
Figure 23A:
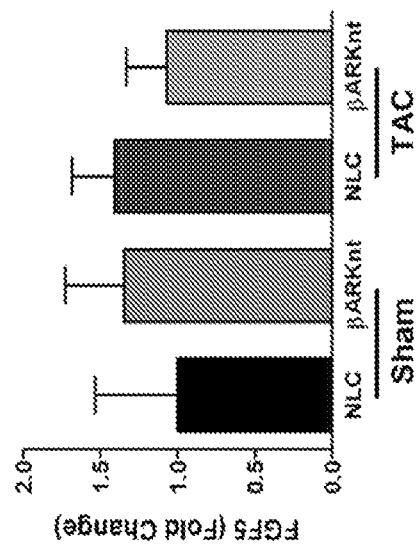
Figure 24A:
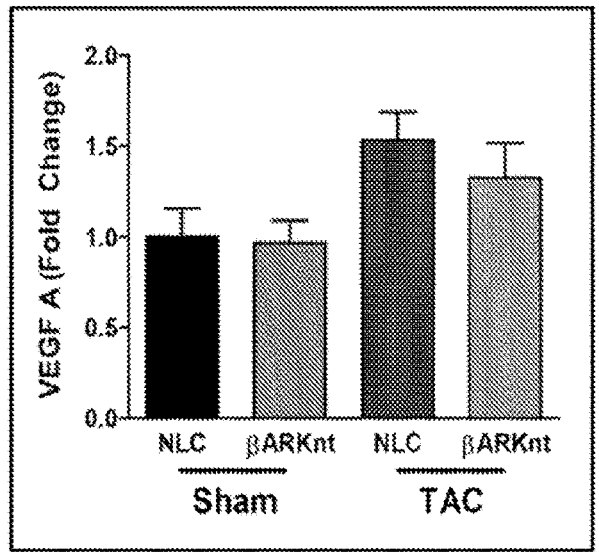
FIG. 24A through FIG. 24D, depicts results from example experiments demonstrating RT-PCR of angiogenesis markers in NLC and TgβARKnt mice 4 weeks post-TAC.
Figure 24B:
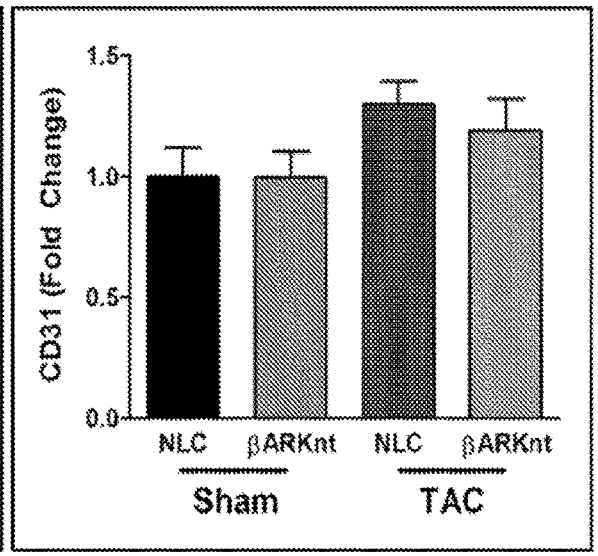
Figure 24C:
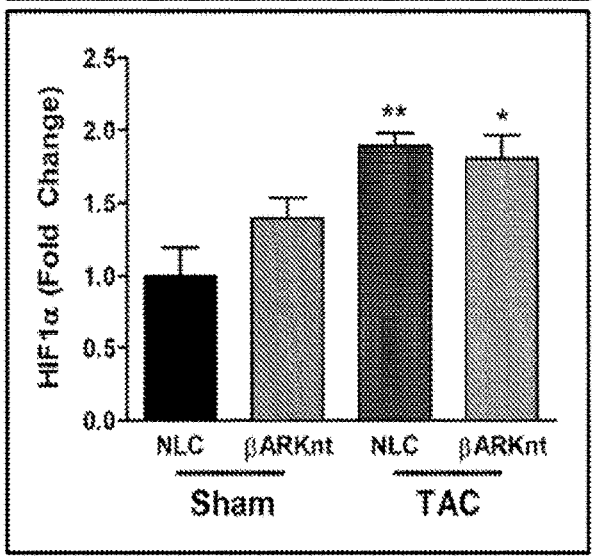
Figure 24D:
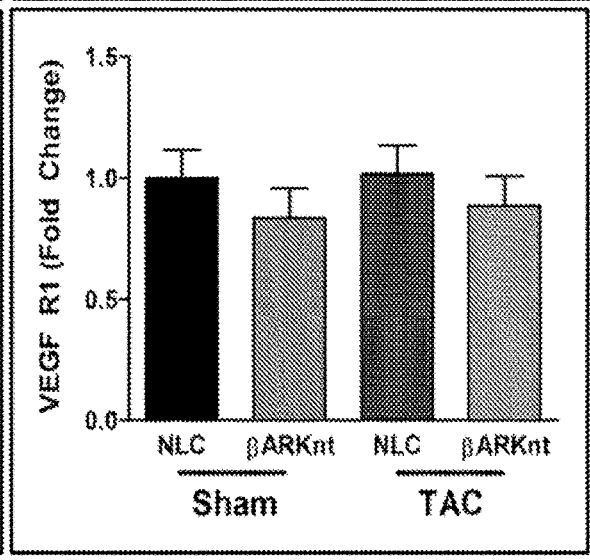
Figure 25A:
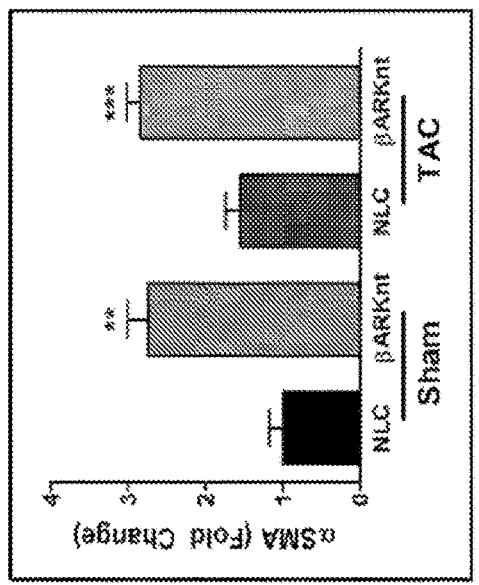
FIG. 25A through 25C, depicts results from example experiments demonstrating RT-PCR of fibrosis markers in NLC and TgβARKnt mice 4 weeks post-TAC.
Figure 25B:
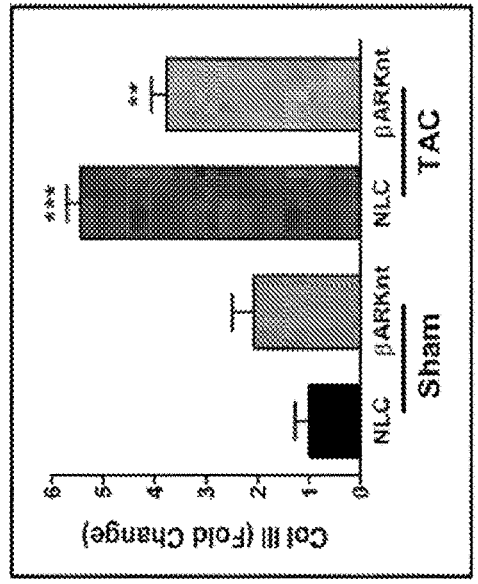
Figure 25C:
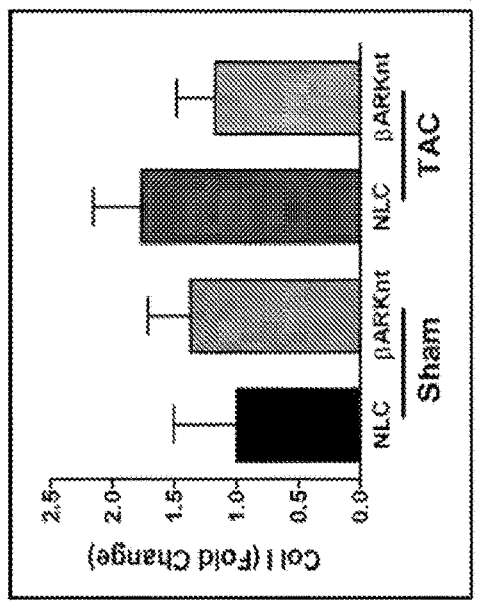
Figure 26A:
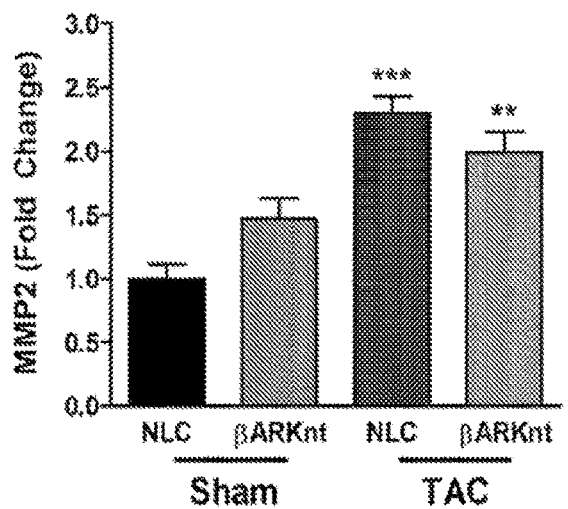
FIG. 26A through FIG. 26D, depicts results from example experiments demonstrating RT-PCR of fibrosis markers in NLC and TgβARKnt mice 4 weeks post-TAC.
Figure 26B:
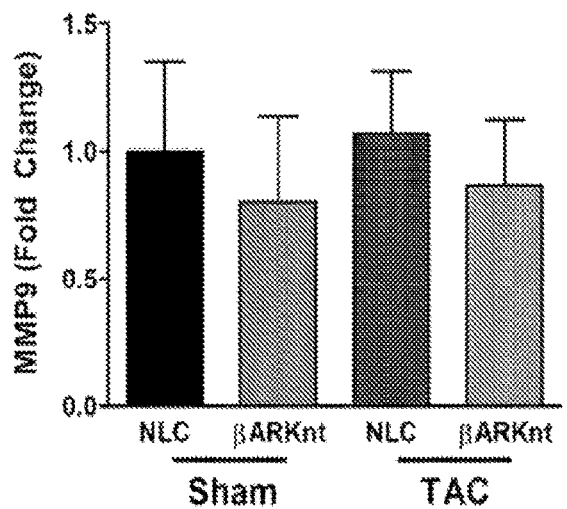
Figure 26C:
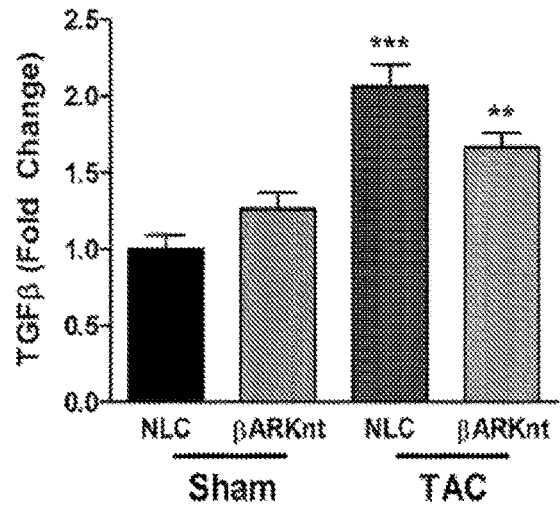
Figure 26D:
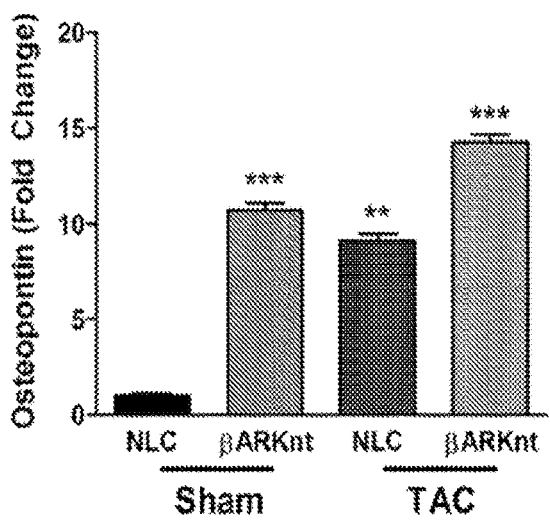
Figure 27B:
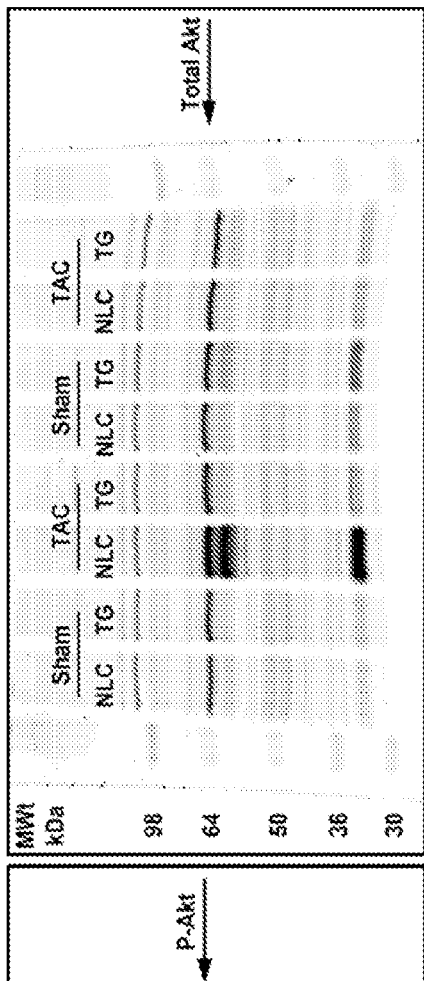
FIG. 27A through FIG. 27C, depicts results from example experiments demonstrating phospho-Akt is increased in βARKnt mice compared to NLC.
Figure 27A:
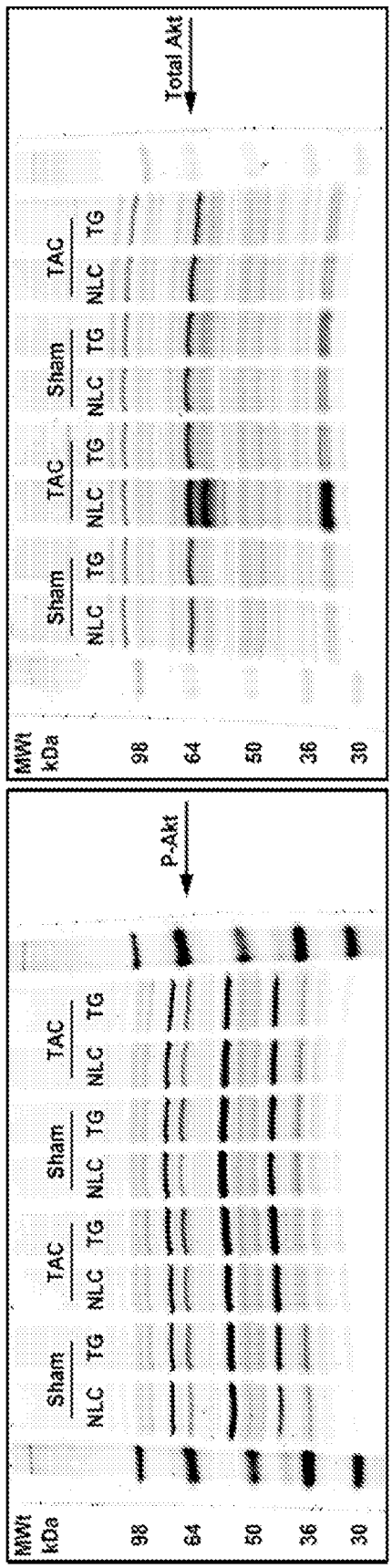
Figure 27C:
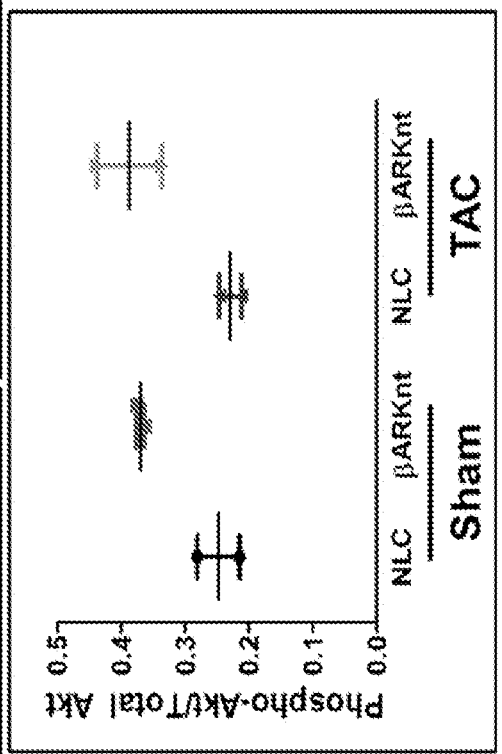
Figure 29A:
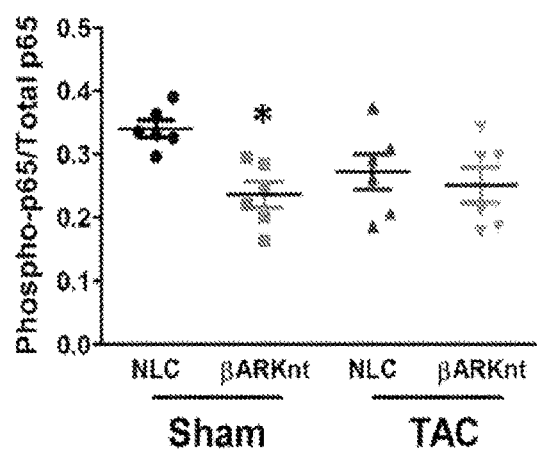
FIG. 29A through FIG. 29D, depicts results from example experiments demonstrating an increase in total p65 (NFkB) and decrease in phospho/total p65 in βARKnt versus NLC mice 4 weeks post-TAC.
Figure 29B:
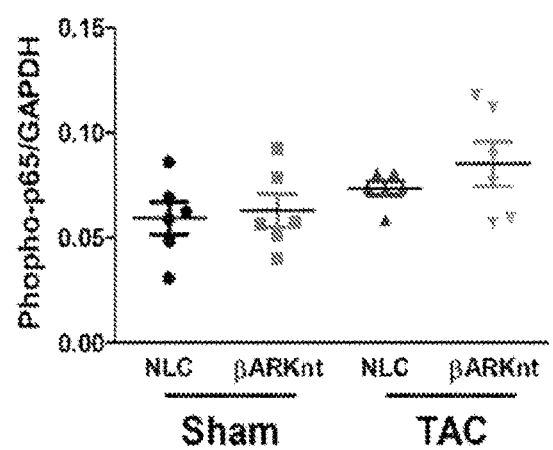
Figure 29C:
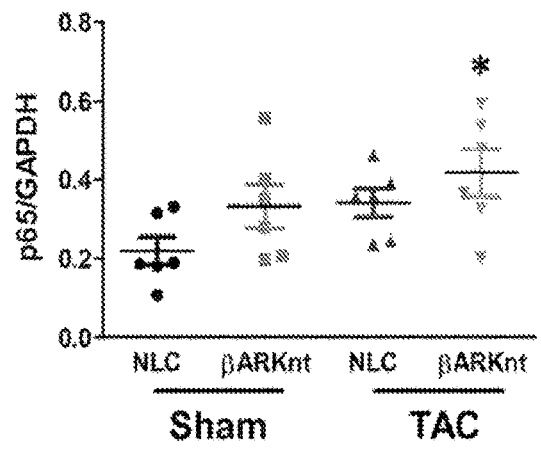
Figure 29D:
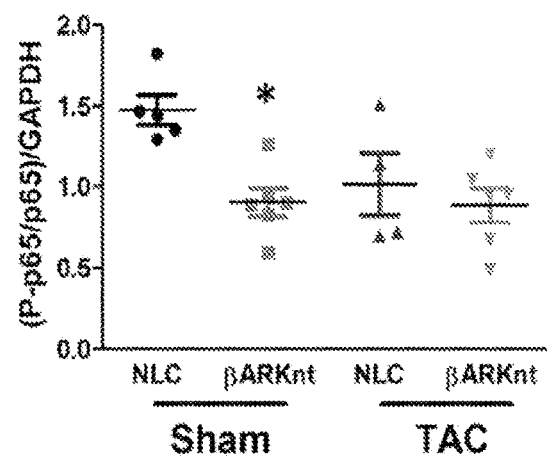
Figure 30A:
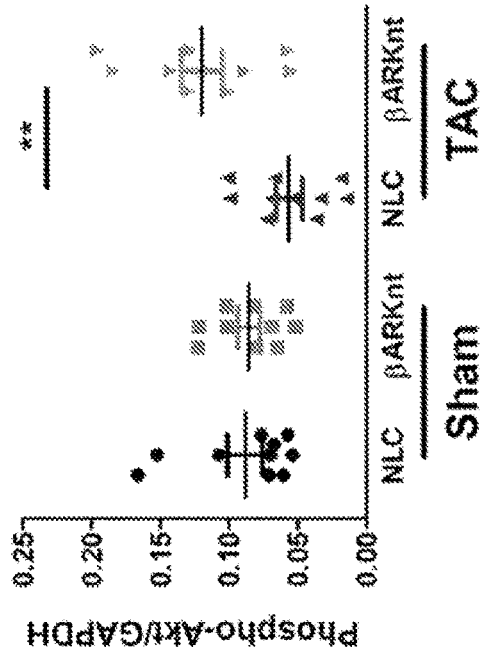
FIG. 30A through FIG. 30D, depicts results from example experiments, demonstrating an increase in phospho/total Akt in βARKnt versus NLC mice 4 weeks post-TAC.
Figure 30B:
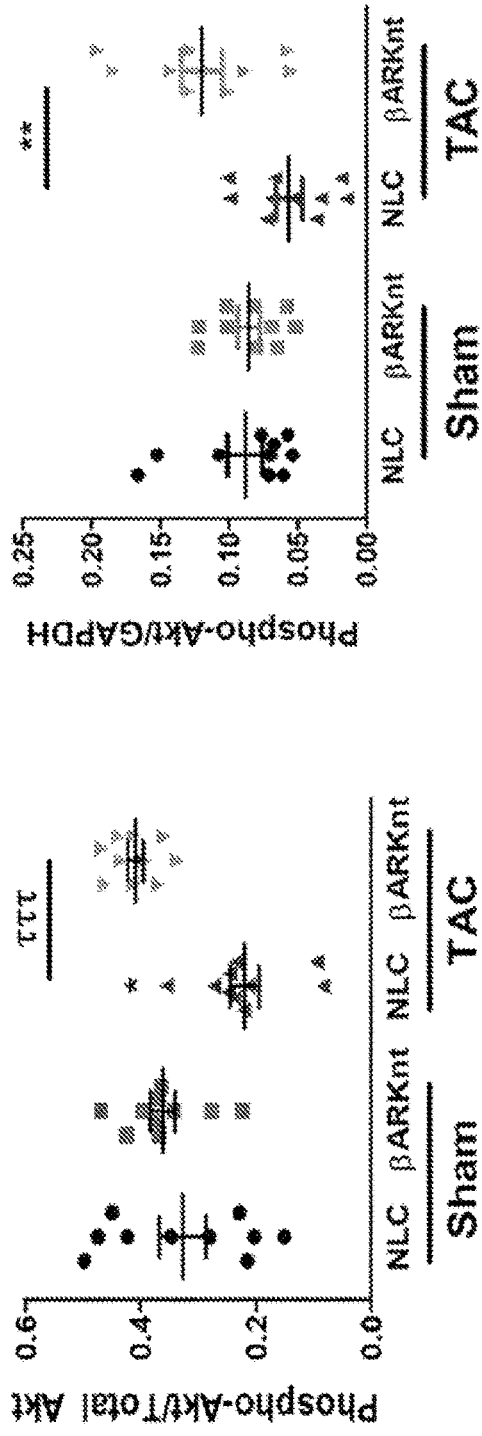
Figure 30C:
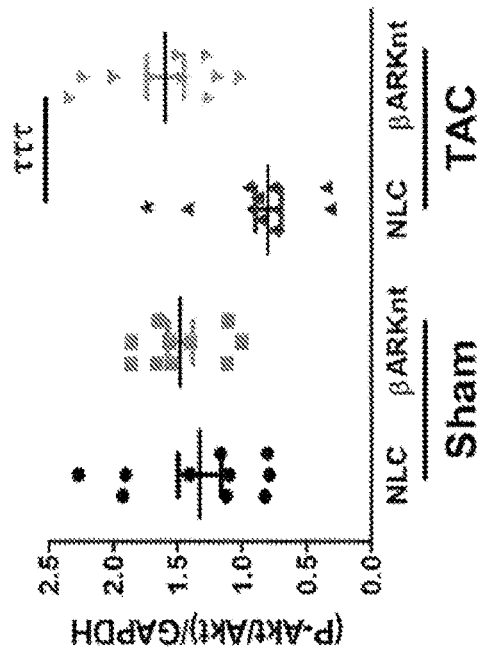
Figure 30D:
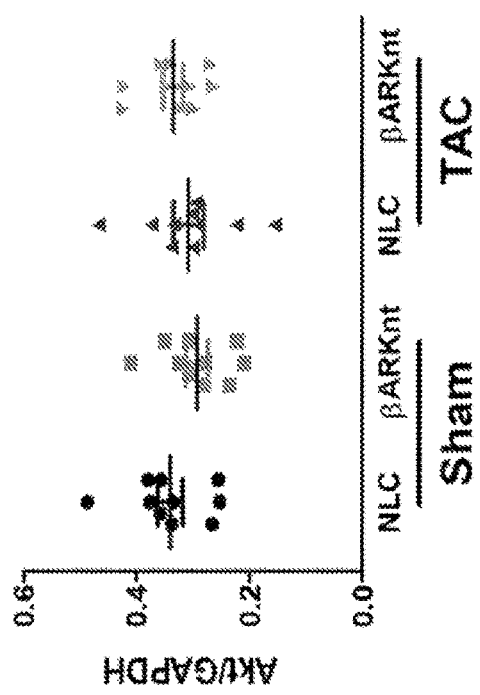
Figure 31B:
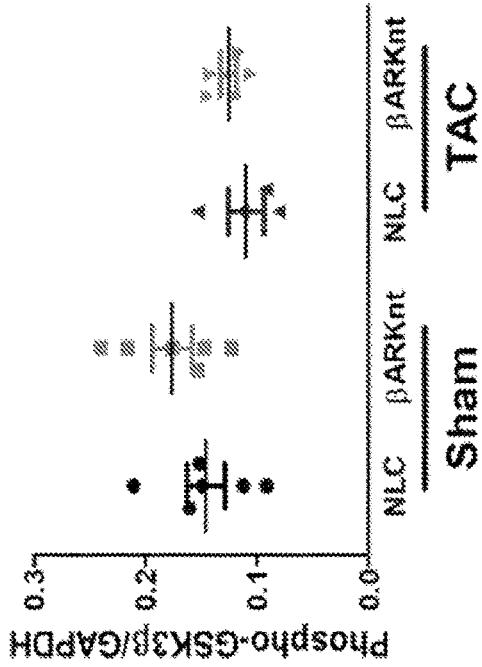
FIG. 31A through FIG. 31D, depicts results from example experiments demonstrating an increase in phospho/total GSK3β in βARKnt Sham mice 4 weeks post-TAC.
Figure 31D:
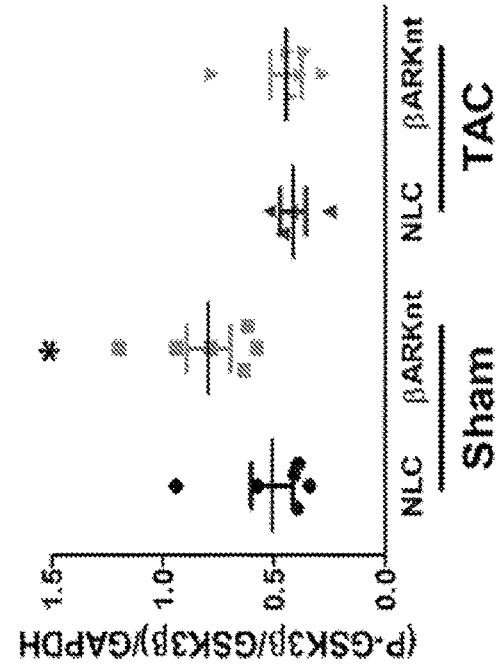
Figure 31A:
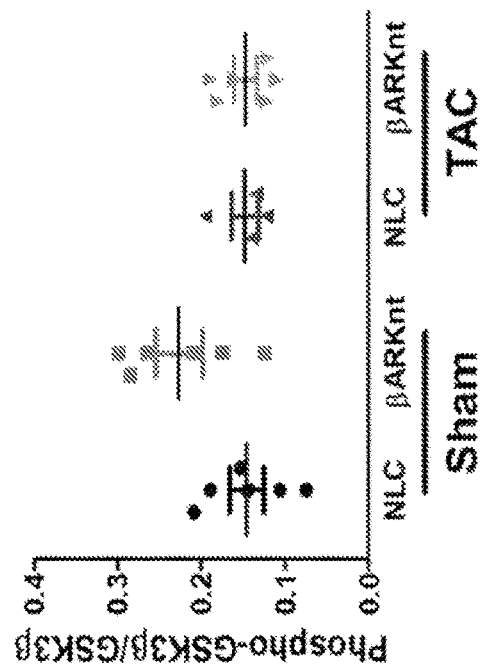
Figure 31C:
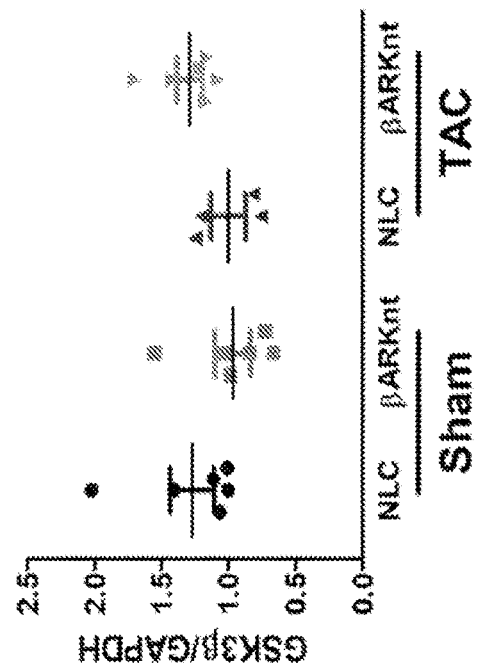
Figure 32:
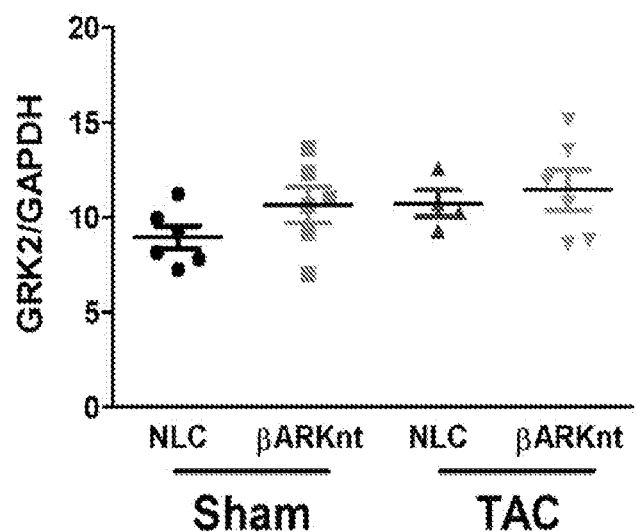
FIG. 32 depicts results from example experiments, demonstrating a trend towards an increase in GRK2/GAPDH in βARKnt versus NLC mice 4 weeks post-TAC.
Figure 32:
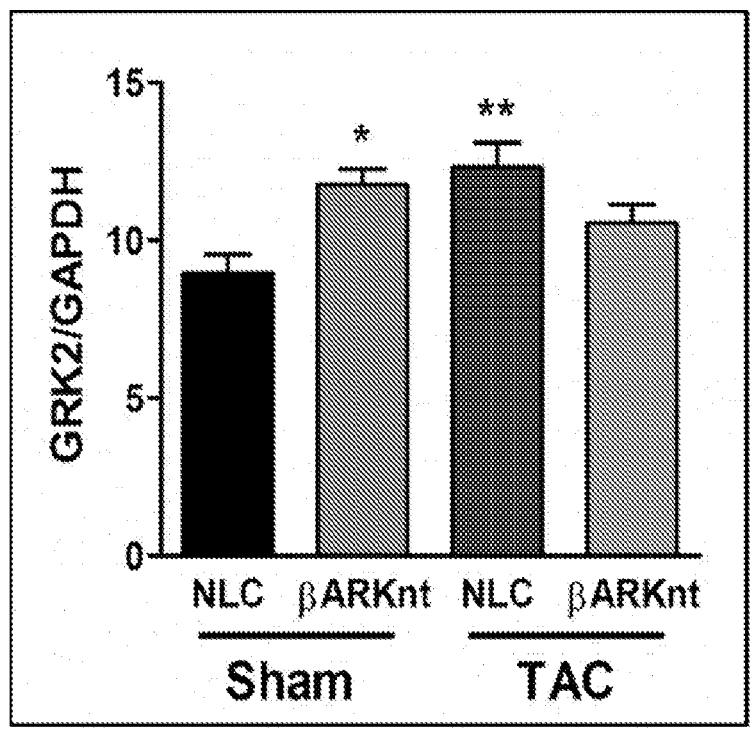
Figure 33A:
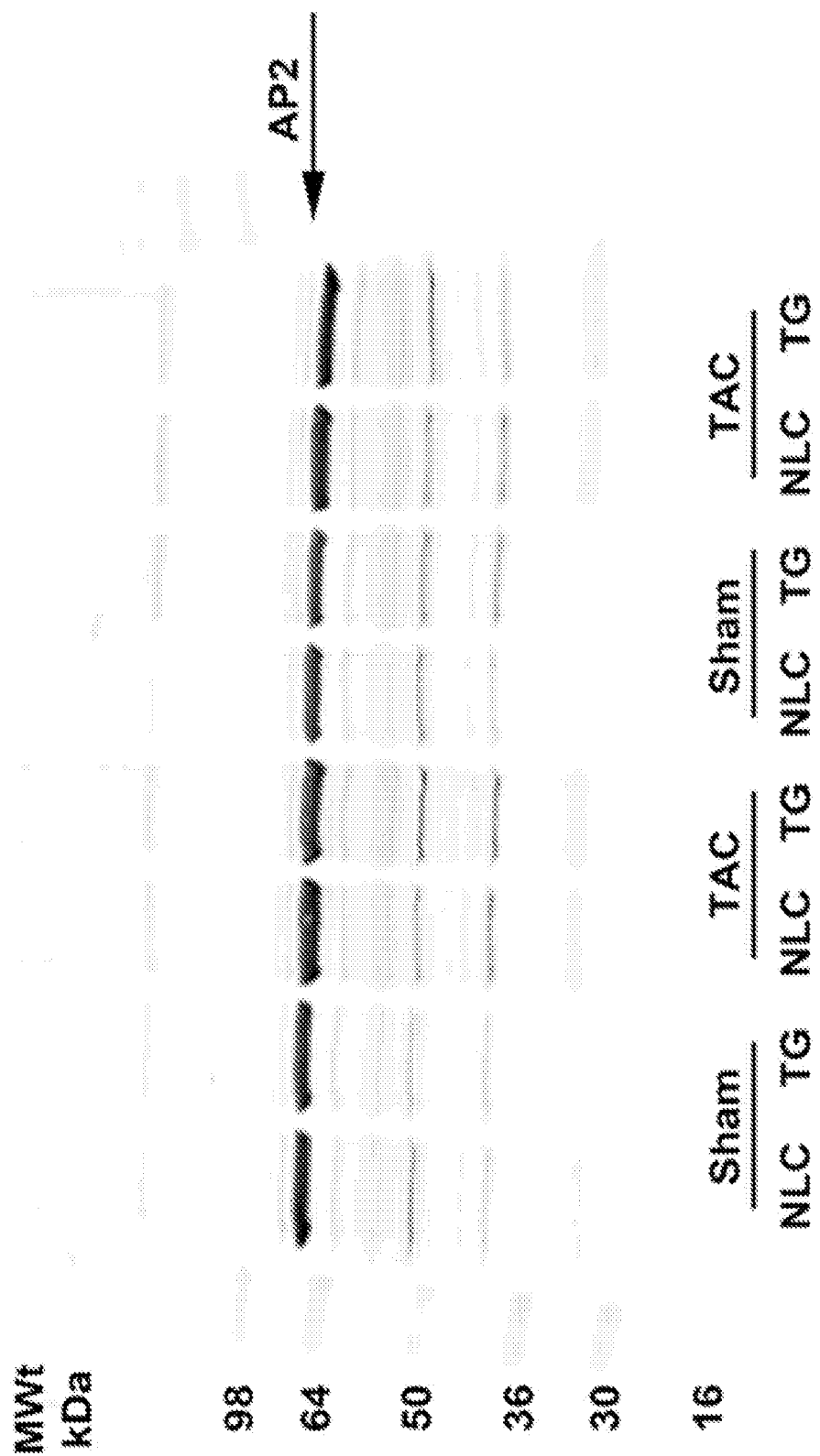
FIG. 33A and FIG. 33B, depicts results from example experiments demonstrating no change in AP2 levels in TgβARKnt or NLC Sham and TAC mice at 4 weeks.
Figure 33B:
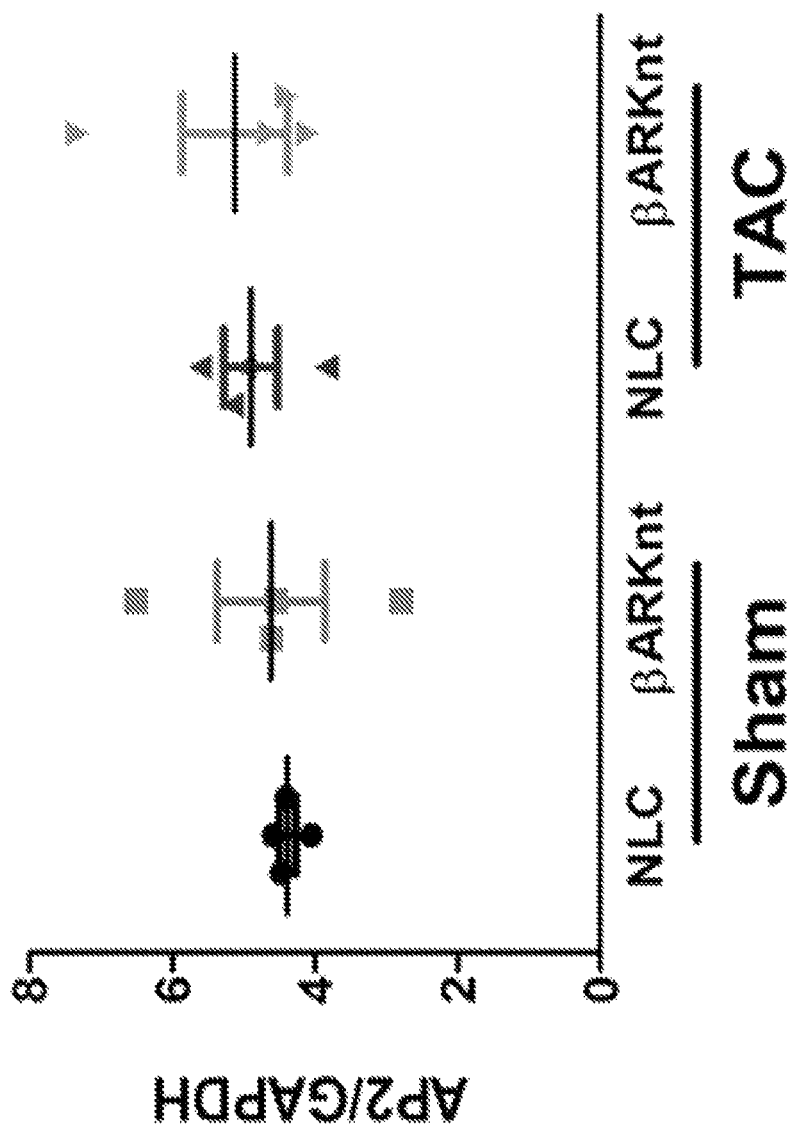
Figure 34B:
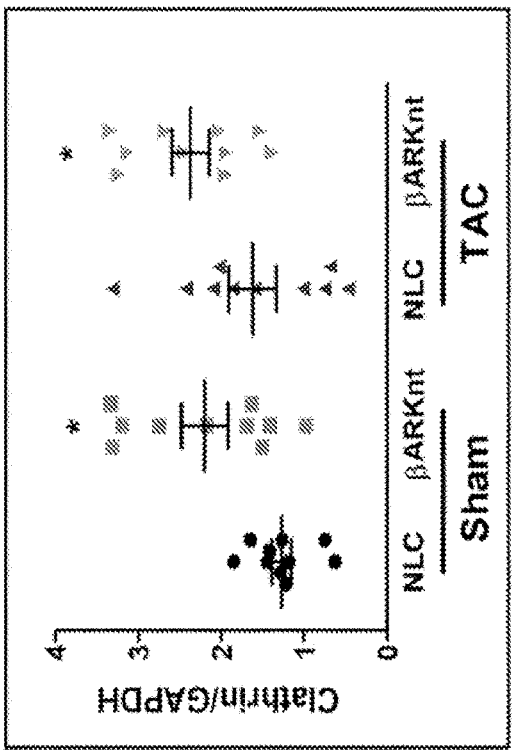
FIG. 34A and FIG. 34B, depicts results from example experiments demonstrating an increase in clathrin in TgβARKnt Sham and TAC and NLC TAC mice at 4 weeks.
Figure 34A:
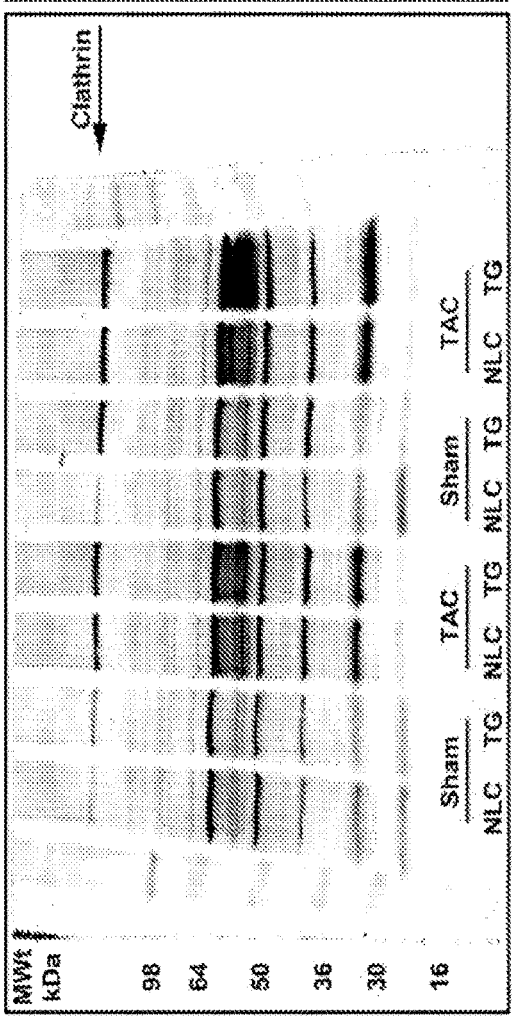
Figure 35A:
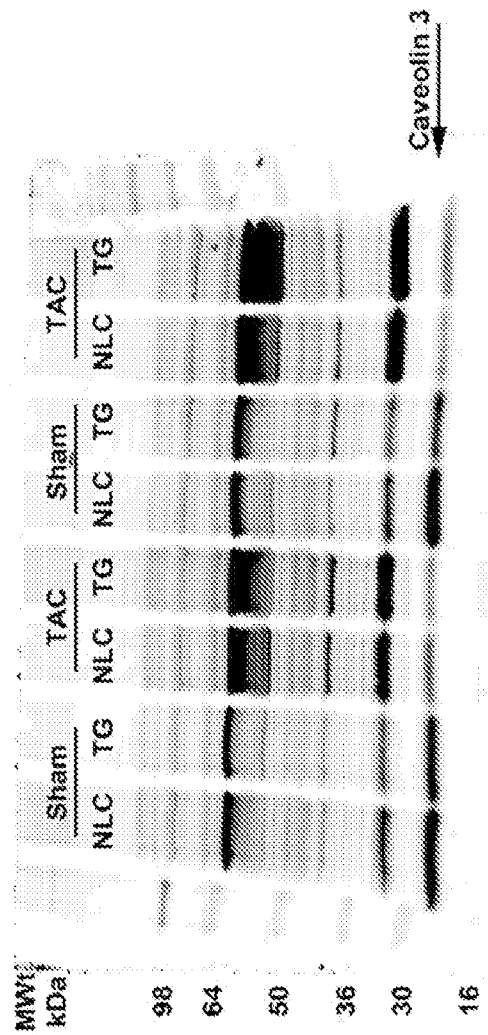
FIG. 35A and FIG. 35B, depicts results from example experiments demonstrating a decrease in Caveolin 3 in TgβARKnt Sham and TAC and NLC TAC mice at 4 weeks.
Figure 35B:
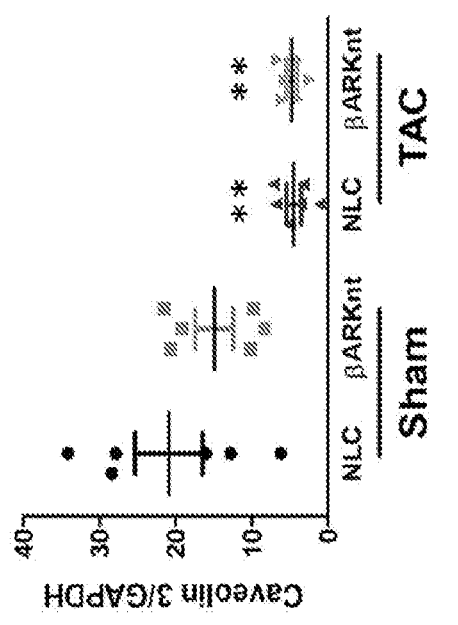
Figure 36A:
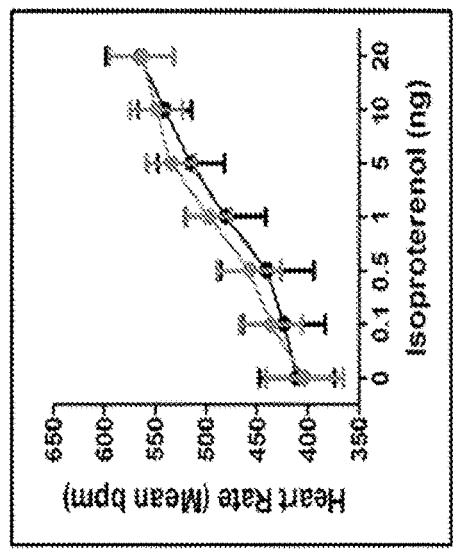
FIG. 36A through FIG. 36D, depicts results from example experiments demonstrating cardiac-specific βARKnt expression does not alter hemodynamic function.
Figure 36B:
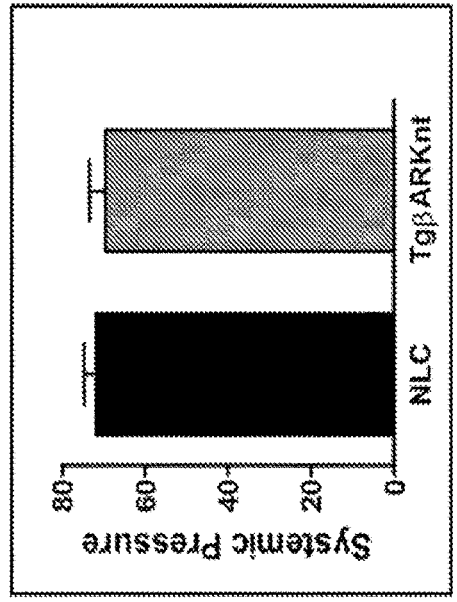
Figure 36C:
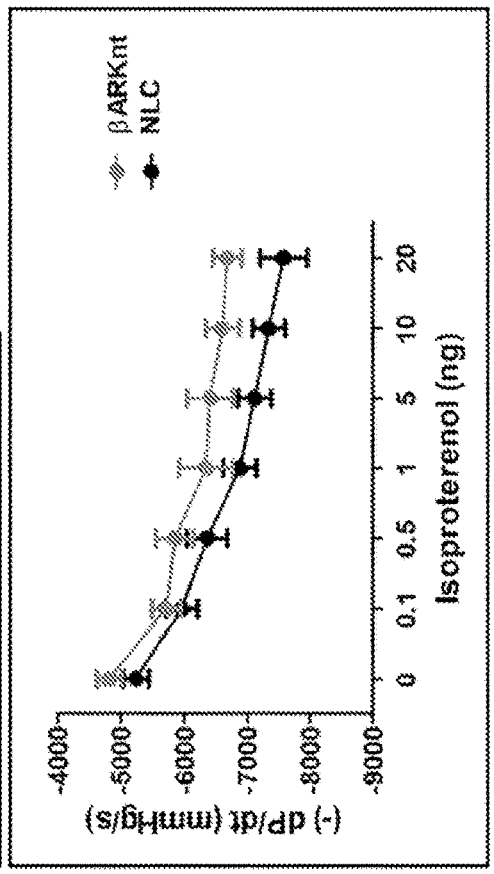
Figure 36D:
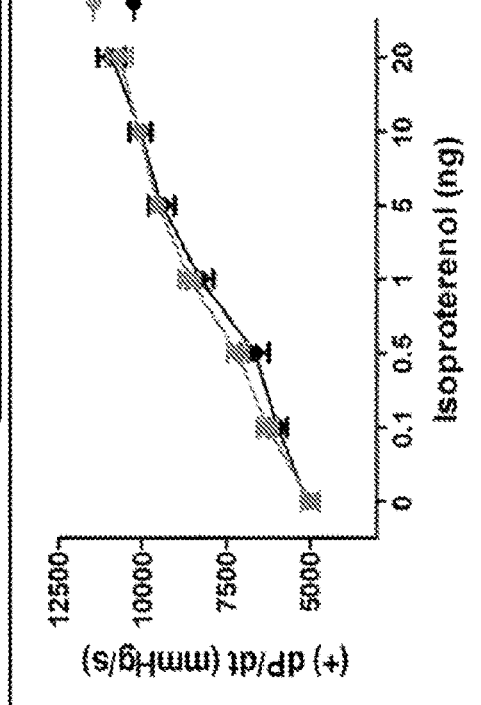

To further elucidate the mechanism of action of the βARKnt peptide, βAR density was measured by radioligand binding and it was found that receptor density was preserved by βARKnt expression after 4 weeks of pressure overload. Further, there was a trend towards an increase in GRK2 levels in these animals. These data are consistent with the original line, though milder, suggesting that there may be a dose-dependent effect of βARKnt peptide expression (FIG. 22, FIG. 32).

Figure 40:
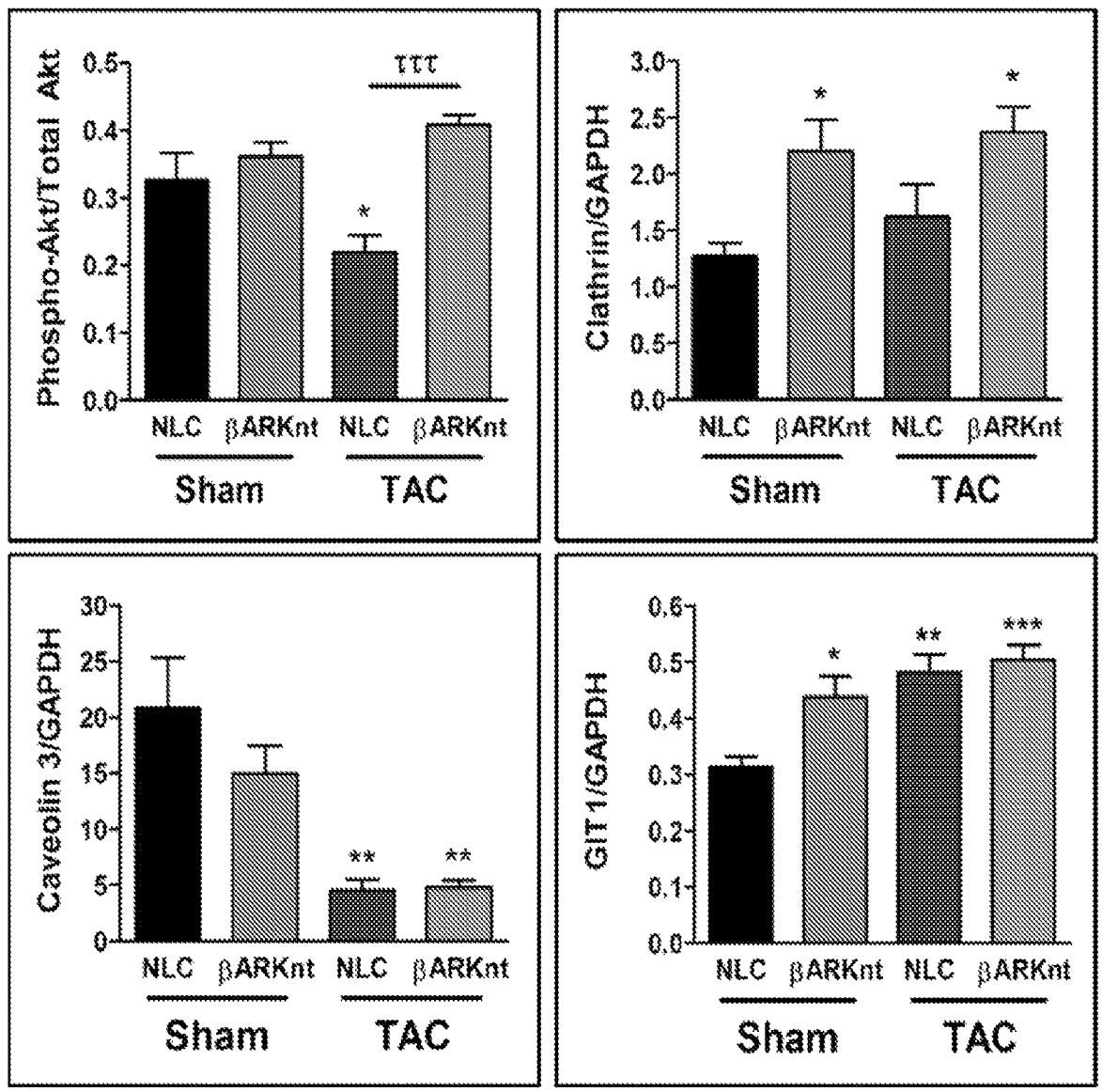
FIG. 40 depicts results from example experiments demonstrating Cardiac signaling is altered in TgβARKnt mice compared to NLC 4 weeks after TAC. *P=0.01, P=0.001; *P<0.0001 by one-way ANOVA with Bonferroni post-hoc test relative to NLC Sham. n=6-10 mice per group.

In addition, a trend towards an increase in clathrin was observed in the transgenic Sham and TAC mice, and it was found that in contrast to the potential decrease in NLC mice, phosphorylated Akt was significantly increased in βARKnt mice after TAC. Together, these data suggest that βAR regulation and cardiac signaling pathways are altered in the βARKnt transgenic hearts (FIG. 40).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for treating or preventing heart failure in a subject, the method comprising administering an effective amount of a composition comprising a nucleic acid encoding a beta-adrenergic receptor kinase N-terminal (βARKnt) peptide, wherein the βARKnt peptide comprises an amino acid sequence at least 90% homologous to SEQ ID NO: 1.

2. The method of claim 1, wherein the nucleic acid encoding a βARKnt peptide, a variant thereof or a fragment thereof is contained within a vector.

3. The method of claim 1, wherein the subject is human.

* * * * *

SEQUENCE LISTING

<160> NUMBER OF SEQ ID NOS: 2

<210> SEQ ID NO 1
<211> LENGTH: 96
<212> TYPE: PRT
<213> ORGANISM: Artificial Sequence
<220> FEATURE:
<223> OTHER INFORMATION: chemically sythesized

<400> SEQUENCE: 1

Arg Gly Glu Val Thr Phe Glu Lys Ile Phe Ser Gln Lys Leu Gly Tyr
1               5                   10                  15

Leu Leu Phe Arg Asp Phe Cys Leu Lys His Leu Glu Glu Ala Lys Pro
            20                  25                  30

-continued

```
Leu Val Glu Phe Tyr Glu Glu Ile Lys Lys Tyr Glu Lys Leu Glu Thr
        35                  40                  45
Glu Glu Glu Arg Leu Val Cys Ser Arg Glu Ile Phe Asp Thr Tyr Ile
    50                  55                  60
Met Lys Glu Leu Leu Ala Cys Ser His Pro Phe Ser Lys Ser Ala Ile
65                  70                  75                  80
Glu His Val Gln Gly His Leu Val Lys Lys Gln Val Pro Pro Asp Leu
                85                  90                  95

<210> SEQ ID NO 2
<211> LENGTH: 85
<212> TYPE: DNA
<213> ORGANISM: Artificial Sequence
<220> FEATURE:
<223> OTHER INFORMATION: chemically synthesized

<400> SEQUENCE: 2
ccttagcaga gctgtggagt gtgacaatgg tgtttgtgtc taaactatca aacgccatta      60
tcacactaaa tagctactgc taggc                                           85
```